(12) United States Patent
Zhang et al.

(10) Patent No.: US 10,196,383 B2
(45) Date of Patent: Feb. 5, 2019

(54) SUBSTITUTED QUINAZOLINE COMPOUNDS AND PREPARATION AND USES THEREOF

(71) Applicant: Sunshine Lake Pharma Co., Ltd., Dongguan, Guangdong (CN)

(72) Inventors: Yingjun Zhang, Dongguan (CN); Chuanfei Jin, Dongguan (CN); Jinheng Gao, Dongguan (CN); Ji Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/745,437

(22) PCT Filed: Jul. 14, 2016

(86) PCT No.: PCT/CN2016/090045
§ 371 (c)(1),
(2) Date: Jan. 17, 2018

(87) PCT Pub. No.: WO2017/012502
PCT Pub. Date: Jan. 26, 2017

(65) Prior Publication Data
US 2018/0215737 A1    Aug. 2, 2018

(30) Foreign Application Priority Data

Jul. 17, 2015   (CN) .......................... 2015 1 0424521

(51) Int. Cl.
| | | |
|---|---|---|
| C07D 403/14 | (2006.01) |
| A61K 45/06 | (2006.01) |
| A61P 25/00 | (2006.01) |
| A61K 31/551 | (2006.01) |

(52) U.S. Cl.
CPC .......... C07D 403/14 (2013.01); A61K 31/551 (2013.01); A61K 45/06 (2013.01); A61P 25/00 (2018.01)

(58) Field of Classification Search
CPC .............................. C07D 403/14; A61K 31/551
See application file for complete search history.

(56) References Cited

U.S. PATENT DOCUMENTS

| | | | |
|---|---|---|---|
| 6,124,299 A | 9/2000 | Baindur et al. |
| 6,297,239 B1 | 10/2001 | deSolms et al. |
| 6,376,515 B2 | 4/2002 | Zhu et al. |
| 6,953,857 B2 | 10/2005 | Nazare et al. |
| 7,612,075 B2 | 11/2009 | Ewing et al. |
| 7,834,035 B2 | 11/2010 | Bessis et al. |
| 7,951,797 B2 | 5/2011 | Breslin et al. |
| 8,039,674 B2 | 10/2011 | Habashita et al. |
| 8,242,121 B2 | 8/2012 | Coleman et al. |
| 8,263,586 B2 | 9/2012 | Cox et al. |
| 8,288,373 B2 | 10/2012 | Chen et al. |
| 8,362,009 B2 | 1/2013 | Bergman et al. |
| 8,399,494 B2 | 3/2013 | Bergman et al. |
| 8,530,648 B2 | 9/2013 | Badiger et al. |
| 8,618,102 B2 | 12/2013 | Coleman et al. |
| 8,653,263 B2 | 2/2014 | Chai et al. |
| 8,680,275 B2 | 3/2014 | Branstetter et al. |
| 8,685,961 B2 | 4/2014 | Brashear et al. |
| 8,901,133 B2 | 12/2014 | Ren et al. |
| 8,940,898 B2 | 1/2015 | Kuduk et al. |
| 8,969,352 B2 | 3/2015 | Gelin et al. |
| 9,062,044 B2 | 6/2015 | Branstetter et al. |
| 9,556,190 B2 | 1/2017 | Kuduk et al. |

(Continued)

FOREIGN PATENT DOCUMENTS

| | | |
|---|---|---|
| AU | 2012200270 A1 | 2/2012 |
| CN | 105461699 A | 4/2016 |

(Continued)

OTHER PUBLICATIONS

1 Christopher D. Cox et al., Discovery of the Dual Orexin Receptor Antagonist [(7R)-4-(5-Chloro-1,3-benzoxazol-2-yl)-7-methyl-1,4-diazepen-1-yl][5-methyl-2-(2H-1,2,3-triazol-2-yl)phenyl] (MK-4305) for the Treatment of Insomnia, Journal of Medicinal Chemistry, Jun. 21, 2010, pp. 5320-5332, vol. 53, Issue 14.
ISR of PCT/CN2015/088799.
Written Opinion of PCT/CN2015/088799.

*Primary Examiner* — Golam M Shameem
(74) *Attorney, Agent, or Firm* — Kam Wah Law

(57) ABSTRACT

The present invention relates quinazolinone compounds of Formula (I), as well as their preparation and uses, and further relates pharmaceutical compositions comprising these compounds and their uses; wherein the compounds or pharmaceutical compositions disclosed herein can be used for antagonizing the orexin receptor. The present invention also relates to uses of the compounds or pharmaceutical compositions in treating or preventing neurological and psychiatric disorders and diseases of the central nervous system in mammals, especially in humans.

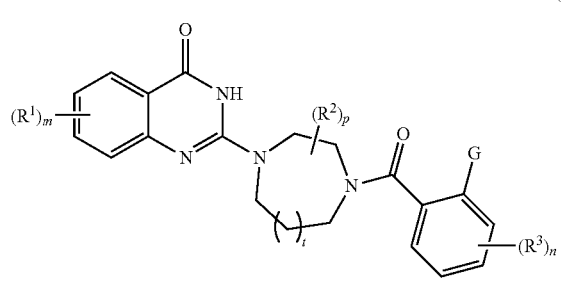

(I)

11 Claims, 14 Drawing Sheets

(56) References Cited

U.S. PATENT DOCUMENTS

| | | |
|---|---|---|
| 9,586,934 B2 | 3/2017 | Kuduk et al. |
| 9,617,246 B2 | 4/2017 | Kuduk et al. |
| 9,676,751 B2 | 6/2017 | Kuduk et al. |
| 9,732,077 B2 | 8/2017 | Kuduk et al. |
| 2007/0197509 A1 | 8/2007 | Babinski et al. |
| 2009/0105318 A1 | 4/2009 | Coleman et al. |
| 2009/0192143 A1 | 7/2009 | Cox et al. |
| 2010/0004284 A1 | 1/2010 | Farina et al. |
| 2012/0101110 A1 | 4/2012 | Badiger et al. |
| 2013/0281465 A1 | 10/2013 | Nozawa et al. |
| 2014/0081025 A1 | 3/2014 | Suzuki et al. |
| 2014/0171430 A1 | 6/2014 | Letavic et al. |
| 2014/0228377 A1 | 8/2014 | Abe et al. |
| 2014/0275065 A1 | 9/2014 | Coate et al. |
| 2014/0275095 A1 | 9/2014 | Dvorak et al. |
| 2014/0364433 A1 | 12/2014 | Kamenecka et al. |
| 2015/0166523 A1 | 6/2015 | Araki et al. |
| 2015/0166527 A1 | 6/2015 | Boss et al. |
| 2015/0252032 A1 | 9/2015 | Bolli et al. |
| 2015/0291558 A1 | 10/2015 | Kuduk et al. |
| 2015/0322039 A1 | 11/2015 | Kuduk et al. |
| 2015/0322040 A1 | 11/2015 | Kuduk et al. |
| 2015/0322041 A1 | 11/2015 | Kuduk et al. |
| 2015/0322074 A1 | 11/2015 | Cooke et al. |
| 2015/0376194 A1 | 12/2015 | Hert et al. |
| 2015/0376198 A1 | 12/2015 | Roberts et al. |
| 2016/0176858 A1 | 6/2016 | Liverton et al. |
| 2016/0185768 A1 | 6/2016 | Liverton et al. |
| 2016/0304490 A1 | 10/2016 | Kuduk et al. |
| 2017/0001985 A1 | 1/2017 | Boss et al. |
| 2017/0217947 A1 | 8/2017 | Barth et al. |
| 2017/0233385 A1 | 8/2017 | He et al. |

FOREIGN PATENT DOCUMENTS

| | | |
|---|---|---|
| WO | 1997036886 A1 | 10/1997 |
| WO | 2000051614 A1 | 9/2000 |
| WO | 2012085852 A1 | 6/2012 |
| WO | 2012114252 A1 | 8/2012 |
| WO | 2013050938 A1 | 4/2013 |
| WO | 2015152367 A1 | 10/2015 |
| WO | 2015152368 A1 | 10/2015 |

SUBSTITUTED QUINAZOLINE COMPOUNDS AND PREPARATION AND USES THEREOF

CROSS-REFERENCE TO RELATED APPLICATIONS

This is a U.S. national stage application of the International Patent Application No. PCT/CN2016/090045, filed 14 Jul. 2016, which claims priority to Chinese Patent Application No. 201510424521.4, filed 17 Jul. 2015, both of which are incorporated herein by reference in their entireties.

FIELD OF THE INVENTION

The present invention belongs to the field of medicine technology, in particular relates to the compounds, as well as their preparation and uses, and relates to pharmaceutical compositions comprising these compounds. More specifically, the present invention relates to substituted quinazolinone compounds, as well as their preparation, and pharmaceutical compositions. Compounds or pharmaceutical compositions of the invention disclosed herein can be used in the manufacture of a medicament for preventing, treating, ameliorating a neurological and psychiatric disorder or disease of central nervous system in a mammal, as well as for selectively antagonizing an orexin receptor.

BACKGROUND OF THE INVENTION

Orexin, also known as hypocretin or orexin peptide, comprises orexin A and orexin B (or hypocretin-1 and hypocretin-2), which is a neuroendocrine hormone secreted by the hypothalamus and functioning in the central nervous system. Its main physiological functions comprise: 1. regulating feeding, orexin can significantly promote feeding, which is in a dose-dependent manner, and activates the neurons that regulate feeding; 2. involving in the regulation of energy metabolism, orexin can significantly increase the metabolic rate; 3. involving in sleep-wake regulation, orexin can inhibit rapid eye movement sleep, and extend wake time, block the role of orexin and can promote sleep; 4. involving in the endocrine regulation, orexin have a very significant effect on the endocrine pituitary hormones; 5. relating with a sense of reward, learning and memory; 6. promoting gastric acid secretion; 7. promoting an increase in drinking water; 8. raising blood pressure; 9. playing a role in the treatment of alcohol addiction, drug addiction, alcoholism, and the like (David C. Piper et al., The novel brain neuropeptide, orexin-A, modulates the sleep-wake cycle of rats. *Eur. J. Neuroscience,* 2000, 12(2), 726-730).

Orexins play a biological role by binding to orexin receptor. Orexin receptor is a G-protein coupled receptor. There are two types, called $OX_1$ and $OX_2$ receptor respectively. They are only distributed in the brain tissue, and there are significant differences between the two distributions, wherein, $OX_1$ receptors are mainly distributed in the ventromedial hypothalamic nucleus, paraventricular nucleus, the hippocampal formation, dorsal raphe nucleus and locus coeruleus area, and $OX_2$ receptors are mainly distributed in the cerebral cortex, subthalamic, hypothalamic paraventricular nucleus and preoptic nucleus (Sakurai T. et al., Orexins and orexin receptors: a family of hypothalamic neuropeptides and G protein-coupled receptors that regulate feeding behavior. *Cell,* 1998, 92(4), 573-585).

Orexins have very important significance for mammals, especially for humans, which widely participate in regulating activities of the central nervous system, and play an important role in the pathology. There are a great many types of neurological and psychiatric disorders and diseases associated with orexin and orexin receptor. Common neurological and psychiatric disorders and diseases of the central nervous system comprise depression, anxiety disorders, seasonal affective disorder, mania, bipolar disorder, obsessive-compulsive disorder, insomnia and fatigue resulting from jet lag, mental schizophrenia, seizures, panic attacks, depression, alcohol addiction, drug addiction, alcoholism, substance abuse, drug addiction withdrawal symptoms, insomnia, psychotic disorders, epilepsy, sleep disorders, sleep disorder, sleep apnea syndrome, mandatory eating disorders, fibromyalgia, stress, obesity, Parkinson's disease, senile dementia, cognitive disorders, memory disorders, premenstrual tension syndrome, migraine headaches, memory loss, Alzheimer silent disease or other disorders related with normal or pathological aging. These diseases have seriously affected the social stability and the quality of life of patients and their families, and some may even lead to death.

In view of this, currently, orexin receptor antagonists have become the research and development focus of drugs resisting to neurological and psychiatric disorders and diseases of the central nervous system.

SUMMARY OF THE INVENTION

The present invention is directed to at least one of the above related art technical problem solved to some extent. The present invention provides compounds with antagonism of orexin receptors, which have better prospects in clinical application. Compared with existing similar compounds, compounds of the present invention have better pharmacodynamic activities, in addition, the compounds of the present invention also have excellent physical and chemical properties, pharmacokinetic properties and low toxicity.

The following is only an overview of some aspects of the present invention, but is not limited thereto. There is a more complete description behind about these and other parts. All references of this specification are incorporated herein by reference in their entirety. When the disclosure of this specification is different with citations, the disclosure of this specification shall prevail.

The present invention provides compounds with orexin receptor antagonist activity, which can be used in the manufacture of a medicament for preventing or treating neurological and psychiatric disorders and diseases of the central nervous system, such as depression, anxiety, mania, alcohol into addiction, drug addiction, alcoholism, bipolar disorder, obsessive-compulsive disorder, stress, sleep disorders, insomnia and fatigue resulting from jet lag and insomnia.

The present invention also provides a method of preparing such compounds and pharmaceutical compositions containing these compounds, and a method of using these compounds or combinations to treat the diseases above in mammals, especially in humans.

The compounds of the invention show good orexin receptor antagonistic activity, with better efficacy, pharmacokinetic properties and/or toxicological characteristics, such as good brain/plasma ratio, good bioavailability, good metabolic stability, low toxicity and high security etc. At the same time, excellent properties of the parameters of the compounds of the present invention, such as half-life, clearance, selectivity, bioavailability, chemical stability, metabolic stability, membrane permeability, solubility etc. can reduce the side effects, expand the therapeutic index or improve the tolerance.

The compounds or pharmaceutical compositions of the present invention can be a good antagonizing orexin receptor which can be used for the prevention or treatment of diseases related to the orexin receptor.

Specifically:

In one aspect, provided herein is a compound having Formula (I) or a stereoisomer, an N-oxide, a solvate, a metabolite, a pharmaceutically acceptable salt or a prodrug thereof,

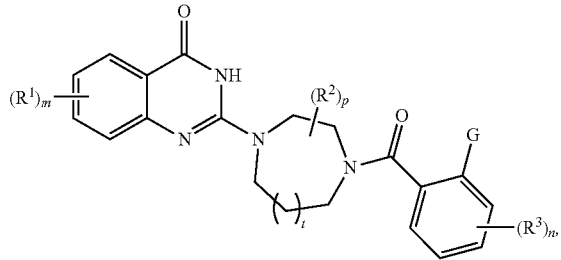

(I)

wherein

G is a 5- to 6-membered heterocycloalkyl or heteroaryl group containing at least one nitrogen, wherein G is further optionally substituted with one or more $R^8$;

each $R^1$ is independently H, D, F, Cl, Br, I, OH, $NH_2$, $NO_2$, CN, $N_3$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ hydroxyalkyl, $C_{1-6}$ alkylamino, $C_{3-12}$ carbocyclyl, 3- to 12-membered heterocyclyl, $C_{6-10}$ aryl or 5- to 12-membered heteroaryl, wherein, each $R^1$ is optionally and independently substituted with one or more $R^8$;

each $R^2$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ hydroxyalkyl or $C_{1-4}$ haloalkyl.

each $R^3$ is independently H, D, F, Cl, Br, I, OH, $NH_2$, $NO_2$, CN, $N_3$, $C_{1-6}$ alkyl, $C_{2-6}$ alkenyl, $C_{2-6}$ alkynyl, $C_{3-12}$ carbocyclyl, 3- to 12-membered heterocyclyl, $C_{6-10}$ aryl or 5- to 12-membered heteroaryl, $-(CR^4R^{4a})_q-OR^7$, $-(CR^4R^{4a})_q-NR^5R^6$, $-(CR^4R^{4a})_qS(=O)_rR^7$, $-(CR^4R^{4a})_qS(=O)_2NR^5R^6$, $-(CR^4R^{4a})_qC(=O)R^7$, $-(CR^4R^{4a})_qOC(=O)R^7$, $-(CR^4R^{4a})_qC(=O)OR^7$, $-(CR^4R^{4a})_qN(R^5)C(=O)R^7$, $-C(=NR^7)NR^5R^6$, $-N(R^7)C(=O)NR^5R^6$, $-(CR^4R^{4a})_q-N(R^5)S(=O)_rR^7$ or $-(CR^4R^{4a})_qC(=O)NR^5R^6$, wherein each $R^3$ is optionally and independently substituted with one or more $R^8$;

each $R^4$ and $R^{4a}$ is independently H, D, F, Cl, Br, I, CN, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ haloalkoxy, $C_{1-4}$ haloalkylamino, $C_{3-8}$ carbocyclyl, 3- to 8-membered heterocyclyl, $C_{6-10}$ aryl or 5- to 6-membered heteroaryl;

each $R^5$, $R^6$ and $R^7$ is independently H, $C_{1-4}$ alkyl, $C_{2-4}$ alkenyl, $C_{2-4}$ alkenyl, $C_{3-8}$ carbocyclyl, ($C_{3-6}$ cycloalkyl)-($C_{1-4}$ alkylene)-, 3- to 8-membered heterocyclyl, (3- to 6-membered heterocyclyl)-($C_{1-4}$ alkylene)-, phenyl, ($C_{6-10}$ aryl)-($C_{1-4}$ alkylene)-, 5- to 6-membered heteroaryl or (5- to 6-membered heteroaryl)-($C_{1-4}$ alkylene)-, or $R^5$ and $R^6$ together with the nitrogen atom to which they are attached, independently and optionally form 3- to 6-membered heterocyclyl, wherein each $C_{1-4}$ alkyl, $C_{2-4}$ alkenyl, $C_{2-4}$ alkynyl and $C_{3-8}$ carbocyclyl is optionally and independently substituted with one or more substituents selected from D, F, Cl, Br, OH, $NH_2$, CN, $N_3$, $C_{1-4}$ alkyl, $C_{1-4}$ haloalkyl, $C_{1-4}$ alkoxy or $C_{1-4}$ alkylamino;

each $R^8$ is independently H, D, F, Cl, Br, I, =O, OH, $NH_2$, $NO_2$, CN, $N_3$, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ haloalkyl, $C_{1-4}$ haloalkoxy, $C_{1-4}$ hydroxyalkyl or $C_{1-4}$ haloalkylamino;

m and n are each independently 0, 1, 2, 3 or 4;

t is 0 or 1;

p is 0, 1, 2, 3, 4, or 5;

each r is independently 0, 1 or 2;

each q is independently 0, 1, 2, 3 or 4.

In some embodiments, G is:

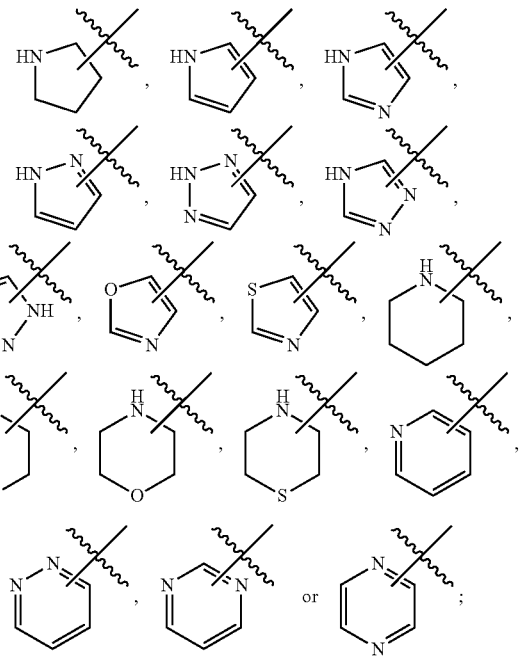

G is optionally substituted with one or more $R^8$; and wherein each $R^8$ is as defined herein.

In some embodiments, each $R^1$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ hydroxyalkyl, $C_{1-4}$ alkylamino, $C_{3-8}$ carbocyclyl, 3- to 8-membered heterocyclyl, $C_{6-10}$ aryl or 5- to 6-membered heteroaryl, wherein, each $R^1$ is optionally and independently substituted with one or more $R^8$; and wherein each $R^8$ is as defined herein.

In other embodiments, each $R^1$ is independently H, D, F, Cl, Br, OH, $NH_2$, $NO_2$, CN, methyl, ethyl, n-propyl, isopropyl, n-butyl, isobutyl, vinyl, ethynyl, methoxy, ethoxy, methylamino, ethylamino, hydroxymethyl, hydroxyethyl, trifluoromethyl, cyclopropyl, piperidinyl, piperazinyl, morpholinyl, phenyl, pyrrolyl, imidazolyl, thiazolyl or thienyl.

In some embodiments, each $R^2$ is independently H, F, Cl, OH, $NH_2$, $NO_2$, CN, methyl, ethyl, n-propyl, isopropyl, vinyl, allyl, propargyl, methoxy, ethoxy, methylamino, ethylamino, hydroxymethyl, hydroxyethyl or trifluoromethyl.

In some embodiments, each $R^3$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{3-8}$ carbocyclyl, 3- to 8-membered heterocyclyl, $C_{6-10}$ aryl or 5- to 6-membered heteroaryl, $-(CR^4R^{4a})_q-OR^7$, $-(CR^4R^{4a})_q-NR^5R^6$, $-(CR^4R^{4a})_q$ S(=O)$_r$R$^7$, —(CR$^4$R$^{4a}$)$_q$S(=O)$_2$NR$^5$R$^6$, —(CR$^4$R$^{4a}$)$_q$C(=O)R$^7$, —(CR$^4$R$^{4a}$)$_q$OC(=O)R$^7$, —(CR$^4$R$^{4a}$)$_q$C(=O)OR$^7$, —(CR$^4$R$^{4a}$)$_q$—N(R$^5$)C(=O)R$^7$, —C(=NR$^7$)NR$^5$R$^6$, —N(R$^7$)C(=O)NR$^5$R$^6$, —(CR$^4$R$^{4a}$)$_q$—N(R$^5$)S(=O)$_r$R$^7$ or —(CR$^4$R$^{4a}$)$_q$C(=O)NR$^5$R$^6$, wherein each R$^3$ is optionally and independently substituted with one or more R$^8$; and wherein, each R$^4$, R$^{4a}$, R$^5$, r, q, R$^6$, R$^7$ and R$^8$ is as defined herein.

In other embodiments, each R$^3$ is independently H, D, F, Cl, Br, OH, NH$_2$, NO$_2$, CN, methyl, ethyl, n-propyl, isopropyl, n-butyl, isobutyl, vinyl, ethynyl, methoxy, ethoxy, methylamino, ethylamino, hydroxymethyl, hydroxyethyl, trifluoromethyl, cyclopropyl, piperidinyl, piperazinyl, morpholinyl, phenyl, pyrrolyl, imidazolyl, thiazolyl, thienyl, —C(=O)NH$_2$ or —COOH.

In some embodiments, each R$^4$ and R$^{4a}$ is independently H, D, F, Cl, Br, I, CN, methyl, ethyl, isopropyl, vinyl, allyl, ethynyl, propargyl, methoxy, tert-butoxy, methylamino, —OCF$_3$, —NHCF$_3$, cyclopentyl, cyclohexyl, piperidin-1-yl, piperazin-1-yl, pyridin-2-yl, phenyl or naphthyl; and each R$^5$, R$^6$ and R$^7$ is independently H, methyl, ethyl, isopropyl, vinyl, allyl, ethynyl, propargyl, cyclopentyl, cyclohexyl, cyclohexylmethyl, piperidin-1-yl, piperazin-1-yl, imidazol-1-yl, pyridin-4-yl-methyl, phenyl or benzyl, or R$^5$ and R$^6$ together with the nitrogen atom to which they are attached, form pyrrolidinyl, piperazinyl, imidazolidinyl or morpholinyl.

In some embodiments, each R$^8$ is independently H, D, F, Cl, Br, I, =O, OH, NH$_2$, NO$_2$, CN, N$_3$, methyl, ethyl, ethynyl, propynyl, methoxy, tert-butoxy, methylamino, trifluoromethyl, trifluoromethoxy, hydroxymethyl or trifluoromethanamino.

In other aspect, provided herein is a pharmaceutical composition comprising the compound disclosed herein.

In some embodiments, the pharmaceutical composition disclosed herein further comprises pharmaceutically acceptable excipient, carrier, adjuvant, solvent or a combination thereof.

In other embodiments, provided herein is a pharmaceutical composition of further comprising an active ingredient for preventing or treating a neurological and psychiatric disorder or disease of the central nervous system, wherein the active ingredient comprises antidepressant, an antianxiety drug, an emotional stabilizer lithium salt, an antipsychotic, an atypical antipsychotic, an antiepileptic, an anti-Parkinson's disease drug, a sedative-hypnotic drug, an antihistamine, a GABA receptor agonist a GABA reuptake inhibitor drug, a monoamine oxidase inhibitor drug, a melatonin receptor agonist drug, an orexin receptor antagonist drug or a combination thereof.

In other embodiments, the active ingredient for preventing or treating neurological and psychiatric disorders and diseases of the central nervous system comprise amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate (or Eskalith), buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, perphenazine, midazolam, triazolam, estazolam, diazepam, flurazepam, nitrazepam, clonazepam, temazepam, flunitrazepam, oxazepam, zolpidem, zaleplon, zopiclone, eszopiclone, indiplon, tiagabine, gaboxadol, clomipramine, doxepin, chloral hydrate, haloperidol, chlorpromazine, carbamazepine, promethazine, lorazepam, hydroxyzine, aspirin, diphenhydramine, chlorpheniramine, lendormin, ramelteon, tasimelteon, agomelatine, mianserin, femoxetine, nabilone, doxepin, gabapentin, chlordiazepoxide, suvorexant, Xuezang Guben or any combination thereof.

In other aspect, provided herein is use of the compound or the pharmaceutical composition in the manufacture of a medicament for preventing, treating or lessening a neurological and psychiatric disorder or disease of the central nervous system in a mammal, including a patient.

In some embodiments, the neurological and psychiatric disorder or disease of the central nervous system refers to depression, an anxiety disorder, a seasonal affective disorder, mania, a bipolar disorder, obsessive-compulsive disorder, insomnia and fatigue resulting from jet lag, mental schizophrenia, seizure, panic attack, melancholia, alcohol addiction, drug addiction, alcoholism, substance abuse, drug addiction withdrawal symptoms, insomnia, a psychotic disorder, epilepsy, somnipathy, sleep disorder, sleep apnea syndrome, a mandatory eating disorder, fibromyalgia, stress, obesity, Parkinson's disease, a cognitive disorder, a memory disorder, premenstrual tension syndrome, a migraine headache, memory loss, Alzheimer silent disease or a disorder related to normal or pathological aging.

In other aspect, provided herein is use of the compound or the pharmaceutical composition disclosed herein in the manufacture a medicament for selectively antagonizing an orexin receptor.

In other aspect, provided herein is a method of preparing, separating or purifying the compound of Formula (I).

Biological tests show that the compounds of the present invention can be used as good orexin receptor antagonists.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as are commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry" by Michael B. Smith and Jerry March, John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In some embodiments, "patient" refers to a human.

The term "comprise" is an open expression, it includes the contents disclosed herein, but don't exclude other contents.

"Stereoisomer" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting points, boiling points, spectral properties or biological activities. A mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations.

As described herein, compounds disclosed herein may optionally be substituted with one or more substituents, such as are illustrated generally below, or as exemplified by particular classes, subclasses, and species of the invention.

In general, the term "substituted" refers to the replacement of one or more hydrogen radicals in a given structure with the radical of a specified substituent. Unless otherwise indicated, an substituted group may have a substituent at each substitutable position of the group. When more than one position in a given structure can be substituted with more than one substituent selected from a specified group, the substituent may be either the same or different at each position.

The term "unsubstituted" refers to the specified group bears no substituents.

The term "optionally substituted with . . . " can be used interchangeably with the term "unsubstituted or substituted with . . . ", i.e., the structure is unsubstituted or substituted with one or more substituents defined herein. Substituents of the present invention include, but are not limited to D, F, Cl, Br, I, $N_3$, CN, $NO_2$, OH, SH, $NH_2$, alkyl, haloalkyl, haloalkoxy, haloalkylamino, alkenyl, alkynyl, alkoxy, alkylamino, cycloalkyl, heterocyclyl, aryl, heteroaryl, $-(CR^4R^{4a})_q-OR^7$, $-(CR^4R^{4a})_q-NR^5R^6$, $-(CR^4R^{4a})_qS(=O)_rR^7$, $-(CR^4R^{4a})_qS(=O)_2NR^5R^6$, $-(CR^4R^{4a})_qC(=O)R^7$, $-(CR^4R^{4a})_qOC(=O)R^7$, $-(CR^4R^{4a})_qC(=O)OR^7$, $-(CR^4R^{4a})_q-N(R^5)C(=O)R^7$, $-C(=NR^7)NR^5R^6$, $-N(R^7)C(=O)NR^5R^6$, $-(CR^4R^{4a})_q-N(R^5)S(=O)_rR^7$, $-(CR^4R^{4a})_qC(=O)NR^5R^6$, and the like. Wherein, each $R^4$, $R^{4a}$, $R^5$, $R^6$, $R^7$, q and r is as defined herein.

Furthermore, unless otherwise stated, the phrase "each . . . is independently" is used interchangeably with the phrase "each (of) . . . and . . . is independently". It should be understood broadly that the specific options expressed by the same symbol are independent of each other in different radicals; or the specific options expressed by the same symbol are independent of each other in same radicals. Taking $R^4$ for an example, the specific options expressed by $R^4$ of the formula "$-(CR^4R^{4a})_q-OR^7$" and the formula "$-(CR^4R^{4a})_q-NR^5R^6$" are independent of each other; Meanwhile, in the same formula, such as formula "$-(CR^4R^{4a})_q-OR^7$", q is 2, the specific options of two $R^4$ also are independent of each other.

At various places in the present specification, substituents of compounds disclosed herein are disclosed in groups or in ranges. It is specifically intended that the invention includes each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon group, wherein the alkyl group is optionally substituted with one or more substituents described herein. Unless otherwise stated, the alkyl group contains 1-20 carbon atoms. In some embodiments, the alkyl group contains 1-12 carbon atoms. In other embodiments, the alkyl group contains 3-12 carbon atoms. In still other embodiments, the alkyl group contains 1-6 carbon atoms. In yet other embodiments, the alkyl group contains 1-4 carbon atoms.

Some non-limiting examples of alkyl groups include, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), 1-heptyl, 1-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. And alkylene group is exemplified by methylene ($-CH_2-$), ethylene ($-CH_2CH_2-$), isopropylene ($-CH(CH_3)CH_2-$), and the like.

The term "alkenyl" refers to linear or branched-chain monovalent hydrocarbon radical with at least a carbon-carbon, sp double bond, and includes radicals having "cis" and "trans" orientations, or alternatively, "E" and "Z" orientations. The alkenyl radical may be optionally substituted independently with one or more substituents described herein. In some embodiments, the alkenyl contains 2 to 12 carbon atoms. In other embodiments, the alkenyl contains 3 to 12 carbon atoms. In still other embodiments, the alkenyl contains 2 to 6 carbon atoms. In yet other embodiments, the alkenyl contains 2 to 4 carbon atoms. Examples of alkenyl groups include, but are not limited to, ethylenyl or vinyl ($-CH=CH_2$), allyl ($-CH_2CH=CH_2$), and the like.

The term "alkynyl" refers to a linear or branched monovalent hydrocarbon radical of 2 to 12 carbon atoms, i.e., a carbon-carbon, sp triple bond, wherein the alkynyl radical may be optionally substituted independently with one or more substituents described herein. In some embodiments, the alkynyl contains 3 to 12 carbon atoms. In other embodiments, the alkynyl contains 2 to 6 carbon atoms. In still other embodiments, the alkynyl contains 2 to 4 carbon atoms. Examples of such groups include, but are not limited to, ethynyl ($-C\equiv CH$), propargyl ($-CH_2C\equiv CH$), 1-propynyl ($-C\equiv C-CH_3$), and the like.

The term "alkoxy" refers to an alkyl group, as previously defined, attached to the parent molecular moiety via an oxygen atom. Unless otherwise specified, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms. The alkoxy group may be optionally substituted with one or more substituents disclosed herein.

Some non-limiting examples of the alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "alkylamino" embraces "N-alkylamino" and "N,N-dialkylamino" where amino groups are independently substituted with one alkyl radical or with two alkyl radicals, respectively, and wherein the alkylamino is as defined herein. In some embodiments, the alkylamino group is lower alkylamino group having one or two alkyl groups of 1 to 6 carbon atoms attached to nitrogen atom. In some embodiments, the alkylamino group is an alkylamino group having one or two lower alkyl groups of 1 to 4 carbon atoms attached to nitrogen atom. Some non-limiting examples of suitable alkylamino radical include mono or dialkylamino. Some examples include, but not limited to, N-methylamino, N-ethylamino, N,N-dimethylamino and N,N-diethylamino, and the like.

The term "hydroxyalky" refers to an alkyl group substituted with one or more hydroxyl radicals, wherein the alkyl group are as defined herein. Examples of hydroxyalkyl group include, but are not limited to, hydroxymethyl, 2-hydroxyethyl, 2-hydroxy-1-propyl, 3-hydroxy-1-propyl, 2,3-dihydroxypropyl, and the like.

The term "aminoalkyl" refers to an alkyl group substituted with one or more amino groups, wherein the alkyl is as defined herein. Examples of aminoalkyl group include, but are not limited to, aminomethyl, 2-aminoethyl, 3-amino-1-propyl, 4-amino-1-butyl, and the like.

The term "haloalkyl", "haloalkenyl", "haloalkoxy" or "halogenated alkylamino" respectively refers to an alkyl, alkenyl, alkoxy or alkylamino group, as the case may be, substituted with one or more halogen atoms, and wherein each of the alkyl, alkenyl, alkoxy or alkylamino group is defined as described herein. Examples of such groups include, but are not limited to, trifluoromethyl, 2,2,3,3-tetrafluoropropyl, trifluoromethoxy, trifluoromethyl amino, and the like.

The term "cycloalkyl" refers to a monovalent or multivalent saturated ring having 3 to 12 carbon atoms as a monocyclic, bicyclic, or tricyclic ring system. In some embodiments, the cycloalkyl group contains 7 to 12 carbon atoms. In other embodiments, the cycloalkyl group contains 3 to 8 carbon atoms. In still other embodiments, the cycloalkyl group contains 3 to 6 carbon atoms. The cycloalkyl group may be optionally substituted with one or more substituents disclosed herein.

The term "carbocyclyl", "carbocycle" or "carbocyclic ring" refers to a monovalent or multivalent, nonaromatic, saturated or partially unsaturated ring having 3 to 12 carbon atoms as a monocyclic, bicyclic or tricyclic ring system. A carbobicyclyl group includes a spiro carbobicyclyl group or a fused carbobicyclyl group. Suitable carbocyclyl groups include, but are not limited to, cycloalkyl, cycloalkenyl and cycloalkynyl. In some embodiments, the carbocyclyl group contains 3 to 8 carbon atoms. In other embodiments, the carbocyclyl group contains 3 to 6 carbon atoms. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The carbocyclyl group may be optionally substituted with one or more substituents disclosed herein.

The term "heterocycle", "heterocyclyl", or "heterocyclic ring" as used interchangeably herein refers to a saturated or partially unsaturated monocyclic, bicyclic or tricyclic ring containing 3-12 ring atoms of which at least one ring atom is selected from nitrogen, sulfur or oxygen. Unless otherwise specified, the heterocyclyl group may be carbon or nitrogen linked, and a —CH$_2$— group can be optionally replaced by a —C(=O)— group. In which, the sulfur can be optionally oxygenized to S-oxide, and the nitrogen can be optionally oxygenized to N-oxide.

Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, indolinyl, 1,2,3,4-tetrahydroisoquinolinyl, 1,3-benzodioxolyl and 2-oxa-5-azabicyclo[2.2.1]hept-5-yl. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl and pyrimidinedionyl. Some non-limited examples of heterocyclyl wherein the ring sulfur atom is oxidized is sulfolanyl, 1,1-dioxo-thiomorpholinyl. The heterocyclyl group may be optionally substituted with one or more substituents disclosed herein.

The term "heterocycloalkyl" refers to a monovalent or multivalent saturated ring having 3 to 12 ring atoms as a monocyclic, bicyclic, or tricyclic ring system in which at least one ring atom is selected from nitrogen, sulfur and oxygen. The heterocycloalkyl group may be optionally substituted with one or more substituents disclosed herein.

The term "x-membered", where x is an integer typically describes the number of ring-forming atoms in a moiety where the number of ring-forming atoms is x. For example, piperidinyl is an example of a 6 membered heterocycloalkyl, and decalinyl is an example of a 10 membered cycloalkyl group.

The term "unsaturated" refers to a moiety having one or more units of unsaturation.

The term "heteroatom" refers to one or more of oxygen, sulfur, nitrogen, phosphorus and silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to fluorine (F), chlorine (Cl), bromine (Br) or iodine (I).

The term "azido" or "N$_3$" refers to an azide moiety. This radical may be attached, for example, to a methyl group to form azidomethane (methyl azide, MeN$_3$); or attached to a phenyl group to form phenyl azide (PhN$_3$).

The term "cyano" or "CN" refers to a cyano structure. Such group can be connected with other groups.

The term "nitro" or "NO$_2$" refers to a nitro structure. Such group can be connected with other groups.

The term "aryl" refers to monocyclic, bicyclic and tricyclic carbocyclic ring systems having a total of six to fourteen ring members, or six to twelve ring members, or six to ten ring members, wherein at least one ring in the system is aromatic, and that has a single point or multipoint of attachment to the rest of the molecule. The term "aryl" and "aromatic ring" can be used interchangeably herein. In one embodiment, the aryl group is a carbocyclic ring system having six to ten ring members, wherein at least one ring in the system is aromatic. Examples of aryl ring may include phenyl, naphthyl and anthracene. The aryl group may be optionally and independently substituted with one or more substituents disclosed herein.

The term "heteroaryl" refers to monocyclic, bicyclic and tricyclic carbocyclic ring systems having a total of five to twelve ring members, or five to ten ring members, or five to six ring members, wherein at least one ring in the system is aromatic, and in which at least one ring member is selected from heteroatom, and that has a single point or multipoint of attachment to the rest of the molecule. The term "hetreroaryl" and "heteroaromatic ring" or "heteroaromatic compound" can be used interchangeably herein. The heteroaryl group is optionally substituted with one or more substituents disclosed herein. In one embodiment, a 5-12 membered heteroaryl comprises 1, 2, 3 or 4 heteroatoms independently selected from O, S and N. In other embodiment, a 5-6 membered heteroaryl comprises 1, 2, 3 or 4 heteroatoms independently selected from O, S and N.

Some non-limiting examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, oxadiazolyl (eg 1,2,3-oxadiazolyl, 1,2,5-oxadiazolyl, 1,2,4-oxadiazolyl), oxatriazolyl (1,2,3,4-oxatriazolyl), 2-thiazolyl, 4-thiazolyl, 5-thiazolyl, isothiazolyl, 2-thiadiazolyl (e.g. 1,3,4-thiadiazolyl, 1,2,3-thiadiazolyl, 1,2,5-thiadiazolyl), thiatriazolyl (e.g., 1,2,3,4-thiazoltriazolyl), tetrazolyl (e.g. 2H-1,2,3,4-tetrazolyl, 1H-1,2,3,4-tetrazolyl), triazolyl (e.g. 2H-1,2,3-triazolyl, 1H-1,2,4-triazolyl, 4H-1,2,4-triazolyl), 2-thienyl, 3-thienyl, 1H-pyrazolyl (e.g. 1H-pyrazol-3-yl, 1H-pyrazol-4-yl, 1H-pyrazol-5-yl), 1,2,3-thiadiazolyl, 1,3,4-thiadiazolyl, 1,2,5-thiadiazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g. 3-pyridazinyl, 4-pyridazinyl), 2-pyrazinyl, triazinyl (e.g. 1,3,5-triazine), tetrazinyl (e.g. 1,2,4,5-tetrazinyl, 1,2,3,5-tetrazine); and the following bicycles: benzimidazolyl, benzofuryl, benzothiophenyl, indolyl (e.g., 2-indolyl), purinyl, quinolyl (e.g., 2-quinolyl, 3-quinolyl, 4-quinolyl), isoquinolyl (e.g., 1-isoquinolyl, 3-isoquinolyl or 4-isoquinolyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

As described herein, a bond drawn from a substituent to the center of one ring within a ring system (as shown in Formula b) represents substitution of the substituent at any substitutable or reasonable position on the ring. For example, Formula b represents substitution of the substituent R at any substitutable or reasonable position on the ring C, as shown in Formula c1~Formula c17.

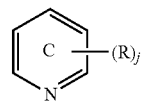

Formula b

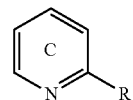

Formula c1

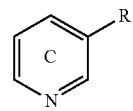

Formula c2

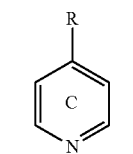

Formula c3

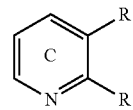

Formula c4

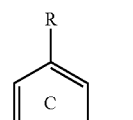

Formula c5

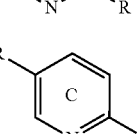

Formula c6

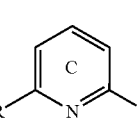

Formula c7

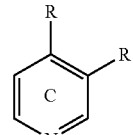

Formula c8

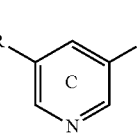

Formula c9

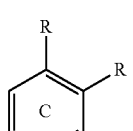

Formula c10

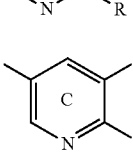

Formula c11

Formula c12
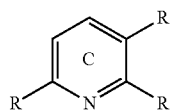

Formula c13
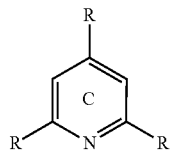

Formula c14
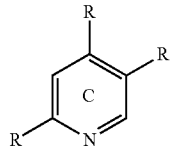

Formula c15
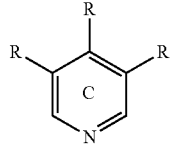

Formula c16
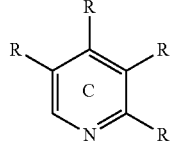

Formula c17
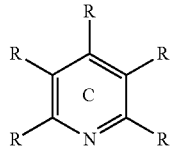

As described herein, the substituents R' connected to the center of the bicyclic ring system (as shown in the formula f) represents substitution of the substituent R' at any substitutable or reasonable position on the ring. For example, the formula f represents that the substituent R' may be mono- or polysubstituted at any substitutable or reasonable position on the ring A, as shown in the formula f1~f15 formula.

Formula f
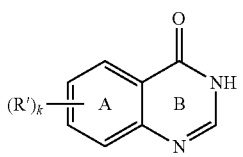

Formula f1
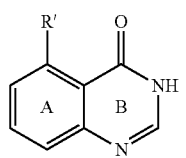

Formula f2
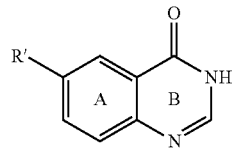

Formula f3
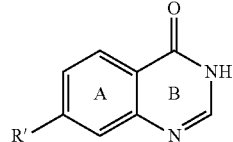

Formula f4
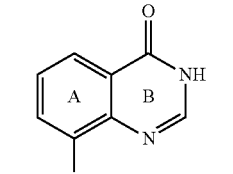

Formula f5
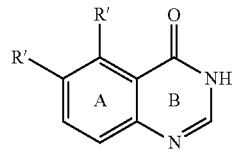

Formula f6
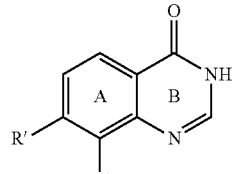

Formula f7
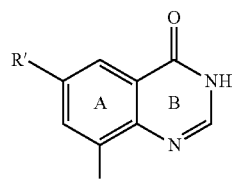

Formula f8
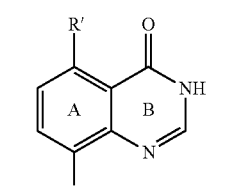

Formula f9
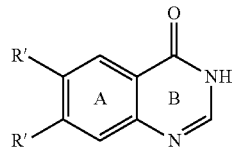

Formula f10
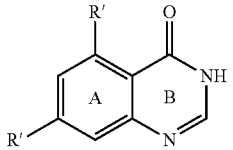

Formula f11
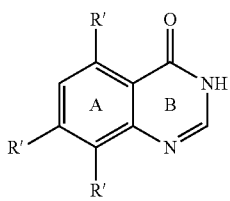

Formula f12
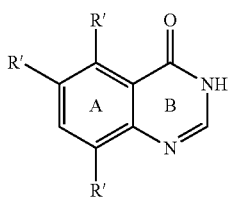

Formula f13
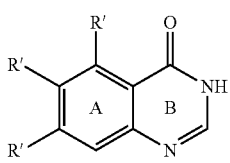

Formula f14
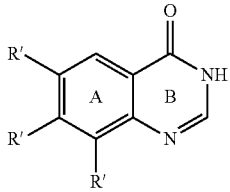

Formula f15
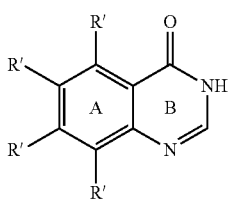

As described herein, a bond connected to the center of one ring within a ring system (as shown in Formula d) represents that a bond in any reasonable and connectable position of the ring can connect to the rest of the molecule. Formula d represents that any reasonable and connectable position of the ring can connect to the rest of the molecule, as shown in formula d1, formula d2 and formula d3.

Formula d
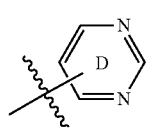

Formula d1
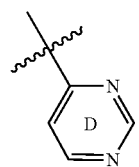

Formula d2
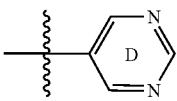

Formula d3
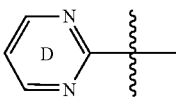

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality.

Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl) ethoxy-methy-1, 2-(p-toluenesulfonyl)-ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic (C$_1$-C$_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345.

A "metabolite" is a product produced through metabolism in the body of a specified compound or salt thereof. The metabolites of a compound may be identified using routine techniques known in the art and their activities can be determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid and ethanolamine. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

As used herein, the term "treat", "treating" or "treatment" of any disease or disorder refers to all processes wherein there may be a slowing, interrupting, arresting, controlling, or stopping of the progression of the disease or disorder, but does not necessarily indicate a total elimination of all the disorder symptoms, as well as the prophylactic therapy of the mentioned conditions, particularly in a patient who is predisposed to such disease or disorder. In some embodiments, "treat", "treating" or "treatment" refers to ameliorating the disease or disorder (i.e., slowing or arresting or reducing the development of the disease or at least one of the clinical symptoms thereof). In other embodiments, "treat", "treating" or "treatment" refers to alleviating or ameliorating at least one physical parameter including those which may not be discernible by the patient. In other embodiments, "treat", "treating" or "treatment" refers to modulating the disease or disorder, either physically, (e.g., stabilization of a discernible symptom), physiologically, (e.g., stabilization of a physical parameter), or both. In other embodiment, "treat", "treating" or "treatment" refers to preventing or delaying the onset or development or progression of the disease or disorder.

As used herein, the term "therapeutically effective amount" or "therapeutically effective dosage" refers to the amount of the compound of the invention which is capable of eliciting biological or medical response (Such as reducing or inhibiting the activity of an enzyme or protein, or ameliorating symptoms, alleviating symptoms, slowing or delaying the development of the disease, or preventing diseases, etc.) of an individual. In one non-limiting embodiment, the term "therapeutically effective amount" refers to, when the compound of the present invention is administered to a subject, an effective amount in the following situations: (1) at least partially alleviating, inhibiting, preventing and/or ameliorating the disease or disorder (i) mediated by the orexin, or (ii) associated with orexin receptor activity, or (iii) characterized by the abnormal activity of orexin receptors; or (2) reducing or inhibiting the activity of orexin receptors; or (3) reducing or inhibiting the expression of orexin receptors. In other embodiment, the term "therapeutically effective amount" refers to, when administering the cell, or organ, or non-cellular biological material, or medium, an effective amount of the compounds of the present invention, which can at least partially reduce or inhibit orexin receptor activity; or at least partially reduce or inhibit the expression of orexin receptors.

As used herein, the terms "administration of" and "administering a" compound should be understood to mean providing a compound of the invention or a prodrug of a compound of the invention to an individual in need thereof. It is recognized that one skilled in the art can treat a patient presently afflicted with neurological and psychiatric disorders or by prophylactically treat a patient afflicted with the disorders with an effective amount of the compound of the present invention.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the dissociation of one or more of the ingredients, or from the other types of reactions or interactions of one or more of the ingredients. Accordingly, the pharmaceutical compositions of the present invention encompass any composition made by mixing a compound of the present invention and a pharmaceutically acceptable carrier.

Description of Compounds of the Invention

The present invention provides substituted quinazolinone compounds, pharmaceutically acceptable salts, pharmaceutical formulations and combinations thereof, which can be used as orexin receptor antagonists, and their potential use in treatment of neurological and/or psychiatric disorders and diseases of the central nervous system in humans, such as depression, anxiety, alcohol into addiction, drug addiction, alcoholism, mania, bipolar disorder, obsessive-compulsive disorder, stress, sleep disorders, insomnia and fatigue resulting from jet lag and insomnia.

In one aspect, provided herein is a compound having Formula (I) or a stereoisomer, an N-oxide, a solvate, a metabolite, a pharmaceutically acceptable salt or a prodrug thereof,

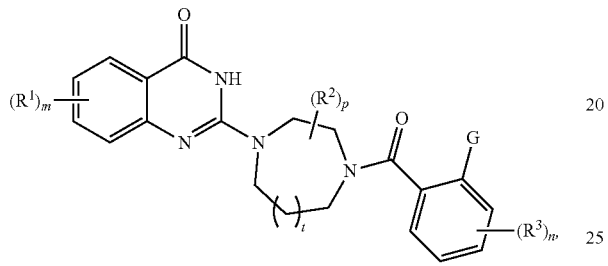
(I)

wherein G, each $R^1$, each $R^2$, each $R^3$, m, n, p and t are as defined herein.

In some embodiments, G is 5- to 6-membered heterocycloalkyl or heteroaryl containing at least one nitrogen, wherein G is further optionally substituted with one or more $R^8$; and wherein each $R^8$ is as defined herein.

In some embodiments, each $R^1$ is independently H, D, F, Cl, Br, I, OH, $NH_2$, $NO_2$, CN, $N_3$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ hydroxyalkyl, $C_{1-6}$ alkylamino, $C_{3-12}$ carbocyclyl, 3- to 12-membered heterocyclyl, $C_{6-10}$ aryl or 5- to 12-membered heteroaryl, wherein each $R^1$ is optionally and independently substituted with one or more $R^8$; and wherein $R^8$ is as defined herein.

In some embodiments, each $R^2$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ hydroxyalkyl or $C_{1-4}$ haloalkyl.

In some embodiments, each $R^3$ is independently H, D, F, Cl, Br, I, OH, $NH_2$, $NO_2$, CN, $N_3$, $C_{1-6}$ alkyl, $C_{2-6}$ alkenyl, $C_{2-6}$ alkynyl, $C_{3-12}$ carbocyclyl, 3- to 12-membered heterocyclyl, $C_{6-10}$ aryl, 5- to 12-membered heteroaryl, $-(CR^4R^{4a})_q$—$OR^7$, $-(CR^4R^{4a})_q$—$NR^5R^6$, $-(CR^4R^{4a})_q$S(=O)$_r$$R^7$, $-(CR^4R^{4a})_q$S(=O)$_2$$NR^5R^6$, $-(CR^4R^{4a})_q$C(=O)$R^7$, $-(CR^4R^{4a})_q$OC(=O)$R^7$, $-(CR^4R^{4a})_q$C(=O) $OR^7$, $-(CR^4R^{4a})_q$—$N(R^5)C(=O)R^7$, $-C(=NR^7)NR^5R^6$, $-N(R^7)C(=O)NR^5R^6$, $-(CR^4R^{4a})_q$—$N(R^5)S(=O)_rR^7$ or $-(CR^4R^{4a})_qC(=O)NR^5R^6$, wherein each $R^3$ is optionally and independently substituted with one or more $R^8$; and wherein each $R^4$, $R^{4a}$, $R^5$, $R^6$, q, r and $R^8$ is as defined herein.

In some embodiments, each $R^4$ and $R^{4a}$ is independently H, D, F, Cl, Br, I, CN, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ haloalkoxy, $C_{1-4}$ haloalkylamino, $C_{3-8}$ carbocyclyl, 3- to 8-membered heterocyclyl, $C_{6-10}$ aryl or 5- to 6-membered heteroaryl;

In some embodiments, each $R^5$, $R^6$ and $R^7$ is independently H, $C_{1-4}$ alkyl, $C_{2-4}$ alkenyl, $C_{2-4}$ alkenyl, $C_{3-8}$ carbocyclyl, ($C_{3-6}$ cycloalkyl)-($C_{1-4}$alkylene)-, 3- to 8-membered heterocyclyl, (3- to 6-membered heterocyclyl)-($C_{1-4}$ alkylene)-, phenyl, ($C_{6-10}$ aryl)-($C_{1-4}$ alkylene)-, 5- to 6-membered heteroaryl, (5- to 6-membered heteroaryl)-($C_{1-4}$ alkylene)-, or $R^5$, $R^6$, and together with the nitrogen atom to which they are attached, independently and optionally form 3- to 6-membered heterocyclyl, wherein $C_{1-4}$ alkyl, $C_{2-4}$ alkenyl, $C_{2-4}$ alkynyl and $C_{3-8}$ carbocyclyl are optionally and independently substituted with one or more substituents selected from D, F, Cl, Br, OH, $NH_2$, CN, $N_3$, $C_{1-4}$ alkyl, $C_{1-4}$ haloalkyl, $C_{1-4}$ alkoxy or $C_{1-4}$ alkylamino.

In some embodiments, each $R^8$ is independently H, D, F, Cl, Br, I, =O, OH, $NH_2$, $NO_2$, CN, $N_3$, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ haloalkyl, $C_{1-4}$ haloalkoxy, $C_{1-4}$ hydroxyalkyl or $C_{1-4}$ haloalkylamino.

In some embodiments, m and n are each independently 0, 1, 2, 3 or 4.

In some embodiments, t is 0 or 1.

In some embodiments, p is 0, 1, 2, 3, 4, or 5.

In some embodiments, each r is independently 0, 1 or 2.

In some embodiments, each q is independently 0, 1, 2, 3 or 4.

In some embodiments, G is:

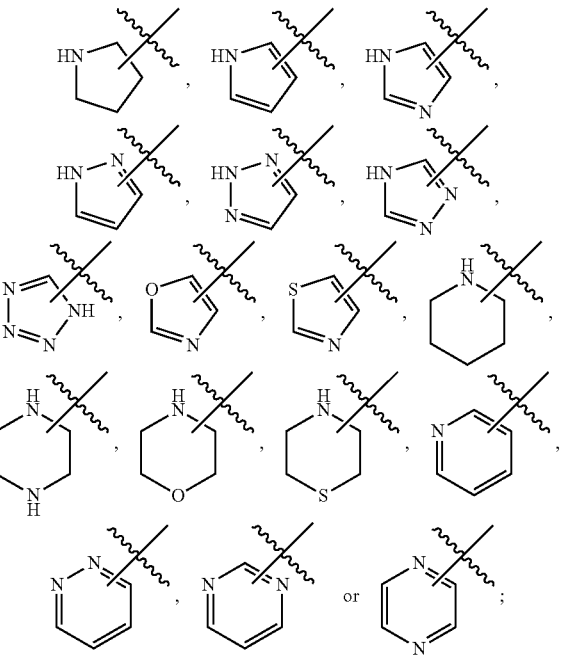

wherein G is optionally substituted with one or more $R^8$; and wherein $R^8$ is as defined herein.

In some embodiments, G is

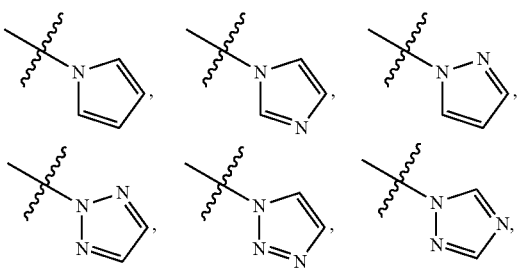

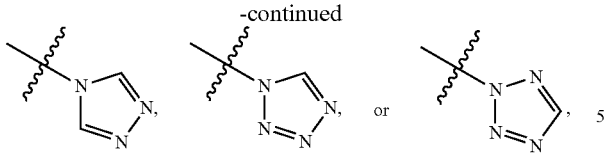

In some embodiments, each $R^1$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ hydroxyalkyl, $C_{1-4}$ alkylamino, $C_{3-8}$ carbocyclyl, 3- to 8-membered heterocyclyl, $C_{6-10}$ aryl or 5- to 6-membered heteroaryl, wherein each $R^1$ is optionally and independently substituted with one or more $R^8$; and Wherein each $R^8$ is as defined herein.

In other embodiments, each $R^1$ is independently H, D, F, Cl, Br, OH, $NH_2$, $NO_2$, CN, methyl, ethyl, n-propyl, isopropyl, n-butyl, isobutyl, vinyl, ethynyl, methoxy, ethoxy, methylamino, ethylamino, hydroxymethyl, hydroxyethyl, trifluoromethyl, cyclopropyl, piperidinyl, piperazinyl, morpholinyl, phenyl, pyrrolyl, imidazolyl, thiazolyl or thienyl.

In some embodiments, each $R^2$ is independently H, F, Cl, OH, $NH_2$, $NO_2$, CN, methyl, ethyl, n-propyl, isopropyl, vinyl, allyl, propargyl, methoxy, ethoxy, methylamino, ethylamino, hydroxymethyl, hydroxyethyl or trifluoromethyl.

In some embodiments, each $R^3$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{3-8}$ carbocyclyl, 3- to 8-membered heterocyclyl, $C_{6-10}$ aryl, 5- to 6-membered heteroaryl, $-(CR^4R^{4a})_q-OR^7$, $-(CR^4R^{4a})_q-NR^5R^6$, $-(CR^4R^{4a})_qS(=O)_rR^7$, $-(CR^4R^{4a})_qS(=O)_2NR^5R^6$, $-(CR^4R^{4a})_qC(=O)R^7$, $-(CR^4R^{4a})_qOC(=O)R^7$, $-(CR^4R^{4a})_qC(=O)OR^7$, $-(CR^4R^{4a})_q-N(R^5)C(=O)R^7$, $-C(=NR^7)NR^5R^6$, $-N(R^7)C(=O)NR^5R^6$, $-(CR^4R^{4a})_q-N(R^5)S(=O)_rR^7$ or $-(CR^4R^{4a})_qC(=O)NR^5R^6$, wherein each $R^3$ is optionally and independently substituted with one or more $R^8$; and wherein each $R^4$, $R^{4a}$, q, r, $R^5$, $R^6$, $R^7$ and $R^8$ is as defined herein.

In other embodiments, each $R^3$ is independently H, D, F, Cl, Br, OH, $NH_2$, $NO_2$, CN, methyl, ethyl, n-propyl, isopropyl, n-butyl, isobutyl, vinyl, ethynyl, methoxy, ethoxy, methylamino, ethylamino, hydroxymethyl, hydroxyethyl, trifluoromethyl, cyclopropyl, piperidinyl, piperazinyl, morpholinyl, phenyl, pyrrolyl, imidazolyl, thiazolyl, thienyl, $-C(=O)NH_2$ or $-COOH$.

In some embodiments, each $R^4$ and $R^{4a}$ is independently H, D, F, Cl, Br, I, CN, methyl, ethyl, isopropyl, vinyl, allyl, ethynyl, propargyl, methoxy, tert-butoxy, methylamino, $-OCF_3$, $-NHCF_3$, cyclopentyl, cyclohexyl, piperidin-1-yl, piperazin-1-yl, pyridin-2-yl, phenyl or naphthyl; and each $R^5$, $R^6$ and $R^7$ is independently H, methyl, ethyl, isopropyl, vinyl, allyl, ethynyl, propargyl, cyclopentyl, cyclohexyl, cyclohexylmethyl, piperidin-1-yl, piperazin-1-yl, imidazol-1-yl, pyridin-4-yl-methyl, phenyl or benzyl, or $R^5$ and $R^6$ together with the nitrogen atom to which they are attached, form pyrrolidinyl, piperazinyl, imidazolidinyl or morpholinyl.

In some embodiments, wherein each $R^8$ is independently H, D, F, Cl, Br, I, $=O$, OH, $NH_2$, $NO_2$, CN, $N_3$, methyl, ethyl, ethynyl, propynyl, methoxy, tert-butoxy, methylamino, trifluoromethyl, trifluoromethoxy, hydroxymethyl or trifluoromethylamino.

In other embodiments, provided herein is the compound having one of the following, or a stereoisomer, an N-oxide, a solvate, a hydrate, a metabolite, a pharmaceutically acceptable salt or a prodrug thereof, but are not limited to:

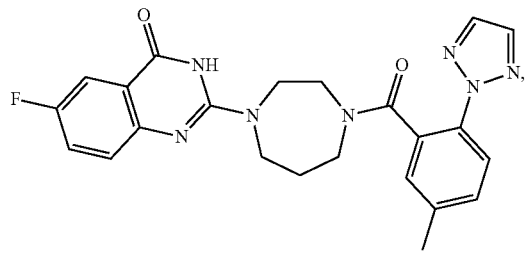

(1)

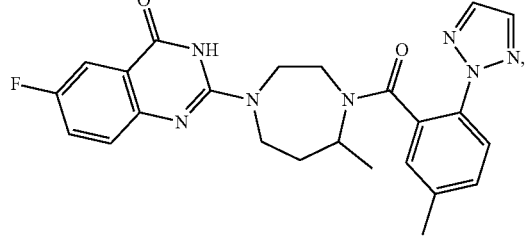

(2)

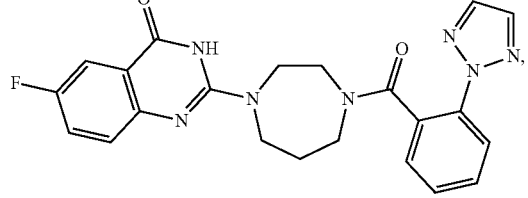

(3)

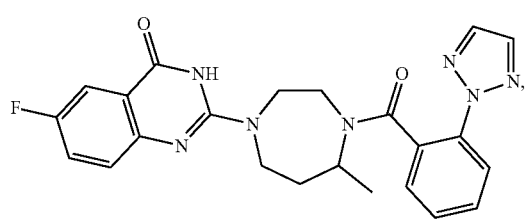

(4)

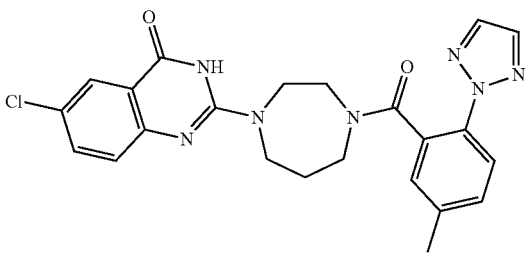

(5)

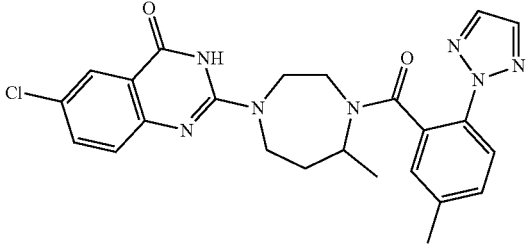

(6)

(7)
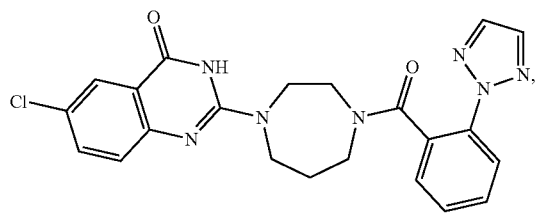
(8)
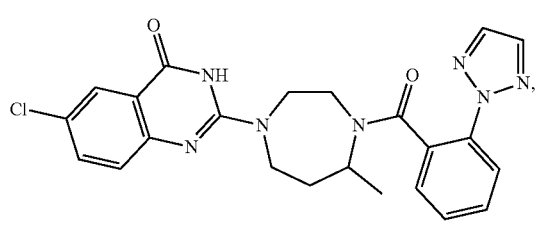
(9)
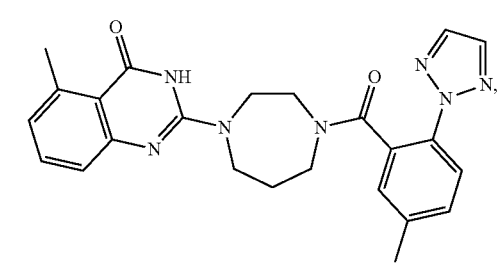
(10)
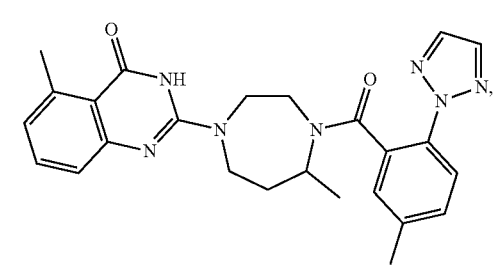
(11)
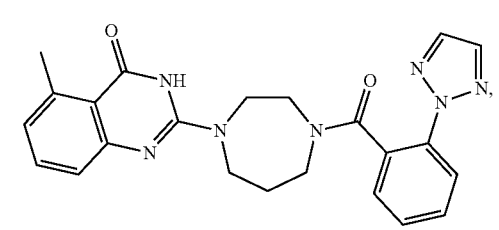
(12)
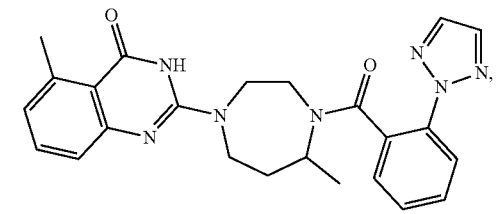
(13)
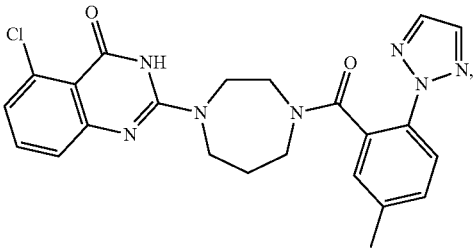
(14)
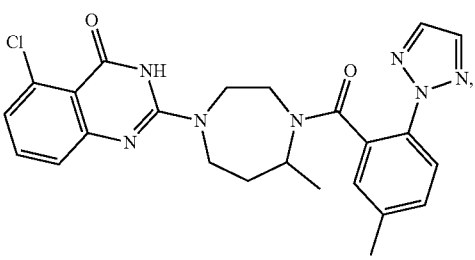
(15)
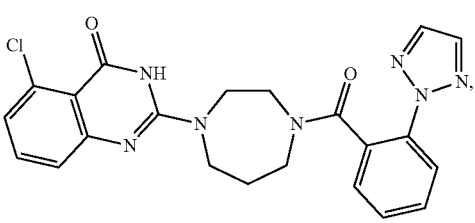
(16)
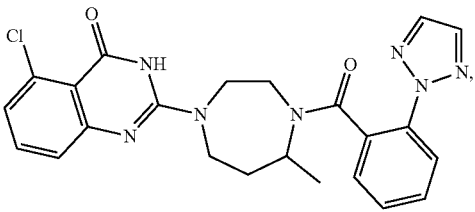
(17)
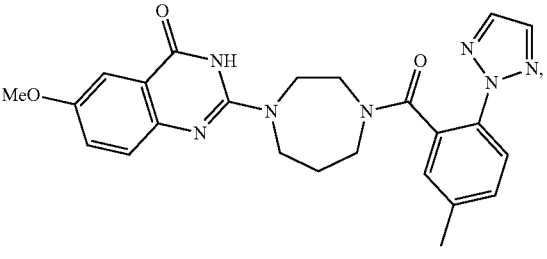
(18)
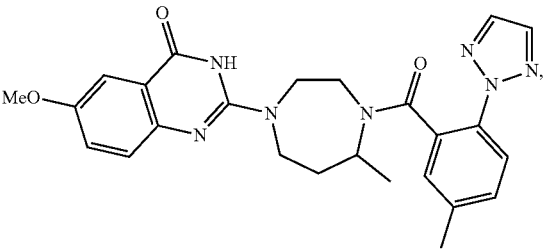

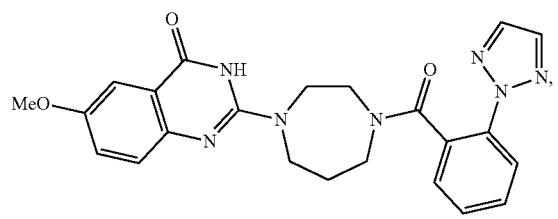
(19)

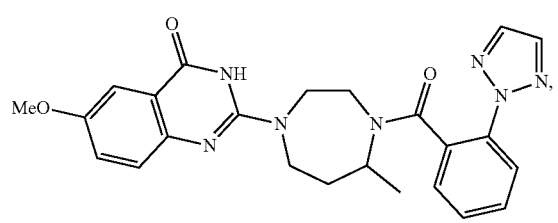
(20)

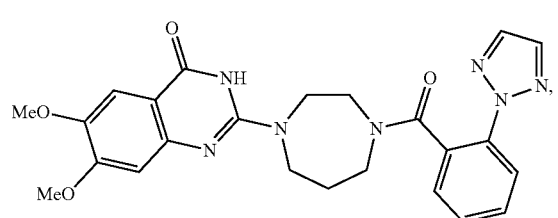
(21)

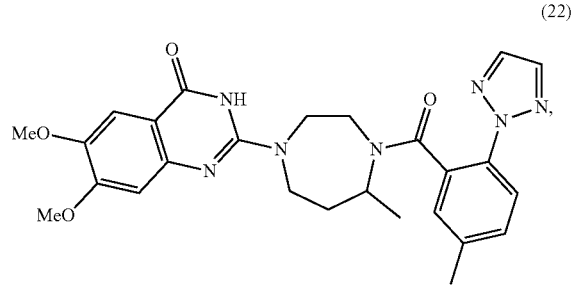
(22)

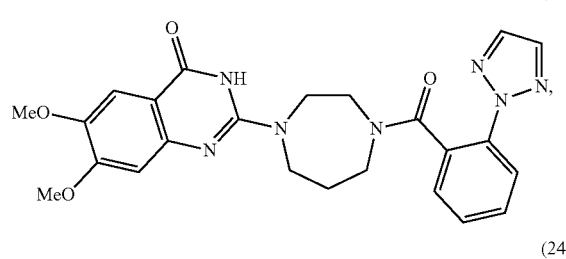
(23)

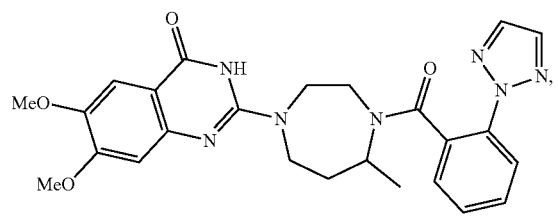
(24)

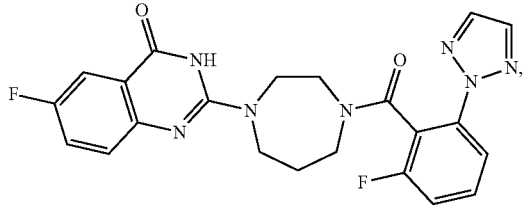
(25)

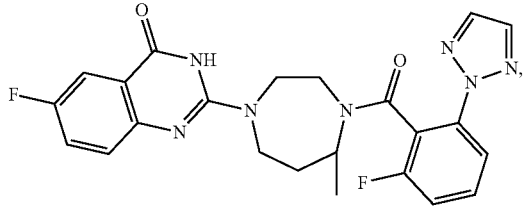
(26)

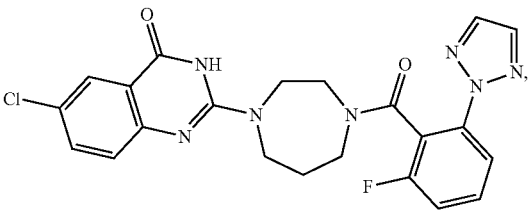
(27)

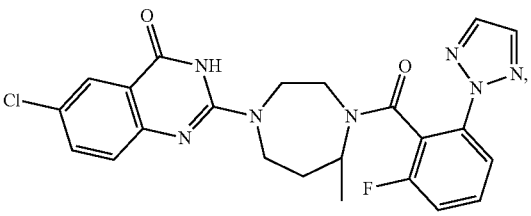
(28)

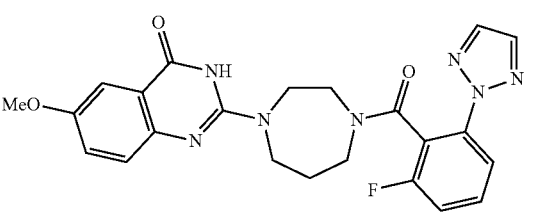
(29)

or

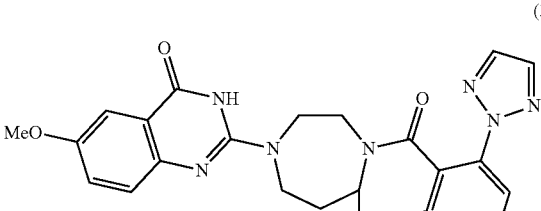
(30)

Unless otherwise specified, a stereoisomer, an N-oxide, a solvate, a hydrate, a metabolite, a pharmaceutically acceptable salt or a prodrug thereof of a compound having Formula (I) are included within the scope of the present invention.

The compounds disclosed herein can be asymmetric or contain a chiral center, and therefore can exist in different stereoisomers. It is intended that all stereoisomeric forms of the compounds having Formula (I) disclosed herein, including, but not limited to, diastereomers, enantiomers, atropisomers and geometric (or conformational) isomers, as well as mixtures thereof such as racemic mixtures, form part of the present invention.

When the stereochemistry of any particular chiral atom is not specified, all stereoisomers of the structure disclosed herein are contemplated within the present invention, and as the compounds disclosed herein are included within the scope of the present invention. When stereochemistry is to denote specific configuration of a solid wedge line or a dashed line indicated, the stereoisomers of the structure is clear and defined.

The compound of Formula (I) can exist in different tautomeric forms, and all of these tautomers are included within the scope of the present invention.

The compound of Formula (I) can exist in the form of a salt. In one embodiment, the salt is a pharmaceutically acceptable salt thereof. The term "pharmaceutically acceptable" refers that a compound or composition must be chemically and/or toxicologically compatible with the other ingredients comprising the formulation and/or treated the mammal.

In other embodiment, the salt is not necessarily a pharmaceutically acceptable salt thereof and can be a compound for the preparation and/or purification the Formula (I), and/or for the separation of the enantiomers of the Formula (I).

Pharmaceutically acceptable acid addition salts can be formed by the interaction of the compound disclosed herein with inorganic acids or organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Pharmaceutically acceptable base addition salts can be formed with inorganic or organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms of the compounds disclosed herein.

Any formula given herein is also intended to represent isotopically unenriched forms as well as isotopically enriched forms of the compounds. Any formula given herein is also intended to represent isotopically unenriched forms as well as isotopically enriched forms of the compounds. Examples of isotopes that can be incorporated into compounds of the invention include isotopes of hydrogen, carbon, nitrogen, oxygen, phosphorous, fluorine, and chlorine, such as $^2$H (deuterium, D), $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. For example, increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000

(90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

In other aspect, provided herein is a preparation of intermediate of the compound of Formula (I).

In other aspect, provided herein is a method of preparing, separating or purifying the compound of Formula (I).

In other aspect, provided herein is a pharmaceutical composition comprising the compound disclosed herein. In some embodiments, provided herein is a pharmaceutical composition further comprising a pharmaceutically acceptable carrier, excipient, adjuvant, solvent or a combination thereof. In other embodiments, the pharmaceutical composition can be liquid, solid, semi-solid, gel or spray.

Pharmaceutical Composition of the Compound of the Invention and Preparations and Administration The present invention provides a pharmaceutical composition comprising compounds of the present invention, e.g., example compounds. According to the specific examples of the present invention, the pharmaceutical composition can further comprise pharmaceutically acceptable excipient, carrier, adjuvant, solvent and a combination thereof.

The present invention provides a method of treating, preventing or ameliorating a disease or disorder, comprising administrating a safe and effective amount of a combination of drugs containing compounds of the invention and one or more therapeutic active agents. Among them, the combination of drugs comprises one or more additional drugs for treatment of neurological and psychiatric disorders and diseases of central nervous system.

Other drugs for treatment of neurological and psychiatric disorders and diseases of central nervous system include, but are not limited to: antidepressants, antianxiety drugs, emotional stabilizer lithium salts drugs, antipsychotics, atypical antipsychotics, antiepileptics, anti-Parkinson's disease drugs, sedative-hypnotic drugs, anti-group amine drugs, GABA receptor agonists and/or GABA reuptake inhibitor drugs, a monoamine oxidase inhibitor drugs, melatonin receptor agonist drugs as well as orexin receptor antagonist drugs or any combination thereof.

The other drugs for prevention or treatment of neurological and psychiatric disorders and diseases of the central nervous system comprise amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate (or Eskalith), buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, perphenazine, midazolam, triazolam, estazolam, diazepam, flurazepam, nitrazepam, clonazepam, temazepam, flunitrazepam, oxazepam, zolpidem, zaleplon, zopiclone, eszopiclone, indiplon, tiagabine, gaboxadol, clomipramine, doxepin, chloral hydrate, haloperidol, chlorpromazine, carbamazepine, promethazine, lorazepam, hydroxyzine, aspirin, diphenhydramine, chlorpheniramine, lendormin, ramelteon, tasimelteon, agomelatine, mianserin, femoxetine, nabilone, doxepin, gabapentin, chlordiazepoxide, suvorexant, Xuezang Guben or any combination thereof.

The amount of the compound of the pharmaceutical composition disclosed herein refers to an amount which can be effectively detected to antagonisting orexin receptors of biology sample and patient. The dosage of active ingredient in the compositions of this invention may be varied, however, it is necessary that the amount of the active ingredient be such that a suitable dosage form is obtained. The active ingredient may be administered to patients (animals or human) in need of such treatment in dosage that will provide optimal pharmaceutical efficacy. The selected dosage upon the desired therapeutic effect, on the route of administration, and on the duration of the treatment. The dosage will vary from patient to patient depending upon the nature and severity of disease, the patient's weight, special diet then being followed by a patient, concurrent medication, and other factors which those skilled in the art will recognize. The dosage range will generally be about 0.5 mg to 1.0 g per patient per day which may be administered in single or multiple doses. In one embodiment, the dosage range will be about 0.5 mg to 500 mg per patient per day; in anther embodiment about 0.5 mg to 200 mg per patient per day; and in yet another embodiment about 5 mg to 50 mg per patient per day.

It will also be appreciated that certain of the compounds of the present invention can exist in free form for treatment, or where appropriate, as a pharmaceutically acceptable derivative or a prodrug thereof. A pharmaceutically acceptable derivative includes pharmaceutically acceptable salts, esters, salts of such esters, or any other adduct or derivative which upon administration to a patient in need thereof is capable of providing, directly or indirectly, a compound as otherwise described herein, or a metabolite or residue thereof.

The pharmaceutical compositions of the invention may be prepared and packaged in bulk form wherein a safe and effective amount of a compound of Formula (I) disclosed herein can be extracted and then given to the patient, such as with powders or syrups. Generally, dosage levels of between 0.0001 to 10 mg/kg of body weight daily are administered to the patient to obtain effective antagonism of orexin receptors. Alternatively, the pharmaceutical compositions of the invention may be prepared and packaged in unit dosage form wherein each physically discrete unit contains a safe and effective amount of a compound of Formula (I) disclosed herein. When prepared in unit dosage form, the pharmaceutical compositions of the invention commonly contain from about 0.5 mg to 1 g, or 1 mg to 700 mg, or 5 mg to 100 mg, of the compound of the invention.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared at for example environment temperature and under barometric pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In one embodiment, the compounds disclosed herein can be prepared to oral. In the other embodiment, the compounds disclosed herein can be prepared to inhalation. In the still other embodiment, the compounds disclosed herein can be prepared to nasal administration. In the yet other embodiment, the compounds disclosed herein can be prepared to transdermal administration. In the still yet other embodiments, the compounds disclosed herein can be prepared to topical administration.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Miccellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a $D_{50}$ value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

Uses of the Compounds and Compositions of the Invention

Compounds or pharmaceutical compositions of the invention disclosed herein can be used in the manufacture of a medicament for treating, preventing, ameliorating, controlling or mitigating a neurological and psychiatric disorder or disease of central nervous system in a mammal or a patient, as well as other medicaments for antagonizing an orexin receptor, and the compounds of this invention have fewer toxic side-effect, for example, the compounds of this invention embodiments have no or weak inhibitory activity against hERG channel, which prompts less risk to cause QT interval elongation.

Specifically, the amount of the compound of compositions of the present invention can effectively and detectably antagonize an orexin receptor. The compounds or pharmaceutical compositions of the invention may be used for preventing, treating or alleviating orexin receptor-related diseases, wherein the orexin receptor-related diseases include sleep disorders, depression, anxiety, panic disorders, obsessive-compulsive disorders, emotional neuropathy, depression neuropathy, anxiety neuropathy, mood disorders, panic attack disorders, behavioral disorders, mood disorders, past-traumatic stress disorders, sexual dysfunction, psychoses, schizophrenia, manic depression, insanity, dementia, drug dependence, addiction, cognitive disorders, Alzheimer's disease, Parkinson's disease, dyskinesia, eating disorders, headache, migraine, pain, digestive disorders, epilepsy, inflammation, cardiovascular diseases, diabetes, metabolic diseases, immune related diseases, endocrine-related diseases or hypertension.

The compounds of this invention can be used as drugs for preventing or treating neurological and psychiatric disorders and diseases of central nervous system such as depression, an anxiety disorder, a seasonal affective disorder, mania, a bipolar disorder, obsessive-compulsive disorder, insomnia and fatigue resulting from jet lag, mental schizophrenia, seizure, panic attack, melancholia, alcohol addiction, drug addiction, alcoholism, substance abuse, drug addiction withdrawal symptoms, insomnia, a psychotic disorder, epilepsy, somnipathy, sleep disorder, sleep apnea syndrome, a mandatory eating disorder, fibromyalgia, stress, obesity, Parkinson's disease, a cognitive disorder, a memory disorder, premenstrual tension syndrome, a migraine headache, memory loss, Alzheimer silent disease or a disorder related to normal or pathological aging.

Compounds or compositions of the present invention may be applied, but not limited to, an effective amount of a compound or composition was administered to a patient to prevent, treat or mitigate a neurological and psychiatric disorder or disease of central nervous system of a mammal or a patient. The neurological and psychiatric disorder or disease of central nervous system of human further includes, but are not limited to, depression, an anxiety disorder, a seasonal affective disorder, mania, a bipolar disorder, obsessive-compulsive disorder, insomnia and fatigue resulting from jet lag, mental schizophrenia, seizure, panic attack, melancholia, alcohol addiction, drug addiction, alcoholism, substance abuse, drug addiction withdrawal symptoms, insomnia, a psychotic disorder, epilepsy, somnipathy, sleep disorder, sleep apnea syndrome, a mandatory eating disorder, fibromyalgia, stress, obesity, Parkinson's disease, a cognitive disorder, a memory disorder, premenstrual tension syndrome, a migraine headache, memory loss, Alzheimer silent disease or a disorder related to normal or pathological aging.

Besides being useful for human treatment, these compounds and pharmaceutical compositions are also useful for veterinary treatment of animals such as a companion animal, an exotic animal and a mammal in the farm. In other embodiments, the animals disclosed herein include a horse, a dog, and a cat. As used herein, the compounds disclosed herein include the pharmaceutically acceptable derivatives thereof.

Therapies

In one embodiment, the therapies disclosed herein comprise administrating a safe and effective amount of the compound of the invention or the pharmaceutical composition containing the compound of the invention to patients in need. Each example disclosed herein comprises the method of treating the diseases above comprising administrating a safe and effective amount of the compound of the invention or the pharmaceutical composition containing the compound of the invention to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally or parenterally, advantageously intravenously, e.g., as a suspension or in aqueous solution.

In one embodiment, a therapeutically effective dosage of the compound disclosed herein from about 0.1 mg to about 2,000 mg per day. The pharmaceutical compositions should provide a dosage of from about 0.1 mg to about 2000 mg of the compound. In a special embodiment, pharmaceutical dosage unit forms are prepared to provide from about 1 mg to about 2,000 mg, about 10 mg to about 1,000 mg, about 20 mg to about 500 mg, or about 25 mg to about 250 mg of the active ingredient or a combination of essential ingredients per dosage unit form. In a special embodiment, pharmaceutical dosage unit forms are prepared to provide about 10 mg, 20 mg, 25 mg, 50 mg, 100 mg, 250 mg, 500 mg, 1000 mg or 2000 mg of the active ingredient.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

General Synthetic Procedures

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (I) above, except where further noted.

The following non-limiting schemes and examples are presented to further exemplify the invention.

Professionals skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Chemical Reagent Factory, Guangzhou Reagent Chemical Factory, Tianjin YuYu Fine Chemical Ltd., Tianjin Fuchen Chemical Reagent Factory, Wuhan XinHuaYuanm Technology Development Co. Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAc and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

1H NMR spectra were recorded with a Bruker 400 MHz or 600 MHz spectrometer using $CDCl_3$, DMSO-$d_6$, $CD_3OD$ or $d_6$-acetone as solutions (reported in ppm), and using TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, were reported in Hertz (Hz).

Low resolution mass spectrum (MS) measurement condition data is: Agilent 6120 Quadrupole HPLC-M (column type: Zorbax SB-$C_{18}$, 2.1×30 mm, 3.5 micron, 6 min, flow rate 0.6 mL/min. The mobile phases consisted of a combination of A (0.1% formic acid in $CH_3CN$) and B (0.1% formic acid in $H_2O$) in gradient mode (5% to 95%), and an ESI source was used, the peak of HPLC was recorded with UV-Vis detection at 210/254 nm.

Compound purity was measured by High Performance Liquid Chromatography (HPLC) using Agilent 1260 HPLC (column Model: Agilent zorbax Eclipse Plus C18) and DAD detector. Compound purity was calculated with area normalization method.

The following abbreviations are used throughout the specification:

$CDCl_3$ deuterochloroform
$CD_3OD$ methanol-D4
DMSO-$d_6$ deuterated dimethylsulfoxide
g gram
mL, ml milliliter Typical synthetic procedures for preparing the compounds of the present invention disclosed are shown in the following synthetic scheme. Unless otherwise specified, each $R^1$, $R^2$, $R^3$, m, n and p is as defined herein.

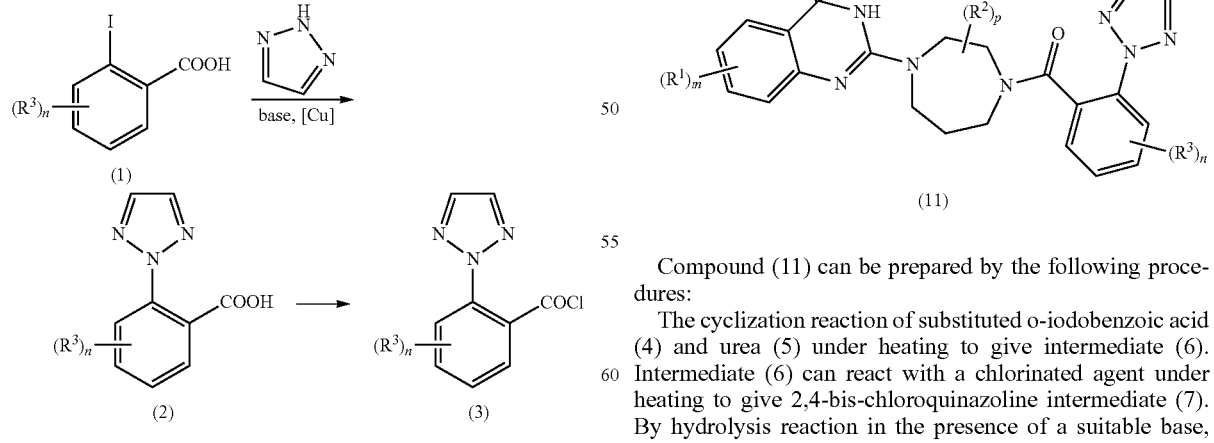

Intermediate (3) can be prepared by the synthetic procedure illustrated in Scheme of intermediate. Substituted o-iodobenzoic acid (1) can react with 2H-1,2,3-triazole in the presence of catalyst [Cu] and a suitable base under heating to give intermediate (2). Compound (2) can react with a chlorinated agent under heating to give intermediate (3).

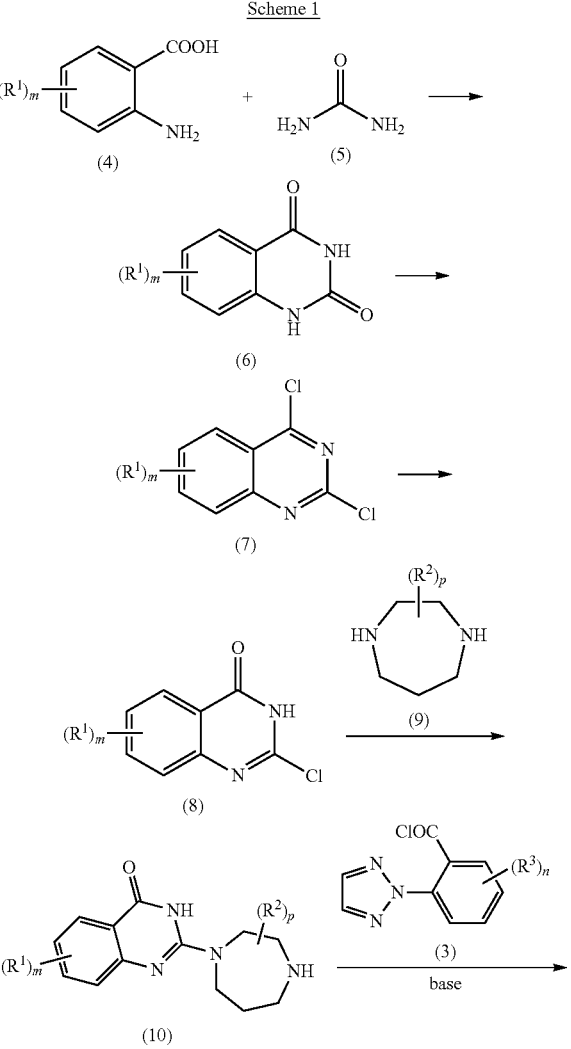

Compound (11) can be prepared by the following procedures:

The cyclization reaction of substituted o-iodobenzoic acid (4) and urea (5) under heating to give intermediate (6). Intermediate (6) can react with a chlorinated agent under heating to give 2,4-bis-chloroquinazoline intermediate (7). By hydrolysis reaction in the presence of a suitable base, intermediate (7) can be converted to intermediate (8). Compound (8) can further react with 1,4-diazepane substituted with different $R^2$ (9) under heating to give compound (10). Compound (10) can react with the intermediate (3) in the presence of a suitable base to give compound (11).

Example structures of the present invention contain a structure of 1,4-diazepan, the hindered rotation of which structure leads that compounds of examples show a plurality of conformations (Cox, C. D.; McGaughey, G B. et al., Conformational analysis of N,N-disubstituted-1,4-diazepane orexin receptor antagonists and implications for receptor binding. *Bioorg. Med. Chem. Lett.* 2009, 19, 2997-3001.), the signal peak width of NMR spectrum of which are overlapping, and it is not easy to analyze coupling constant. In order to facilitate the structures of compounds of examples comparative between each other, the implementation of embodiments of the invention will not represent the NMR signal in numerical form, but to provide specific NMR spectra and purity data of compounds of examples.

The following examples and description are provided to further illustrate compounds, pharmaceutical compositions of the present invention and their use.

BRIEF DESCRIPTION OF THE DRAWINGS

These and other aspects and advantages of embodiments of the present disclosure will become apparent and more readily appreciated from the following descriptions made with reference the accompanying drawings, in which.

EXAMPLES

Figure 1:
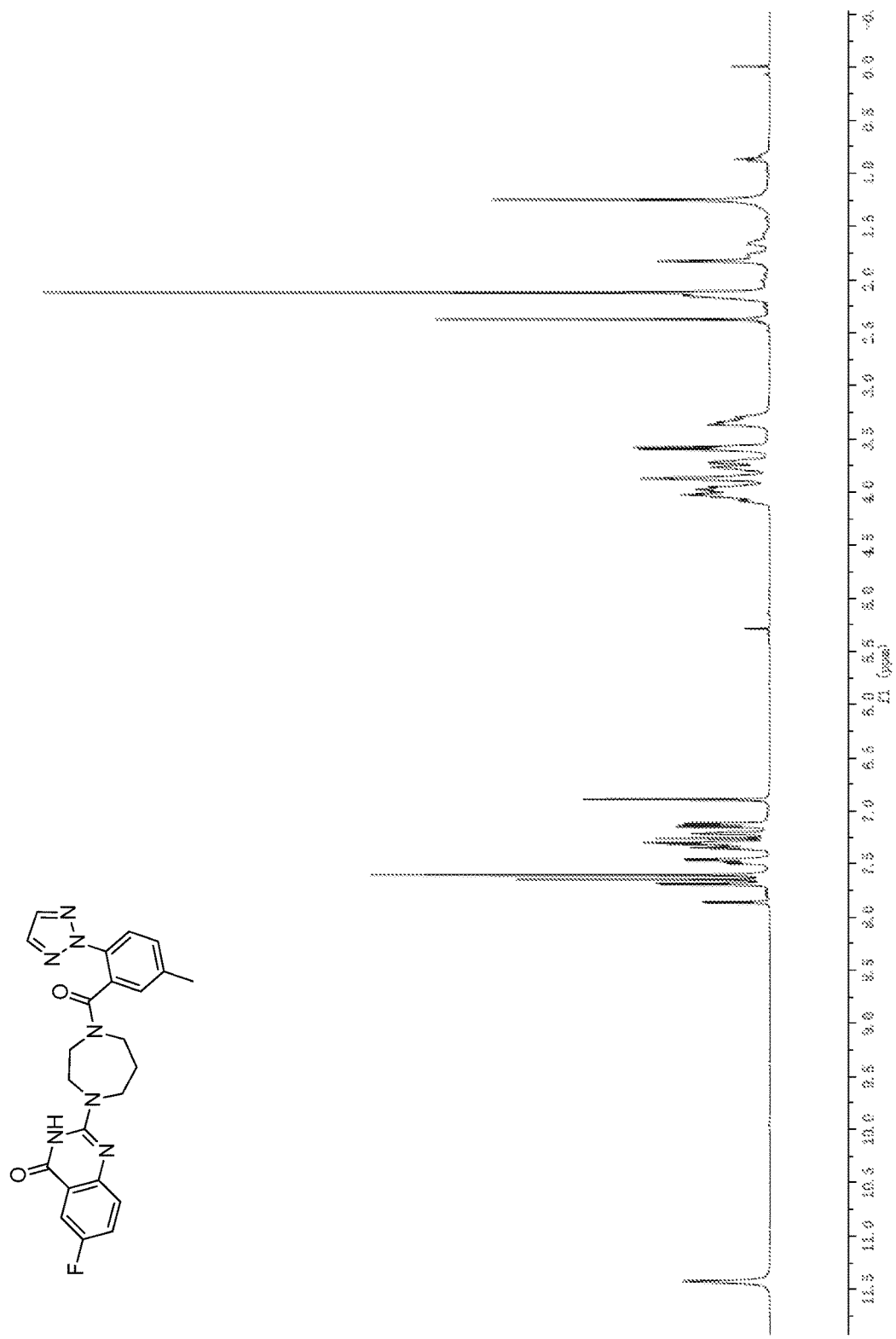
FIG. 1 shows the $^1$H NMR (CDCl$_3$, 600 MHz) spectrum of Example 1 of the invention.

It should be noted that embodiments of the present invention described in detail below are exemplary for explaining the present invention only, and not be construed as limiting the present invention. Examples without a specific technology or condition can be implemented according to technology or condition in the documentation of the art or according to the product instructions. The reagents or instruments without manufacturers are available through conventional purchase.

Example 1: Synthesis of 6-fluoro-2-(4-(5-methyl-2-(2H-1,2,3-triazol-2-yl)benzoyl)-1,4-diazepan-1-yl)quinazolin-4(3H)-one

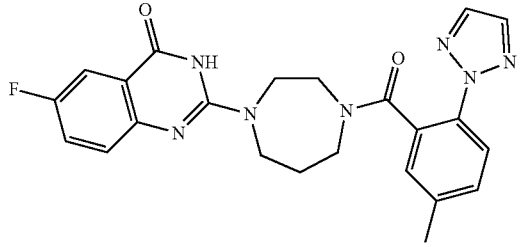 [SMILES: Cc1ccc(-n2nccn2)c(C(=O)N2CCCN(c3nc4ccc(F)cc4c(=O)[nH]3)CC2)c1]

Step 1) Synthesis of 6-fluoroquinazolin-2,4-(1H,3H)-dione

Urea (29.0 g, 482.9 mmol) and 2-amino-5-fluorobenzoic acid (5.00 g, 32.20 mmol) were added sequentially to a 200 mL of sealed tube. The mixture was gradually warmed to 160° C. under vigorous stirring. After stirring for 4 h, the mixture was heated to 180° C., and continued to react for 4 h. Then the mixture was cooled gradually to rt, and water (150 mL) was added. The resulting mixture was stirred for 1 h at rt, and filtered. The residue was washed with water until the filtrate was colorless, and then washed with acetone (20 mL) and methanol (70 mL) sequentially. The resulting residue was dried to give the title compound (as a brick red solid, 5.04 g, 87%).

MS (ESI, neg. ion) m/z: 179.1 [M−H]$^-$; and
$^1$H NMR (DMSO-d$_6$, 600 MHz) δ (ppm): 11.29 (s, 2H), 7.57 (dd, J=8.4 Hz, 2.7 Hz, 1H), 7.53 (td, J=8.7 Hz, 2.8 Hz, 1H), 7.19 (dd, J=8.8 Hz, 4.3 Hz, 1H).

Step 2) Synthesis of 2,4-dichloro-6-fluoroquinazoline

Phosphorus pentachloride (12.5 g, 60.0 mmol) and phosphorus oxychloride (46.00 mL, 502.50 mmol) were sequentially added to a 250 mL of a single jar, and 6-fluoroquinazolin-2,4-(1H,3H)-dione (3.60 g, 20.00 mmol) was slowly added under stirring. The reaction mixture was gradually warmed to reflux and reacted. After the reaction of 9 h, the reaction mixture was cooled, the solvent was removed in vacuo, and the residue was slowly poured into a mixture of ice and water (400 mL). After being stirred for 0.5 h, the resulting mixture was extracted with dichloromethane (250 mL×3). The combined organic layers were concentrated. The residue was purified by silica gel column chromatography eluted with (petroleum ether/ethyl acetate (v/v)=30/1) to give the title compound (as a white solid, 3.74 g, 86%).

MS (ESI, pos. ion) m/z: 216.9 [M+H]$^+$; and
$^1$H NMR (CDCl$_3$, 400 MHz) δ (ppm): 8.03 (dd, J=9.2 Hz, 4.9 Hz, 1H), 7.86 (dd, J=8.1 Hz, 2.7 Hz, 1H), 7.79~7.73 (m, 1H).

Step 3) Synthesis of 2-chloro-6-fluoroquinazolin-4(3H)-one 2,4-Dichloro-6-fluoroquinazoline (0.21 g, 0.97 mmol) was dissolved in tetrahydrofuran (1 mL) in a 50 mL of single neck flask. Then aqueous sodium hydroxide (1 M, 8 mL) was added when the 2,4-dichloro-6-fluoroquinazoline was completely dissolved, and the resulting mixture was reacted for 12 h at r.t. under nitrogen. The mixture was adjusted to pH 5-6 with glacial acetic acid. The resulting mixture was extracted with ethyl acetate (10 mL×2). The combined ethyl acetate layers were concentrated. The residue was purified by column chromatography on silica gel eluted with (petroleum ether/ethyl acetate (v/v)=4/1) to give the title compound (as a white solid, 0.16 g, 83%).

MS (ESI, pos. ion) m/z: 199.1 [M+H]$^+$; and $^1$H NMR (CDCl$_3$, 400 MHz) δ (ppm): 10.93 (s, 1H), 7.92 (dd, J=8.0 Hz, 3.0 Hz, 1H), 7.71 (dd, J=9.0 Hz, 4.8 Hz, 1H), 7.53 (td, J=8.4 Hz, 3.0 Hz, 1H).

Step 4) Synthesis of 2-(1,4-diazepan-1-yl)-6-fluoro-quinazolin-4(3H)-one 1,4-Diazepane (0.11 g, 1.10 mmol) was dissolved in absolute ethanol (10 mL) in a 100 mL of single-neck flask, and a solution of 2-chloro-6-fluoroquinazolin-4(3H)-one (0.20 g, 1.00 mmol) in absolute ethanol (10 mL) was added slowly dropwise under nitrogen. The reaction mixture was gradually warmed to reflux and reacted for 6 h. The reaction mixture was concentrated. The residue was purified by column chromatography on silica gel eluted with (dichloromethane/methanol (v/v)=10/1) to give the title compound (as a white solid, 0.23 g, 88%).

MS (ESI, pos. ion) m/z: 263.4 [M+H]$^+$; and $^1$H NMR (DMSO-d$_6$, 400 MHz) δ (ppm): 7.56 (dd, J=8.7 Hz, 3.0 Hz, 1H), 7.49~7.40 (m, 2H), 3.93~3.89 (m, 2H), 3.76 (t, J=6.0 Hz, 2H), 3.19~3.16 (m, 2H), 3.10~3.06 (m, 2H), 2.04~1.98 (m, 2H).

Step 5) Synthesis of 5-methyl-2-(2H-1,2,3-triazole-2-yl)benzoic acid 1,2,3-Triazole (3.45 g, 50 mmol), 2-iodo-5-methylbenzoic acid (5.24 g, 20 mmol), cesium carbonate (11.72 g, 36 mmol), trans-N,N'-dimethyl-1,2-cyclohexanediamine (0.51 g, 3.60 mmol), cuprous iodide (0.38 g, 2 mmol) and N,N-dimethylformamide (30 mL) were added sequentially to a 100 mL of single-necked round-bottomed flask under nitrogen, and the mixture was warmed gradually to 100° C. and reacted for 4 h. The reaction mixture was cooled, diluted with water, and extracted with ethyl acetate (200 mL×2). The aqueous layer was acidified to pH 1-2 with concentrated hydrochloric acid, and the resulting mixture was extracted with ethyl acetate (200 mL×2). The combined organic layers were dried over anhydrous sodium sulfate, and concentrated. The residue was purified by column chromatography on silica gel eluted with (dichloromethane/methanol (v/v)=50/1) to give the title compound (as a yellow solid, 2.76 g, 68%).

MS (ESI, neg. ion) m/z: 202.1 [M–H]$^-$; and $^1$H NMR (CD$_3$OD, 600 MHz) δ (ppm): 7.88 (s, 2H), 7.66 (d, 1H), 7.59 (d, J=8.2 Hz, 1H), 7.50~7.48 (dd, J=8.1 Hz, 1.1 Hz, 1H), 2.45 (s, 3H). $^{13}$C NMR (CD$_3$OD, 151 MHz) δ (ppm): 169.8, 140.7, 137.5, 136.7, 133.5, 131.5, 129.3, 126.0, 21.0.

Step 6) Synthesis of 5-methyl-2-(2H-1,2,3-triazole-2-yl)benzoyl chloride

5-Methyl-2-(2H-1,2,3-triazole-2-yl)benzoic acid (2.03 g, 10 mmol) was dissolved in anhydrous dichloromethane (20 mL) in a 100 mL of single-necked round-bottomed flask, and thionyl chloride (15 mL, 200 mmol) and pyridine (0.15 mL, 2 mmol) were added slowly. The reaction mixture was gradually warmed to reflux and reacted for 3 h. The solvent was removed slowly in vacuo. The resulting product was used directly in the next reaction.

Step 7) Synthesis of 6-fluoro-2-(4-(5-methyl-2-(2H-1,2,3-triazol-2-yl)benzoyl)-1,4-diazepan-1-yl)qui-nazolin-4(3H)-one 2-(1,4-Diazepan-1-yl)-6-fluoroquinazolin-4(3H)-one (0.16 g, 0.60 mmol) was dissolved in anhydrous dichloromethane (10 mL) in a 50 mL of single-necked bottle, and then triethylamine (0.33 mL, 2.4 mmol) and a solution of 5-methyl-2-(2H-1,2,3-triazole-2-yl)benzoyl chloride (0.16 g, 0.72 mmol) in dichloromethane (10 mL) were added slowly and sequentially under an ice-water bath. The mixture was stirred for 10 minutes under an ice-water bath, the ice-water bath was removed, and the mixture was reacted for 12 h at rt. Dichloromethane (30 mL) was added to the mixture, and the resulting mixture was washed sequentially with water (20 mL) and saturated brine (20 mL). The organic layer was concentrated. The residue was purified by column chromatography on silica gel eluted with (dichloromethane/methanol (v/v)=50/1) to give the title compound (as a white solid, 0.15 g, 56%).

$^1$H NMR (CDCl$_3$, 600 MHz) spectrum is shown in FIG. 1;

MS (ESI, pos. ion) m/z: 448.3 [M+H]$^+$; and

HPLC: 98.7%.

Example 2: Synthesis of 6-fluoro-2-(5-methyl-4-(5-methyl-2-(2H-1,2,3-triazol-2-yl)benzoyl)-1,4-diaz-epan-1-yl)quinazolin-4(3H)-one

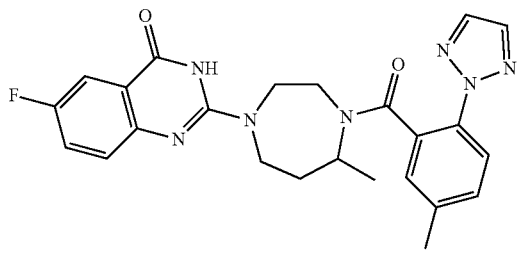 [SMILES: Cc1ccc(-n2nccn2)c(C(=O)N2CCN(c3nc4ccc(F)cc4c(=O)[nH]3)CCC2C)c1]

Step 1) Synthesis of 6-fluoro-2-(5-methyl-1,4-diaz-epan-1-yl)quinazolin-4(3H)-one 5-Methyl-1,4-diazepane (0.12 g, 1.05 mmol) was reacted with 2-chloro-6-fluoroquinazolin-4(3H)-one (0.20 g, 1.00 mmol) in absolute ethanol (20 mL) according to the procedure as described in step 4 of example 1, and the crude product was purified by column chromatography on silica gel eluted with (dichloromethane/methanol (v/v)=10/1) to give the title compound (as a white solid, 0.26 g, 95%).

MS (ESI, pos. ion) m/z: 277.2 [M+H]$^+$; and $^1$H NMR (DMSO-d$_6$, 400 MHz) δ (ppm): 7.55 (dd, J=8.7 Hz, 2.8 Hz, 1H), 7.48~7.38 (m, 2H), 3.96~3.86 (m, 2H), 3.81~3.73 (m, 1H), 3.64~3.56 (m, 1H), 3.30~3.24 (m, 1H), 3.17~3.10 (m, 1H), 3.08~3.01 (m, 1H), 2.00~1.93 (m, 1H), 1.83~1.76 (m, 1H), 1.20 (d, J=6.5 Hz, 3H).

Step 2) Synthesis of 6-fluoro-2-(5-methyl-4-(5-methyl-2-(2H-1,2,3-triazol-2-yl)benzoyl)-1,4-diazepan-1-yl)quinazolin-4(3H)-one 6-Fluoro-2-(5-methyl-1,4-diazepan-1-yl)quinazolin-4(3H)-one (0.17 g, 0.60 mmol) was reacted with 5-methyl-2-(2H-1,2,3-triazole-2-yl)benzoyl chloride (0.16 g, 0.72 mmol) and triethylamine (0.33 mL, 2.40 mmol) in anhydrous dichloromethane (20 mL) according to the procedure as described in step 7 of example 1, and the crude product was purified by silica gel chromatography (dichloromethane/methanol (v/v)=50/1) to give the title compound (as a white solid, 0.16 g, 59%).

Figure 2:
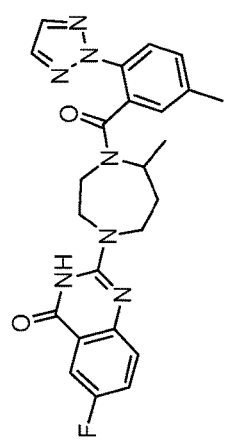
FIG. 2 shows the $^1$H NMR (CDCl$_3$, 600 MHz) spectrum of Example 2 of the invention.
Figure 2:
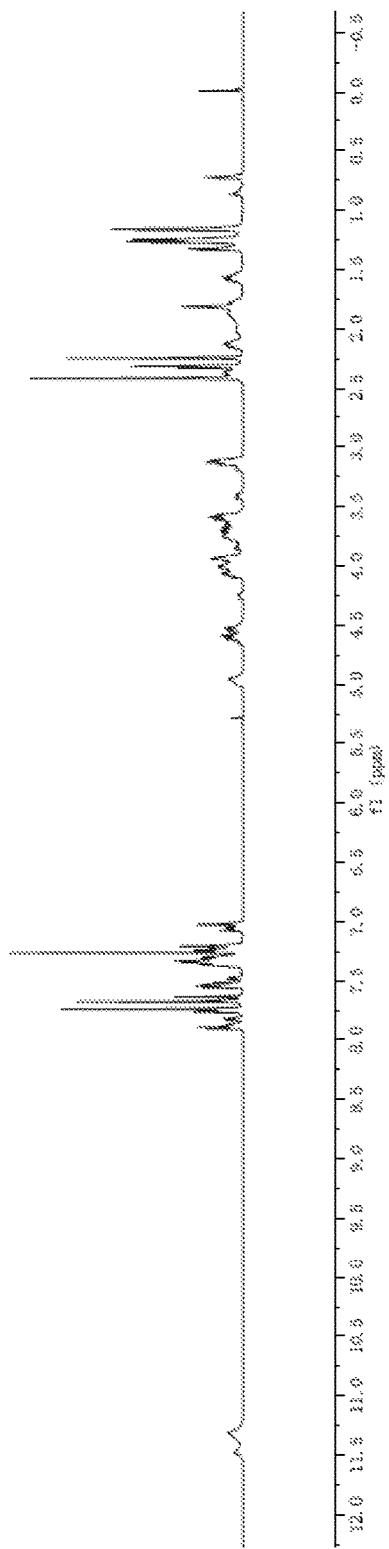

$^1$H NMR (CDCl$_3$, 600 MHz) spectrum is shown in FIG. 2;

MS (ESI, pos. ion) m/z: 461.9 [M+H]$^+$; and
HPLC: 99.5%.

Example 3: Synthesis of 2-(4-(2-(2H-1,2,3-triazol-2-yl)benzoyl)-1,4-diazepan-1-yl)-6-fluoroquinazolin-4(3H)-one

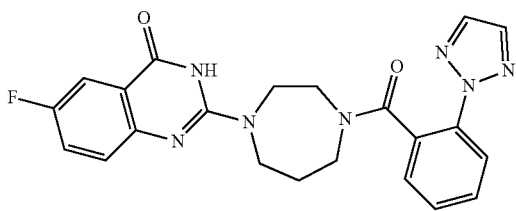 [SMILES: O=C(c1ccccc1-n1nccn1)N1CCCN(c2nc3ccc(F)cc3c(=O)[nH]2)CC1]

Step 1) Synthesis of 2-(2H-1,2,3-triazole-2-yl)benzoic acid 1,2,3-Triazole (0.70 g, 10.08 mmol) was reacted with 2-iodobenzoic acid (1 g, 4.03 mmol), cesium carbonate (2.36 g, 7.2 mmol), trans-N,N'-dimethyl-1,2-cyclohexanediamine (0.10 g, 0.75 mmol) and cuprous iodide (0.08 g, 0.40 mmol) in N,N-dimethylformamide (18 mL) according to the procedure as described in step 5 of example 1, and the crude product was purified by column chromatography on silica gel eluted with (dichloromethane/methanol (v/v)=30/1) to give the title compound (as a yellow solid, 0.51 g, 67%).

MS (ESI, neg. ion) m/z: 188.1 [M−H]$^−$; and
$^1$H NMR (DMSO-d$_6$, 600 MHz) δ (ppm): 13.06 (br.s, 1H), 8.08 (s, 2H), 7.78~7.75 (m, 2H), 7.72~7.68 (m, 1H), 7.60~7.57 (m, 1H);
$^{13}$C NMR (DMSO-d$_6$, 151 MHz) δ (ppm): 167.7, 137.5, 136.3, 131.7, 129.6, 128.9, 128.5, 124.4.

Step 2) Synthesis of 2-(2H-1,2,3-triazole-2-yl)benzoyl Chloride

The title compound was prepared according to the procedure as described in step 6 of example 1. i.e., 2-(2H-1,2,3-triazole-2-yl)benzoic acid (0.37 g, 1.96 mmol) was dissolved in anhydrous dichloromethane (20 mL), and then thionyl chloride (6 mL, 82.7 mmol) and pyridine (0.04 mL, 0.5 mmol) were added slowly. The reaction mixture was gradually warmed to reflux and reacted for 3 h, cooled and the solvent was removed in vacuo. The obtained product was used directly in the next step.

Step 3) Synthesis of 2-(4-(2-(2H-1,2,3-triazol-2-yl)benzoyl)-1,4-diazepan-1-yl)-6-fluoroquinazolin-4(3H)-one 2-(1,4-Diazepan-1-yl)-6-fluoroquinazolin-4(3H)-one (0.16 g, 0.60 mmol) was reacted with 2-(2H-1,2,3-triazole-2-yl)benzoyl chloride (0.15 g, 0.72 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=100/1) to give the title compound (as a white solid, 0.11 g, 42%).

Figure 3:
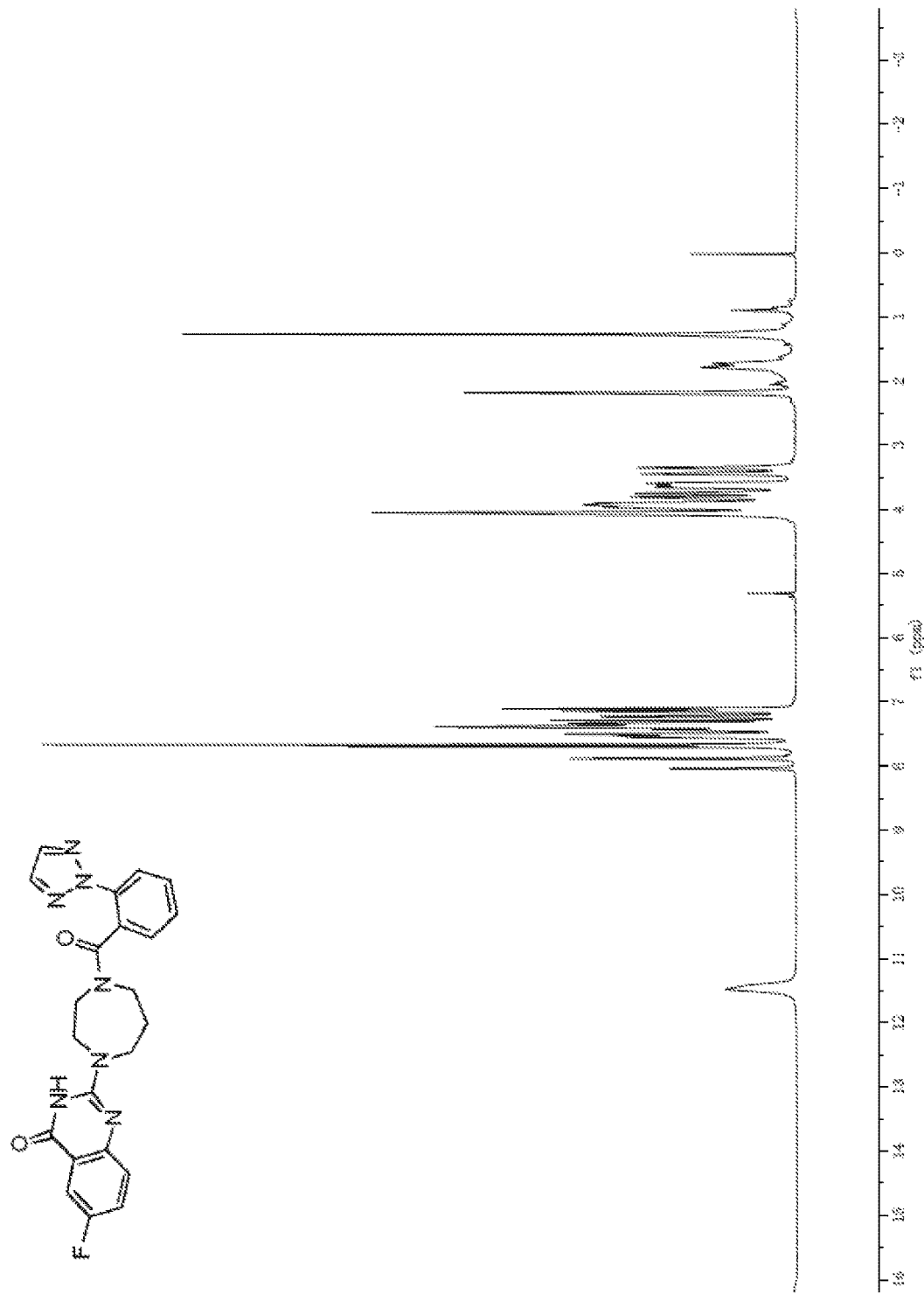
FIG. 3 shows the $^1$H NMR (CDCl$_3$, 600 MHz) spectrum of Example 3 of the invention.
Figure 4:
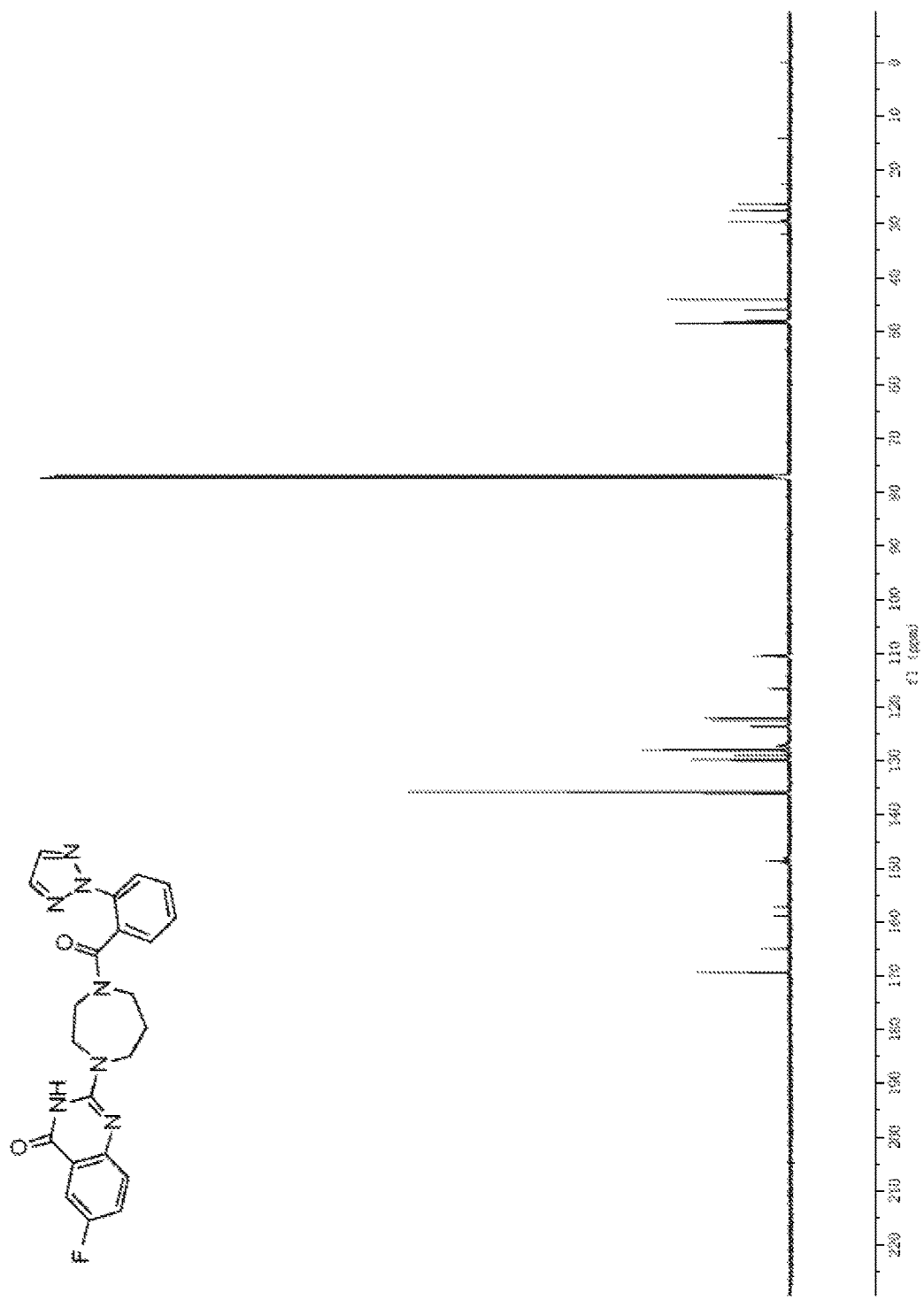
FIG. 4 shows the $^{13C}$ NMR (CDCl$_3$, 151 MHz) spectrum of Example 3 of the invention.

$^1$H NMR (CDCl$_3$, 600 MHz) spectrum is shown in FIG. 3;

$^{13}$C NMR (CDCl$_3$, 151 MHz) spectrum is shown in FIG. 4;

MS (ESI, pos. ion) m/z: 434.1 [M+H]$^+$; and
HPLC: 97.3%.

Example 4: Synthesis of 2-(4-(2-(2H-1,2,3-triazol-2-yl)benzoyl)-5-methyl-1,4-diazepan-1-yl)-6-fluoroquinazolin-4(3H)-one

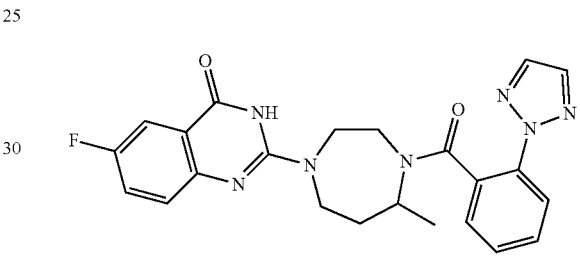

6-Fluoro-2-(5-methyl-1,4-diazepan-1-yl)quinazolin-4(3H)-one (0.14 g, 0.50 mmol) was reacted with 2-(2H-1,2,3-triazole-2-yl)benzoyl chloride (0.13 g, 0.60 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=100/1) to give the title compound (as a white solid, 0.11 g, 51%).

Figure 5:
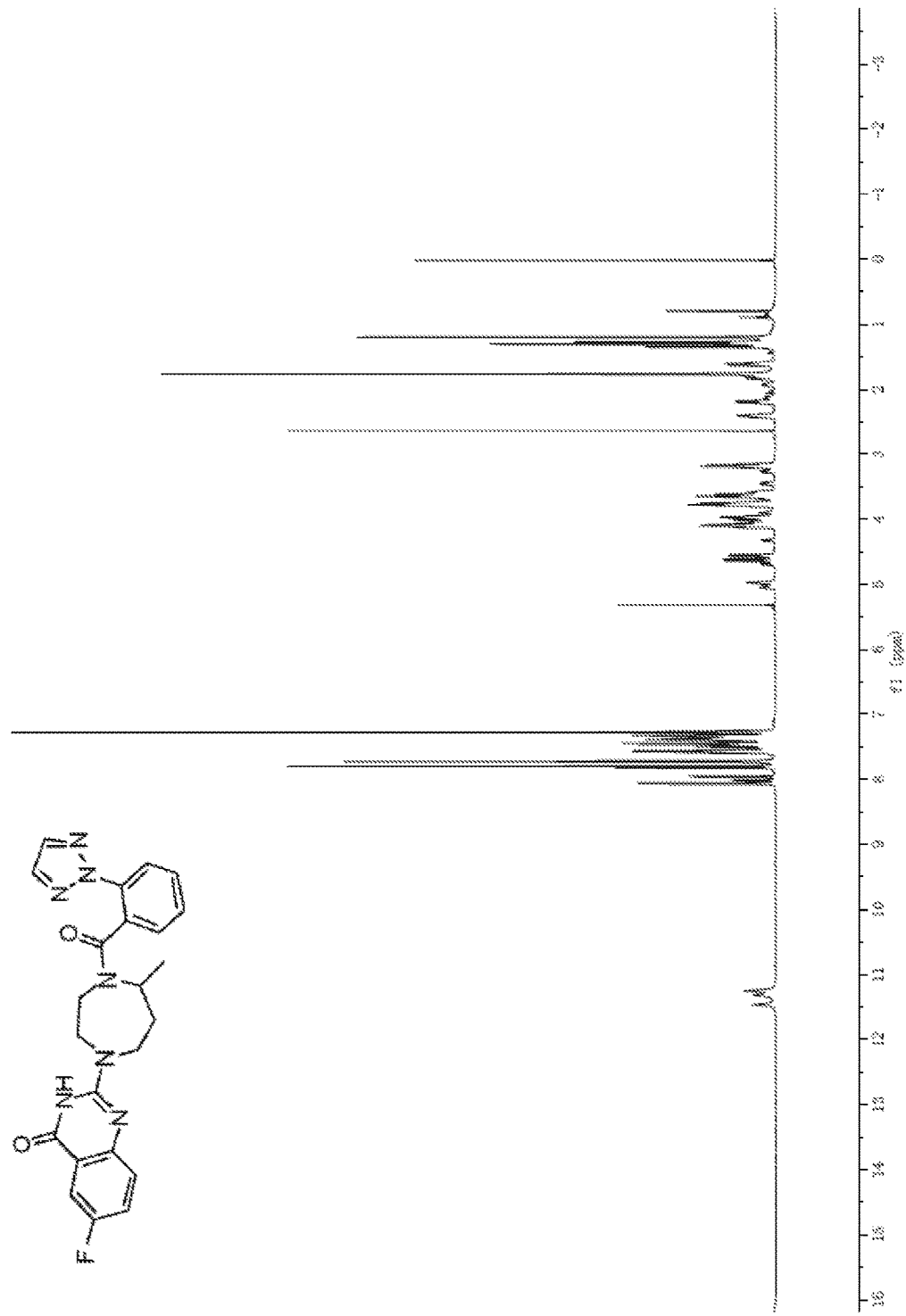
FIG. 5 shows the $^1$H NMR (CDCl$_3$, 600 MHz) spectrum of Example 4 of the invention.

$^1$H NMR (CDCl$_3$, 600 MHz) spectrum is shown in FIG. 5;

MS (ESI, pos. ion) m/z: 448.3 [M+H]$^+$; and
HPLC: 96.8%.

Example 5: Synthesis of 6-chloro-2-(4-(5-methyl-2-(2H-1,2,3-triazol-2-yl)benzoyl)-1,4-diazepan-1-yl)quinazolin-4(3H)-one

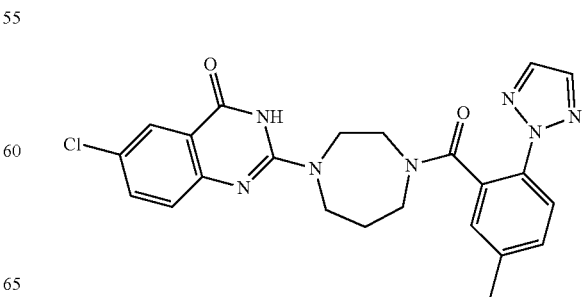

Step 1) Synthesis of 6-chloroquinazolin-2,4-(1H,3H)-dione

2-Amino-5-chlorobenzoic acid (3.43 g, 20.0 mmol) was reacted with urea (18.02 g, 300.0 mmol) in a 100 mL of sealed tube according to the procedure as described in step 1 of example 1, and the crude product was dried to give the title compound (as a gray solid, 3.27 g, 83%).

MS (ESI, neg. ion) m/z: 195.1 [M−H]⁻; and
$^1$H NMR (DMSO-$d_6$, 600 MHz) δ (ppm): 11.34 (s, 2H), 7.81 (d, J=2.5 Hz, 1H), 7.67 (dd, J=8.7 Hz, 2.5 Hz, 1H), 7.18 (d, J=8.7H, 1H).

Step 2) Synthesis of 2,4,6-trichloroquinazoline

6-Chloro-quinazolin-2,4-(1H, 3H)-dione (2.66 g, 13.51 mmol) was reacted with phosphorus pentachloride (8.43 g, 40.50 mmol) in phosphorous oxychloride (30.9 mL, 338 mmol) according to the procedure as described in step 2 of example 1, and the crude product was purified by column chromatography on silica gel eluted with (dichloromethane/methanol (v/v)=50/1) to give the title compound (as a white solid, 0.88 g, 28%).

MS (ESI, pos. ion) m/z: 232.9 [M+H]⁺; and
$^1$H NMR (DMSO-$d_6$, 600 MHz) δ (ppm): 8.02 (d, J=2.5 Hz, 1H), 7.86 (dd, J=8.7 Hz, 2.5 Hz, 1H), 7.64 (d, J=8.7H, 1H).

Step 3) Synthesis of 2,6-dichloroquinazolin-4(3H)-one 2,4,6-Trichloro-quinazoline (0.86 g, 3.70 mmol) was dissolved in a solution of aqueous sodium hydroxide (1 M, 22.2 mL) and tetrahydrofuran (3.5 mL), and the mixture was reacted according to the procedure as described in step 3 of example 1, and the crude product was purified by column chromatography on silica gel eluted with (petroleum ether/ethyl acetate (v/v)=10/1) to give the title compound (as a white solid, 0.70 g, 88%).

MS (ESI, pos. ion) m/z: 215.1 [M+H]⁺; and
$^1$H NMR (DMSO-$d_6$, 600 MHz) δ (ppm): 8.04 (d, J=2.5 Hz, 1H), 7.88 (dd, J=8.7 Hz, 2.5 Hz, 1H), 7.66 (d, J=8.7H, 1H).

Step 4) Synthesis of 6-chloro-2-(1,4-diazepan-1-yl)quinazolin-4(3H)-one 1,4-Diazepane (0.10 g, 1.00 mmol) was reacted with 2,6-dichloro-quinazolin-4(3H)-one (0.19 g, 0.90 mmol) in absolute ethanol (20 mL) according to the procedure as described in step 4 of example 1, and the crude product was purified by column chromatography on silica gel eluted with (dichloromethane/methanol (v/v)=10/1) to give the title compound (as a white solid, 0.22 g, 88%).

MS (ESI, pos. ion) m/z: 279.0 [M+H]⁺; and
$^1$H NMR (DMSO-$d_6$, 600 MHz) δ (ppm): 7.85 (d, J=2.5 Hz, 1H), 7.62 (dd, J=8.8 Hz, 2.6 Hz, 1H), 7.38 (s, 1H), 3.97~3.95 (m, 2H), 3.77 (t, J=6.0 Hz, 2H), 3.21~3.19 (m, 2H), 3.13~3.09 (m, 2H), 2.07~2.02 (m, 2H).

Step 5) Synthesis of 6-chloro-2-(4-(5-methyl-2-(2H-1,2,3-triazol-2-yl)benzoyl)-1,4-diazepan-1-yl)quinazolin-4(3H)-one 6-Chloro-2-(1,4-diazepan-1-yl)quinazolin-4(3H)-one (0.17 g, 0.60 mmol) was reacted with 5-methyl-2-(2H-1,2,3-triazole-2-yl)benzoyl chloride (0.17 g, 0.78 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as a white solid, 0.15 g, 55%).

MS (ESI, pos. ion) m/z: 464.2 [M+H]⁺; and
HPLC: 97.2%.

Example 6: Synthesis of 6-chloro-2-(5-methyl-4-(5-methyl-2-(2H-1,2,3-triazol-2-yl)benzoyl)-1,4-diazepan-1-yl)quinazolin-4(3H)-one

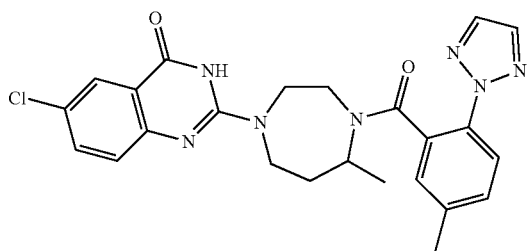 [SMILES: Cc1ccc(-n2nccn2)c(C(=O)N2CCN(c3nc4ccc(Cl)cc4c(=O)[nH]3)CCC2C)c1]

Step 1) Synthesis of 6-chloro-2-(5-methyl-1,4-diazepan-1-yl)quinazolin-4(3H)-one 5-Methyl-1,4-diazepane (0.18 g, 1.58 mmol) was reacted with 2,6-dichloroquinazolin-4(3H)-one (0.32 g, 1.50 mmol) in absolute ethanol (30 mL) according to the procedure as described in step 4 of example 1, and the crude product was purified by column chromatography on silica gel eluted with (dichloromethane/methanol (v/v)=10/1) to give the title compound (as a white solid, 0.47 g, 97%).

MS (ESI, pos. ion) m/z: 293.1 [M+H]⁺; and
$^1$H NMR (DMSO-$d_6$, 600 MHz) δ (ppm): 7.85 (d, J=2.6 Hz, 1H), 7.60 (dd, J=8.8 Hz, 2.6 Hz, 1H), 7.34 (s, 1H), 3.96~3.90 (m, 2H), 3.82~3.77 (m, 1H), 3.64~3.59 (m, 1H), 3.31~3.26 (m, 1H), 3.19~3.14 (m, 1H), 3.10~3.01 (m, 1H), 1.98~1.92 (m, 1H), 1.82~1.76 (m, 1H), 1.21 (d, J=6.5 Hz, 3H).

Step 2) Synthesis of 6-chloro-2-(5-methyl-4-(5-methyl-2-(2H-1,2,3-triazol-2-yl)benzoyl)-1,4-diazepan-1-yl)quinazolin-4(3H)-one 6-Chloro-2-(5-methyl-1,4-diazepan-1-yl)quinazolin-4(3H)-one (0.18 g, 0.60 mmol) was reacted with 5-methyl-2-(2H-1,2,3-triazole-2-yl)benzoyl chloride (0.17 g, 0.78 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as a white solid, 0.26 g, 91%).

MS (ESI, pos. ion) m/z: 478.2 [M+H]⁺; and
HPLC: 95.8%.

Example 7: Synthesis of 2-(4-(2-(2H-1,2,3-triazol-2-yl)benzoyl)-1,4-diazepan-1-yl)-6-chloroquinazolin-4(3H)-one

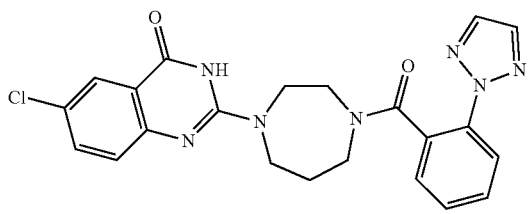 [SMILES: O=C(c1ccccc1-n1nccn1)N1CCCN(c2nc3ccc(Cl)cc3c(=O)[nH]2)CC1]

6-Chloro-2-(1,4-diazepan-1-yl)quinazolin-4(3H)-one (0.11 g, 0.41 mmol) was reacted with 2-(2H-1,2,3-triazole-2-yl)benzoyl chloride (0.11 g, 0.53 mmol) and triethylamine (0.23 mL, 1.63 mmol) in anhydrous dichloromethane (20 mL) according to the procedure as described in step 7 of example 1, and the crude product was purified by silica gel chromatography (dichloromethane/methanol (v/v)=50/1) to give the title compound (as a white solid, 0.12 g, 68%).

MS (ESI, pos. ion) m/z: 450.2 [M+H]$^+$; and

HPLC: 95.3%.

Example 8: Synthesis of 2-(4-(2-(2H-1,2,3-triazol-2-yl)benzoyl)-5-methyl-1,4-diazepan-1-yl)-6-chloro-quinazolin-4(3H)-one

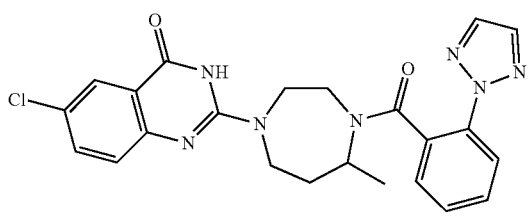 [SMILES: CC1CCN(c2nc3ccc(Cl)cc3c(=O)[nH]2)CCN1C(=O)c1ccccc1-n1nccn1]

6-Chloro-2-(5-methyl-1,4-diazepan-1-yl)quinazolin-4 (3H)-one (0.18 g, 0.60 mmol) was reacted with 2-(2H-1,2,3-triazole-2-yl)benzoyl chloride (0.16 g, 0.78 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as an orange solid, 0.11 g, 40%).

MS (ESI, pos. ion) m/z: 464.2 [M+H]$^+$; and

HPLC: 97.0%.

Example 9: Synthesis of 5-methyl-2-(4-(5-methyl-2-(2H-1,2,3-triazol-2-yl)benzoyl)-1,4-diazepan-1-yl)quinazolin-4(3H)-one

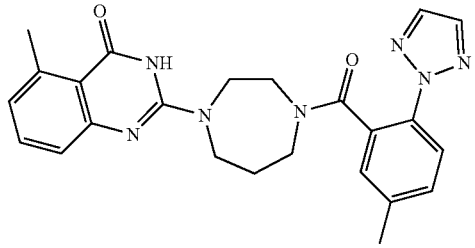 [SMILES: Cc1ccc(-n2nccn2)c(C(=O)N2CCCN(c3nc4cccc(C)c4c(=O)[nH]3)CC2)c1]

Step 1) Synthesis of 5-methylquinazolin-2,4-(1H,3H)-dione

2-Amino-6-methylbenzoic acid (4.54 g, 30.0 mmol) was reacted with urea (27.03 g, 450.0 mmol) in a 200 mL of sealed tube according to the procedure as described in step 1 of example 1, and the crude product was dried to give the title compound (as a brick red solid, 3.81 g, 72%).

MS (ESI, pos. ion) m/z: 177.2 [M+H]$^+$; and $^1$H NMR (DMSO-d$_6$, 400 MHz) δ (ppm): 11.01 (s, 2H), 7.44 (t, J=7.2 Hz, 1H), 7.00 (d, J=7.6 Hz, 1H), 6.92 (d, J=6.8 Hz, 1H), 2.64 (s, 3H).

Step 2) Synthesis of 2,4-dichloro-5-methylquinazoline

5-Methyl-quinazolin-2,4-(1H,3H)-dione (3.80 g, 21.57 mmol) was reacted with phosphorus pentachloride (13.47 g, 64.71 mmol) in phosphorous oxychloride (40 mL, 437 mmol) according to the procedure as described in step 2 of example 1, and the crude product was purified by column chromatography on silica gel eluted with (petroleum ether/ethyl acetate (v/v)=30/1) to give the title compound (as a pale yellow solid, 0.91 g, 20%).

MS (ESI, pos. ion) m/z: 213.1 [M+H]$^+$; and $^1$H NMR (CDCl$_3$, 400 MHz) δ (ppm): 7.86 (d, J=8.2 Hz, 1H), 7.82~7.78 (m, 1H), 7.50 (d, J=7.0 Hz, 1H), 3.02 (s, 3H).

Step 3) Synthesis of 2-chloro-5-methylquinazolin-4(3H)-one 2,4-Dichloro-5-methylquinazoline (0.90 g, 4.22 mmol) was dissolved in a solution of aqueous sodium hydroxide (1 M, 30 mL) and tetrahydrofuran (4.0 mL), and the mixture was reacted according to the procedure as described in step 3 of example 1, and the crude product was purified by column chromatography on silica gel eluted with (dichloromethane/methanol (v/v)=100/1) to give the title compound (as a white solid, 0.82 g, 99%).

MS (ESI, pos. ion) m/z: 195.1 [M+H]$^+$; and $^1$H NMR (CDCl$_3$, 400 MHz) δ (ppm): 10.28 (s, 1H), 7.64~7.60 (m, 1H), 7.50 (d, J=8.1 Hz, 1H), 7.27 (d, J=7.0 Hz, 1H), 2.87 (s, 3H).

Step 4) Synthesis of 2-(1,4-diazepan-1-yl)-5-methylquinazolin-4(3H)-one 1,4-Diazepane (0.11 g, 1.10 mmol) was reacted with 2-chloro-5-methylquinazolin-4 (3H)-one (0.20 g, 1.00 mmol) in absolute ethanol (20 mL) according to the procedure as described in step 4 of example 1, and the crude product was purified by column chromatography on silica gel eluted with (dichloromethane/methanol (v/v)=10/1) to give the title compound (as a white solid, 0.23 g, 88%).

MS (ESI, pos. ion) m/z: 259.3 [M+H]+; and

1H NMR (DMSO-d6, 600 MHz) δ (ppm): 7.59~7.54 (m, 1H), 7.45 (d, J=8.0 Hz, 1H), 7.23~7.20 (m, 1H), 3.95~3.92 (m, 2H), 3.75~3.73 (m, 2H), 3.23~3.20 (m, 2H), 3.13~3.08 (m, 2H), 2.82 (s, 3H), 2.07~2.00 (m, 2H).

Step 5) Synthesis of 5-methyl-2-(4-(5-methyl-2-(2H-1,2,3-triazol-2-yl)benzoyl)-1,4-diazepan-1-yl) quinazolin-4(3H)-one 2-(1,4-diazepan-1-yl)-5-methylquinazolin-4(3H)-one (0.16 g, 0.60 mmol) was reacted with 5-methyl-2-(2H-1,2,3-triazole-2-yl)benzoyl chloride (0.17 g, 0.78 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=80/1) to give the title compound (as a pale yellow solid, 0.16 g, 58%).

MS (ESI, pos. ion) m/z: 444.3 [M+H]+; and

HPLC: 96.9%.

Example 10: Synthesis of 5-methyl-2-(5-methyl-4-(5-methyl-2-(2H-1,2,3-triazol-2-yl) benzoyl)-1,4-diazepan-1-yl)quinazolin-4(3H)-one

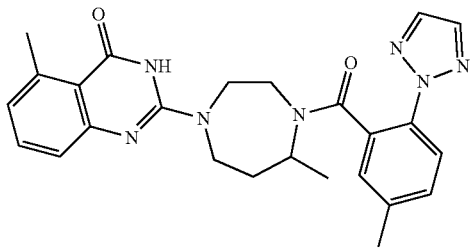 [SMILES: Cc1ccc(-n2nccn2)c(C(=O)N2CCN(c3nc4cccc(C)c4c(=O)[nH]3)CCC2C)c1]

Step 1) Synthesis of 5-methyl-2-(5-methyl-1,4-diazepan-1-yl)quinazolin-4(3H)-one 5-Methyl-1,4-diazepane (0.240 g, 2.1 mmol) was reacted with 2-chloro-5-methylquinazolin-4(3H)-one (0.39 g, 2.0 mmol) in absolute ethanol (30 mL) according to the procedure as described in step 4 of example 1, and the crude product was purified by column chromatography on silica gel eluted with (dichloromethane/methanol (v/v)=10/1) to give the title compound (as a white solid, 0.51 g, 94%).

MS (ESI, pos. ion) m/z: 273.3 [M+H]+; and

1H NMR (DMSO-d6, 600 MHz) δ (ppm): 7.60~7.54 (m, 1H), 7.46 (d, J=8.0 Hz, 1H), 7.22~7.20 (m, 1H), 3.95~3.88 (m, 2H), 3.83~3.76 (m, 1H), 3.65~3.59 (m, 1H), 3.30~3.25 (m, 1H), 3.16~3.10 (m, 1H), 3.07~3.00 (m, 1H), 2.83 (s, 3H), 2.01~1.95 (m, 1H), 1.82~1.76 (m, 1H), 1.22 (d, J=6.4 Hz, 3H).

Step 2) Synthesis of 5-methyl-2-(5-methyl-4-(5-methyl-2-(1,2,3-triazol-2-yl) benzoyl)-1,4-diazepan-1-yl)quinazolin-4(3H)-one 5-Methyl-2-(5-methyl-1,4-diazepan-1-yl)quinazolin-4 (3H)-one (0.16 g, 0.60 mmol) was reacted with 5-methyl-2-(2H-1,2,3-triazole-2-yl)benzoyl chloride (0.17 g, 0.78 mmol) and triethylamine (0.33 mL, 2.4 mmol) in anhydrous dichloromethane (25 mL) according to the procedure as described in step 7 of example 1, and the crude product was purified by silica gel chromatography (dichloromethane/methanol (v/v)=80/1) to give the title compound (as a pale yellow solid, 0.16 g, 57%).

Figure 6:
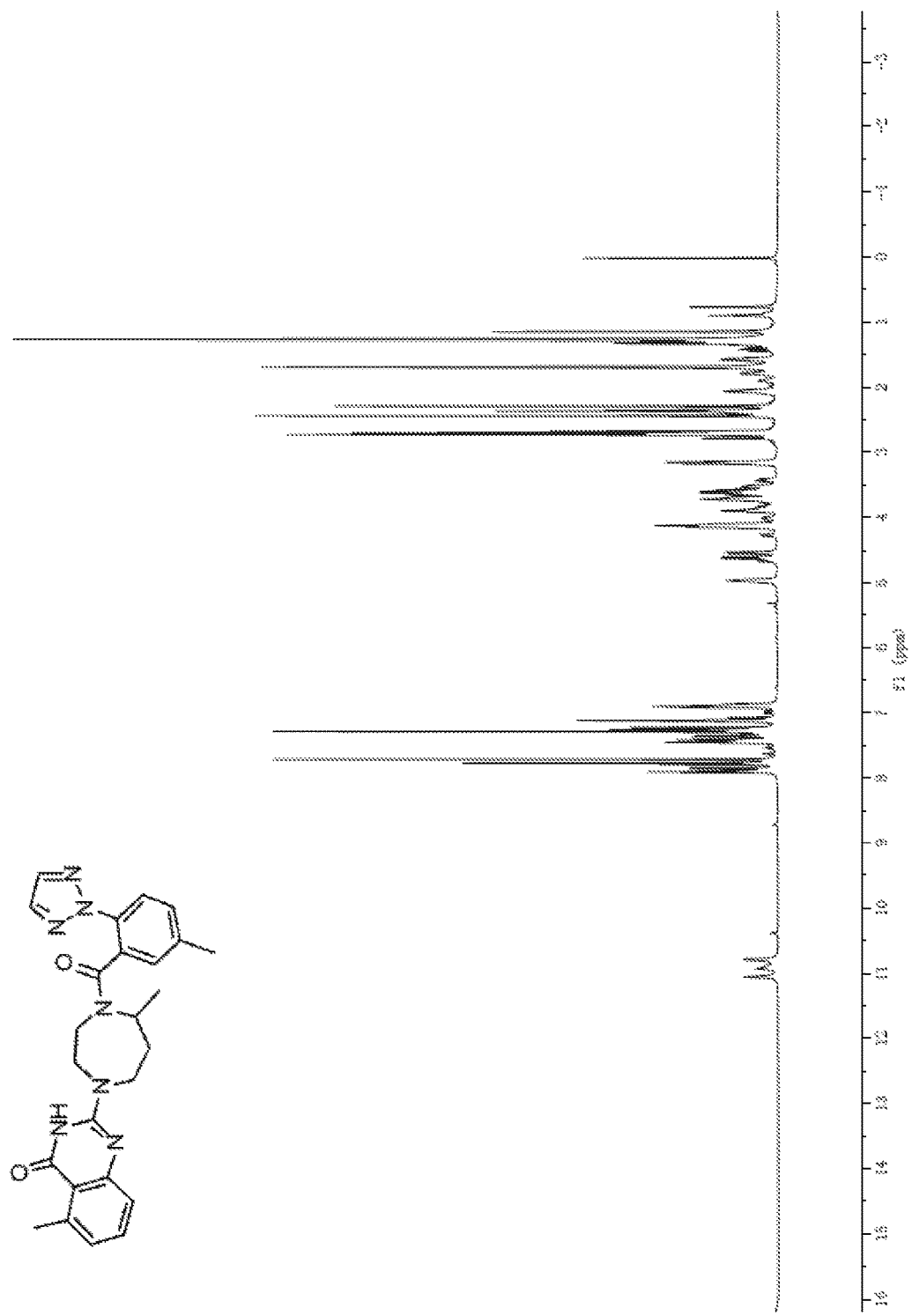
FIG. 6 shows the $^1$H NMR (CDCl$_3$, 600 MHz) spectrum of Example 10 of the invention.

1H NMR (CDCl3, 600 MHz) spectrum is shown in FIG. 6;

MS (ESI, pos. ion) m/z: 458.1 [M+H]+; and

HPLC: 95.9%.

Example 11: Synthesis of 2-(4-(2-(2H-1,2,3-triazol-2-yl)benzoyl)-1,4-diazepan-1-yl)-5-methylquinazolin-4(3H)-one

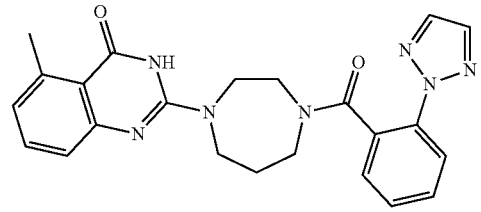 [SMILES: Cc1cccc2nc(N3CCCN(C(=O)c4ccccc4-n4nccn4)CC3)[nH]c(=O)c12]

2-(1,4-Diazepan-1-yl)-5-methylquinazolin-4(3H)-one (0.13 g, 0.5 mmol) was reacted with 2-(2H-1,2,3-triazole-2-yl)benzoyl chloride (0.13 g, 0.6 mmol) and triethylamine (0.28 mL, 2 mmol) in anhydrous dichloromethane (20 mL) according to the procedure as described in step 7 of example 1, and the crude product was purified by silica gel chromatography (dichloromethane/methanol (v/v)=50/1) to give the title compound (as a pale yellow solid, 0.16 g, 73%).

MS (ESI, pos. ion) m/z: 429.9 [M+H]+; and

HPLC: 96.8%.

Example 12: Synthesis of 2-(4-(2-(2H-1,2,3-triazol-2-yl)benzoyl)-5-methyl-1,4-diazepan-1-yl)-5-methylquinazolin-4(3H)-one

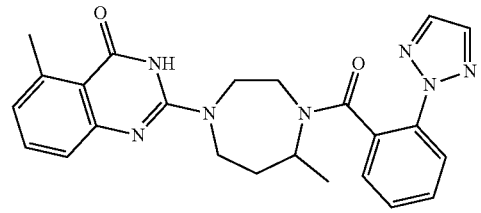 [SMILES: Cc1cccc2nc(N3CCC(C)N(C(=O)c4ccccc4-n4nccn4)CC3)[nH]c(=O)c12]

5-Methyl-2-(5-methyl-1,4-diazepan-1-yl)quinazolin-4 (3H)-one (0.19 g, 0.70 mmol) was reacted with 2-(2H-1,2,3-triazole-2-yl)benzoyl chloride (0.17 g, 0.84 mmol) and triethylamine (0.39 mL, 2.8 mmol) in anhydrous dichloromethane (20 mL) according to the procedure as described in step 7 of example 1, and the crude product was purified by silica gel chromatography (dichloromethane/methanol (v/v)=50/1) to give the title compound (as a pale yellow solid, 0.16 g, 52%).

MS (ESI, pos. ion) m/z: 444.3 [M+H]+; and

HPLC: 98.5%.

Example 13: Synthesis of 5-chloro-2-(4-(5-methyl-2-(2H-1,2,3-triazol-2-yl)benzoyl)-1,4-diazepan-1-yl)quinazolin-4(3H)-one

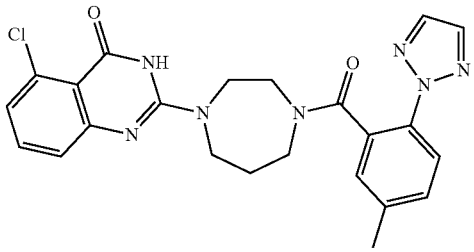 [SMILES: Cc1ccc(-n2nccn2)c(C(=O)N2CCCN(c3nc4cccc(Cl)c4c(=O)[nH]3)CC2)c1]

Step 1) Synthesis of 5-chloroquinazolin-2,4-(1H,3H)-dione

2-Amino-6-chlorobenzoic acid (5.98 g, 34.9 mmol) was reacted with urea (31.50 g, 524.5 mmol) in a 200 mL of sealed tube according to the procedure as described in step 1 of example 1, and the crude product was dried to give the title compound (as a gray solid, 4.51 g, 66%).

MS (ESI, neg. ion) m/z: 195.1 [M−H]$^-$; and
$^1$H NMR (DMSO-d$_6$, 400 MHz) δ (ppm): 11.25 (s, 2H), 7.54 (t, J=8.0 Hz, 1H), 7.18 (d, J=8.0 Hz, 1H), 7.10 (d, J=8.4 Hz, 1H).

Step 2) Synthesis of 2,4,5-trichloroquinazoline

5-Chloroquinazolin-2,4-(1H,3H)-dione (4.00 g, 20.35 mmol) was reacted with phosphorus pentachloride (16.64 g, 78.31 mmol) in phosphorous oxychloride (12 mL) according to the procedure as described in step 2 of example 1, and the crude product was purified by column chromatography on silica gel eluted with (petroleum ether/ethyl acetate (v/v)=20/1) to give the title compound (as a white solid, 2.38 g, 50%).

MS (ESI, pos. ion) m/z: 232.9 [M+H]$^+$; and
$^1$H NMR (CDCl$_3$, 400 MHz) δ (ppm): 7.94 (dd, J=8.0 Hz, 1.2 Hz, 1H), 7.83 (t, J=8.0 Hz, 1H), 7.79 (d, J=1.2 Hz, 1H).

Step 3) Synthesis of 2,5-dichloroquinazolin-4(3H)-one 2,4,5-Trichloroquinazoline (2.50 g, 10.71 mmol) was dissolved in a solution of aqueous sodium hydroxide (1 M, 50 mL) and tetrahydrofuran (6.00 mL), and the mixture was reacted according to the procedure as described in step 3 of example 1, and the crude product was purified by column chromatography on silica gel eluted with (petroleum ether/ethyl acetate (v/v)=4/1) to give the title compound (as a white solid, 2.00 g, 87%).

MS (ESI, pos. ion) m/z: 215.0 [M+H]$^+$; and
$^1$H NMR (DMSO-d$_6$, 400 MHz) δ (ppm): 7.73 (t, J=8.4 Hz, 1H), 7.54 (d, J=2.4 Hz, 1H), 7.52 (d, J=2.4 Hz, 1H).

Step 4) Synthesis of 5-chloro-2-(1,4-diazepan-1-yl)quinazolin-4(3H)-one 1,4-Diazepane (0.12 g, 1.20 mmol) was reacted with 2,5-dichloroquinazolin-4(3H)-one (0.22 g, 1.00 mmol) in absolute ethanol (25 mL) according to the procedure as described in step 4 of example 1, and the crude product was purified by column chromatography on silica gel eluted with (dichloromethane/methanol (v/v)=10/1) to give the title compound (as a white solid, 0.24 g, 85%).

MS (ESI, pos. ion) m/z: 279.3 [M+H]$^+$; and
$^1$H NMR (DMSO-d$_6$, 600 MHz) δ (ppm): 7.82~7.77 (m, 1H), 7.69 (d, J=8.2 Hz, 1H), 7.42~7.39 (m, 1H), 3.95~3.90 (m, 2H), 3.77 (t, J=6.1 Hz, 2H), 3.24~3.17 (m, 4H), 2.07~2.03 (m, 2H).

Step 5) Synthesis of 5-chloro-2-(4-(5-methyl-2-(2H-1,2,3-triazol-2-yl)benzoyl)-1,4-diazepan-1-yl)quinazolin-4(3H)-one 5-Chloro-2-(1,4-diazepan-1-yl)quinazolin-4(3H)-one (0.18 g, 0.65 mmol) was reacted with 5-methyl-2-(2H-1,2,3-triazole-2-yl)benzoyl chloride (0.17 g, 0.78 mmol) and triethylamine (0.33 mL, 2.4 mmol) in anhydrous dichloromethane (25 mL) according to the procedure as described in step 7 of example 1, and the crude product was purified by silica gel chromatography (dichloromethane/methanol (v/v)=80/1) to give the title compound (as a white solid, 0.19 g, 64%).

MS (ESI, pos. ion) m/z: 464.2 [M+H]$^+$; and
HPLC: 98.6%.

Example 14: Synthesis of 5-chloro-2-(5-methyl-4-(5-methyl-2-(2H-1,2,3-triazol-2-yl) benzoyl)-1,4-diazepan-1-yl)quinazolin-4(3H)-one

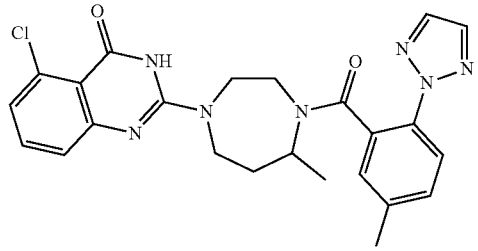 [SMILES: Cc1ccc(-n2nccn2)c(C(=O)N2CCN(c3nc4cccc(Cl)c4c(=O)[nH]3)CCC2C)c1]

Step 1) Synthesis of 5-chloro-2-(5-methyl-1,4-diazepan-1-yl)quinazolin-4(3H)-one 5-Methyl-1,4-diazepane (0.25 g, 2.2 mmol) was reacted with 2,5-dichloroquinazolin-4(3H)-one (0.43 g, 2.0 mmol) in absolute ethanol (30 mL) according to the procedure as described in step 4 of example 1, and the crude product was purified by column chromatography on silica gel eluted with (dichloromethane/methanol (v/v)=10/1) to give the title compound (as a white solid, 0.54 g, 93%).

MS (ESI, pos. ion) m/z: 293.3 [M+H]$^+$; and
$^1$H NMR (DMSO-d$_6$, 600 MHz) δ (ppm): 7.83~7.79 (m, 1H), 7.70 (d, J=8.0 Hz, 1H), 7.43~7.39 (m, 1H), 3.93~3.90 (m, 2H), 3.81~3.75 (m, 1H), 3.64~3.57 (m, 1H), 3.30~3.26 (m, 1H), 3.19~3.15 (m, 1H), 3.08~3.01 (m, 1H), 1.99~1.92 (m, 1H), 1.82~1.77 (m, 1H), 1.19 (d, J=6.4 Hz, 3H).

Step 2) Synthesis of 5-chloro-2-(5-methyl-4-(5-methyl-2-(2H-1,2,3-triazol-2-yl)benzoyl)-1,4-diazepan-1-yl)quinazolin-4(3H)-one 5-Chloro-2-(5-methyl-1,4-diazepan-1-yl)quinazolin-4(3H)-one (0.15 g, 0.50 mmol) was reacted with 5-methyl-2-(2H-1,2,3-triazole-2-yl)benzoyl chloride (0.13 g, 0.6 mmol) and triethylamine (0.28 mL, 2.0 mmol) in anhydrous dichloromethane (25 mL) according to the procedure as described in step 7 of example 1, and the crude product was purified by silica gel chromatography (dichloromethane/methanol (v/v)=80/1) to give the title compound (as a white solid, 0.20 g, 84%).

MS (ESI, pos. ion) m/z: 478.1 [M+H]$^+$; and
HPLC: 97.7%.

Example 15: Synthesis of 2-(4-(2-(2H-1,2,3-triazol-2-yl)benzoyl)-1,4-diazepan-1-yl)-5-chloroquinazolin-4(3H)-one

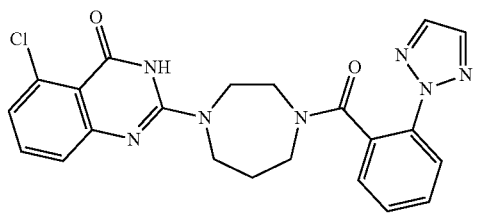 [SMILES: O=C(c1ccccc1-n1nccn1)N1CCCN(c2nc3cccc(Cl)c3c(=O)[nH]2)CC1]

5-Chloro-2-(1,4-diazepan-1-yl)quinazolin-4(3H)-one (0.17 g, 0.6 mmol) was reacted with 2-(2H-1,2,3-triazole-2-yl)benzoyl chloride (0.15 g, 0.7 mmol) and triethylamine (0.28 mL, 2 mmol) in anhydrous dichloromethane (20 mL) according to the procedure as described in step 7 of example 1, and the crude product was purified by silica gel chromatography (dichloromethane/methanol (v/v)=50/1) to give the title compound (as a white solid, 0.21 g, 79%).

Figure 7:
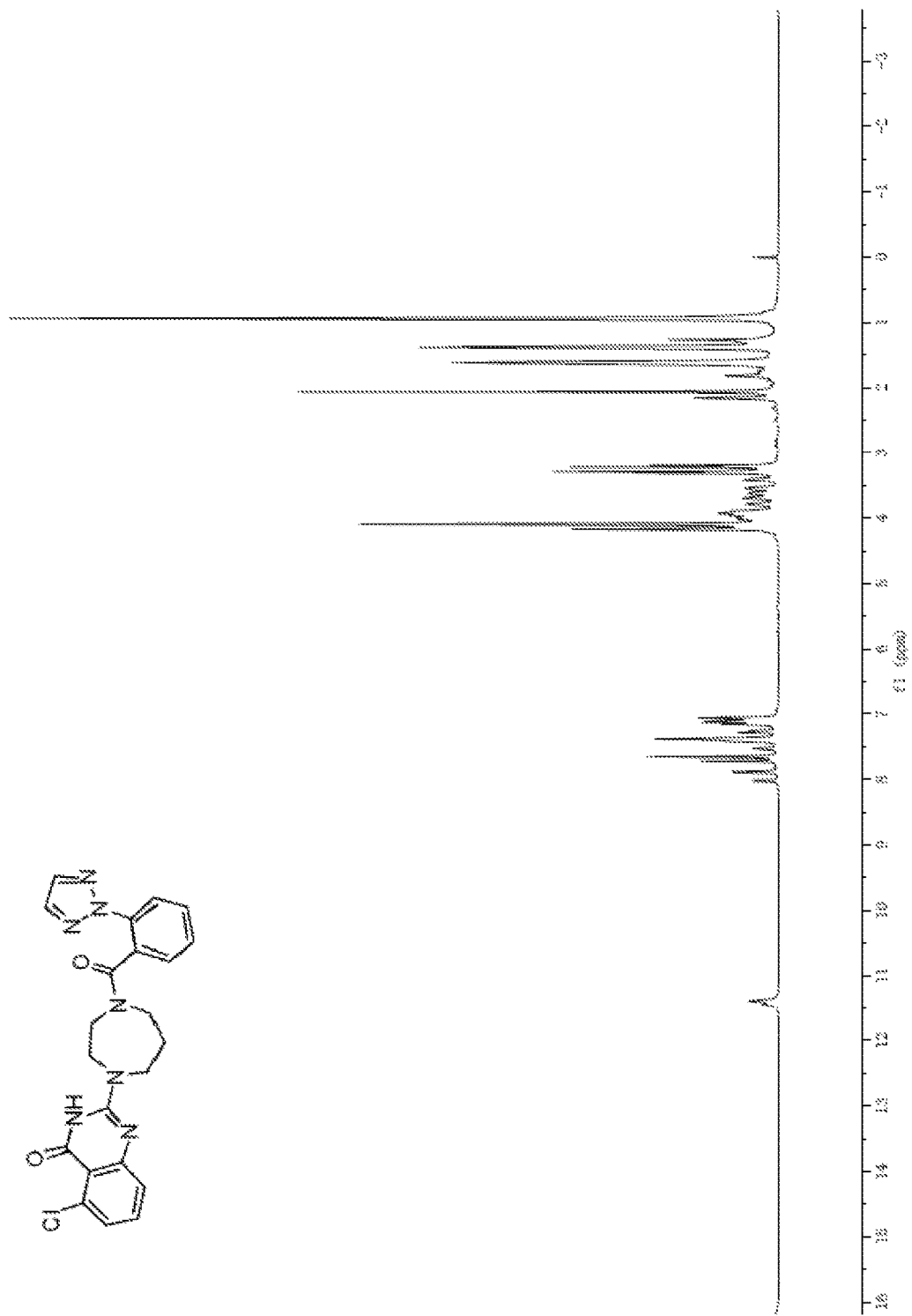
FIG. 7 shows the $^1$H NMR (CDCl$_3$, 600 MHz) spectrum of Example 15 of the invention.
Figure 8:
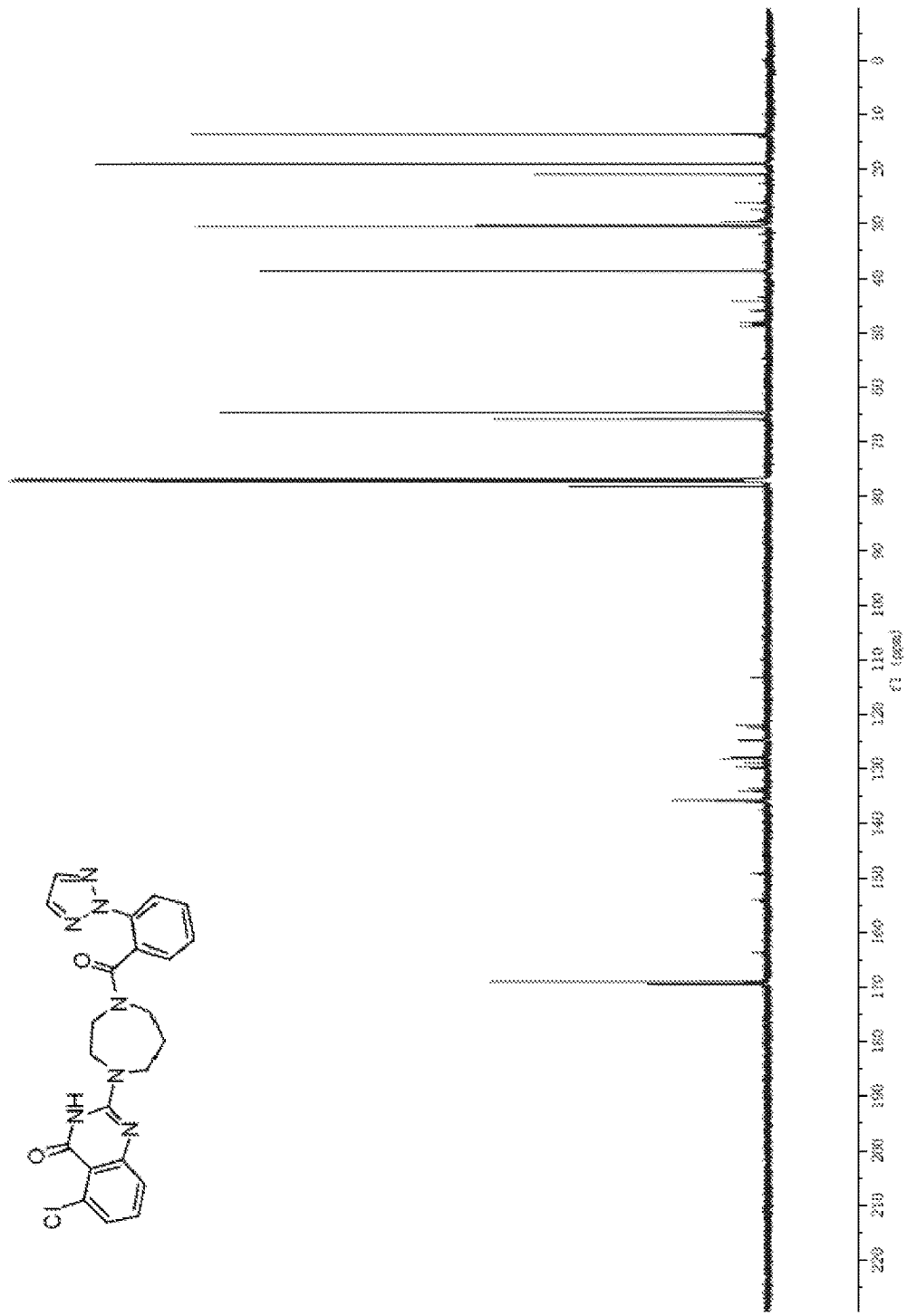
FIG. 8 shows the $^{13}$C NMR (CDCl$_3$, 151 MHz) spectrum of Example 15 of the invention.

$^1$H NMR (CDCl$_3$, 600 MHz) spectrum is shown in FIG. 7;
$^{13}$C NMR (CDCl$_3$, 151 MHz) spectrum is shown in FIG. 8;
MS (ESI, pos. ion) m/z: 450.2 [M+H]$^+$; and
HPLC: 98.1%.

Example 16: Synthesis of 2-(4-(2-(2H-1,2,3-triazol-2-yl)benzoyl)-5-methyl-1,4-diazepan-1-yl)-5-chloroquinazolin-4(3H)-one

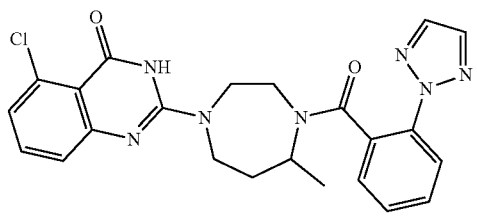 [SMILES: CC1CCN(c2nc3cccc(Cl)c3c(=O)[nH]2)CCN1C(=O)c1ccccc1-n1nccn1]

5-Chloro-2-(5-methyl-1,4-diazepan-1-yl)quinazolin-4 (3H)-one (0.18 g, 0.60 mmol) was reacted with 2-(2H-1,2,3-triazole-2-yl)benzoyl chloride (0.16 g, 0.78 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as a white solid, 0.18 g, 65%).

MS (ESI, pos. ion) m/z: 464.3 [M+H]$^+$; and
HPLC: 97.8%.

Example 17: Synthesis of 6-methoxy-2-(4-(5-methyl-2-(2H-1,2,3-triazol-2-yl)benzoyl)-1,4-diazepan-1-yl)quinazolin-4(3H)-one

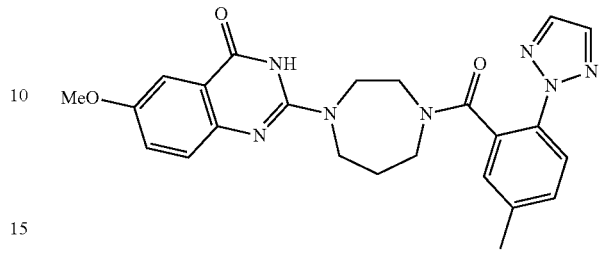

Step 1) Synthesis of 6-methoxyquinazolin-2,4-(1H,3H)-dione

2-Amino-6-methoxybenzoic acid (2.51 g, 15.0 mmol) was reacted with urea (13.51 g, 225.0 mmol) in a 200 mL of sealed tube according to the procedure as described in step 1 of example 1, and the crude product was dried to give the title compound (as a gray solid, 2.30 g, 80%).

MS (ESI, neg. ion) m/z: 191.0[M–H]$^-$; and
$^1$H NMR (DMSO-d$_6$, 400 MHz) δ (ppm): 11.24 (s, 1H), 11.06 (s, 1H), 7.36 (d, J=2.9 Hz, 1H), 7.32 (dd, J=8.8 Hz, 2.9 Hz, 1H), 7.16 (d, J=8.8 Hz, 1H), 3.82 (s, 3H).

Step 2) Synthesis of 2,4-dichloro-6-methoxyquinazoline

6-Methoxyquinazolin-2,4-(1H,3H)-dione (1.84 g, 9.57 mmol) was reacted with phosphorus pentachloride (5.97 g, 28.65 mmol) in phosphorous oxychloride (21.9 mL, 239 mmol) according to the procedure as described in step 2 of example 1, and the crude product was purified by column chromatography on silica gel eluted with (petroleum ether/ethyl acetate (v/v)=10/1) to give the title compound (as a white solid, 1.78 g, 81%).

MS (ESI, pos. ion) m/z: 229.1 [M+H]$^+$; and
$^1$H NMR (CDCl$_3$, 400 MHz) δ (ppm): 7.89 (d, J=9.2 Hz, 1H), 7.61 (dd, J=9.2 Hz, 2.8 Hz, 1H), 7.40 (d, J=2.7 Hz, 1H), 3.99 (s, 3H).

Step 3) Synthesis of 2-chloro-6-methoxyquinazolin-4(3H)-one 2,4-Dichloro-6-methoxyquinazoline (2.11 g, 9.21 mmol) was dissolved in a solution of aqueous sodium hydroxide (1 M, 55.3 mL) and tetrahydrofuran (20 mL), and the mixture was reacted according to the procedure as described in step 3 of example 1, and the crude product was purified by column chromatography on silica gel eluted with (dichloromethane/methanol (v/v)=100/1) to give the title compound (as a white solid, 1.91 g, 98%).

MS (ESI, pos. ion) m/z: 211.0 [M+H]$^+$; and
$^1$H NMR (CDCl$_3$, 600 MHz) δ (ppm): 7.63~7.60 (m, 2H), 7.38 (dd, J=8.9 Hz, 3.0 Hz, 1H), 3.93 (s, 3H).

Step 4) Synthesis of 2-(1,4-diazepan-1-yl)-6-methoxyquinazolin-4(3H)-one 1,4-Diazepane (0.16 g, 1.61 mmol) was reacted with 2-chloro-6-methoxyquinazolin-4(3H)-one (0.31 g, 1.46 mmol) in absolute ethanol (30 mL) according to the procedure as described in step 4 of example 1, and the crude product was purified by column chromatography on silica gel eluted with (dichloromethane/methanol (v/v)=10/1) to give the title compound (as a white solid, 0.26 g, 66%).

MS (ESI, pos. ion) m/z: 275.0 [M+H]$^+$; and $^1$H NMR (DMSO-d$_6$, 400 MHz) δ (ppm): 7.37 (d, J=2.7 Hz, 1H), 7.28~7.25 (m, 1H), 7.20 (s, 1H), 3.95~3.93 (m, 2H), 3.81 (s, 3H), 3.75 (t, J=5.9 Hz, 2H), 3.23~3.08 (m, 4H), 2.06~2.02 (m, 2H).

Step 5) Synthesis of 6-methoxy-2-(4-(5-methyl-2-(2H-1,2,3-triazol-2-yl)benzoyl)-1,4-diazepan-1-yl)quinazolin-4(3H)-one 2-(1,4-Diazepan-1-yl)-6-methoxyquinazolin-4(3H)-one (0.16 g, 0.60 mmol) was reacted with 5-methyl-2-(2H-1,2,3-triazole-2-yl)benzoyl chloride (0.16 g, 0.73 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as a pale yellow solid, 0.11 g, 39%).

MS (ESI, pos. ion) m/z: 459.9 [M+H]$^+$; and

HPLC: 95.6%.

Example 18: Synthesis of 6-methoxy-2-(5-methyl-4-(5-methyl-2-(2H-1,2,3-triazol-2-yl) benzoyl)-1,4-diazepan-1-yl)quinazolin-4(3H)-one

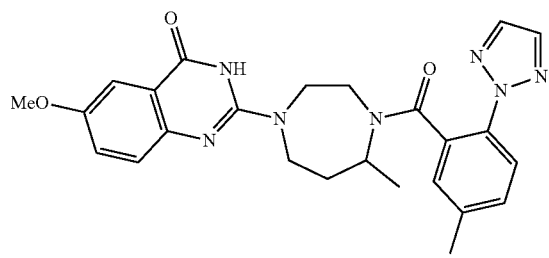 [SMILES: COc1ccc2nc(N3CCC(C)N(C(=O)c4cc(C)ccc4-n4nccn4)CC3)[nH]c(=O)c2c1]

Step 1) Synthesis of 6-methoxy-2-(5-methyl-1,4-diazepan-1-yl)quinazolin-4(3H)-one 5-Methyl-1,4-diazepane (0.13 g, 1.10 mmol) was reacted with 2-chloro-6-methoxyquinazolin-4(3H)-one (0.21 g, 1.00 mmol) in absolute ethanol (30 mL) according to the procedure as described in step 4 of example 1, and the crude product was purified by column chromatography on silica gel eluted with (dichloromethane/methanol (v/v)=10/1) to give the title compound (as a pale yellow solid, 0.23 g, 78%).

MS (ESI, pos. ion) m/z: 289.3 [M+H]$^+$; and $^1$H NMR (DMSO-d$_6$, 400 MHz) δ (ppm): 7.36 (d, J=2.8 Hz, 1H), 7.25~7.20 (m, 2H), 3.91~3.81 (m, 3H), 3.79 (s, 3H), 3.60~3.55 (m, 1H), 3.29~3.24 (m, 1H), 3.19~3.14 (m, 1H), 3.06~3.01 (m, 1H), 1.97~1.72 (m, 2H), 1.18 (d, J=6.1 Hz, 3H).

Step 2) Synthesis of 6-methoxy-2-(5-methyl-4-(5-methyl-2-(2H-1,2,3-triazol-2-yl) benzoyl)-1,4-diazepan-1-yl)quinazolin-4(3H)-one 6-Methoxy-2-(5-methyl-1,4-diazepan-1-yl)quinazolin-4(3H)-one (0.17 g, 0.59 mmol) was reacted with 5-methyl-2-(2H-1,2,3-triazole-2-yl)benzoyl chloride (0.16 g, 0.73 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as a pale yellow solid, 0.15 g, 54%).

MS (ESI, pos. ion) m/z: 473.9 [M+H]$^+$; and

HPLC: 96.3%.

Example 19: Synthesis of 2-(4-(2-(2H-1,2,3-triazol-2-yl)benzoyl)-1,4-diazepan-1-yl)-6-methoxyquinazolin-4(3H)-one

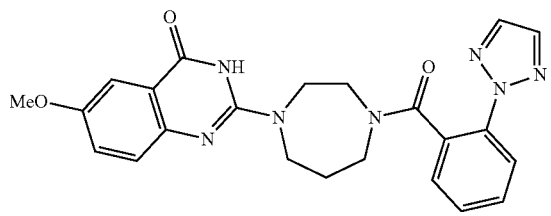 [SMILES: COc1ccc2nc(N3CCCN(C(=O)c4ccccc4-n4nccn4)CC3)[nH]c(=O)c2c1]

2-(1,4-Diazepan-1-yl)-6-methoxyquinazolin-4(3H)-one (0.17 g, 0.6 mmol) was reacted with 2-(2H-1,2,3-triazole-2-yl)benzoyl chloride (0.15 g, 0.7 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as a pale yellow solid, 0.17 g, 64%).

MS (ESI, pos. ion) m/z: 445.9 [M+H]$^+$; and

HPLC: 99.1%.

Example 20: Synthesis of 2-(4-(2-(2H-1,2,3-triazol-2-yl)benzoyl)-5-methyl-1,4-diazepan-1-yl)-6-methoxyquinazolin-4(3H)-one

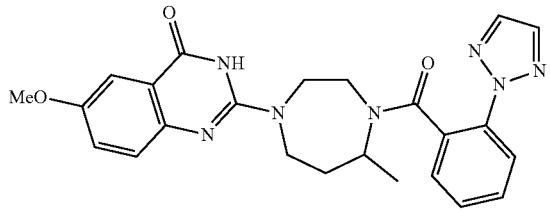 [SMILES: COc1ccc2nc(N3CCC(C)N(C(=O)c4ccccc4-n4nccn4)CC3)[nH]c(=O)c2c1]

6-Methoxy-2-(5-methyl-1,4-diazepan-1-yl)quinazolin-4(3H)-one (0.14 g, 0.50 mmol) was reacted with 2-(2H-1,2,3-triazole-2-yl)benzoyl chloride (0.13 g, 0.6 mmol) and triethylamine (0.28 mL, 2.0 mmol) in anhydrous dichloromethane (20 mL) according to the procedure as described in step 7 of example 1, and the crude product was purified by silica gel chromatography (dichloromethane/methanol (v/v)=50/1) to give the title compound (as a pale yellow solid, 0.17 g, 72%).

MS (ESI, pos. ion) m/z: 460.3 [M+H]$^+$; and

HPLC: 99.4%.

Example 21: Synthesis of 6,7-dimethoxy-2-(4-(5-methyl-2-(2H-1,2,3-triazol-2-yl)benzoyl)-1,4-diazepan-1-yl)quinazolin-4(3H)-one

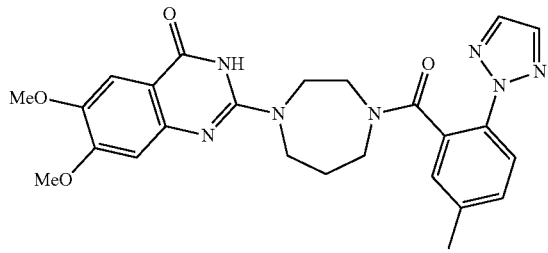 [SMILES: COc1cc2nc(N3CCCN(C(=O)c4cc(C)ccc4-n4nccn4)CC3)[nH]c(=O)c2cc1OC]

Step 1) Synthesis of 6,7-dimethoxyquinazolin-2,4-(1H,3H)-dione

2-Amino-4,5-dimethoxybenzoic acid (1.97 g, 9.99 mmol) was reacted with urea (9.00 g, 149.86 mmol) in a 200 mL of sealed tube according to the procedure as described in step 1 of example 1, and the crude product was dried to give the title compound (as a gray solid, 0.62 g, 28%).

MS (ESI, neg. ion) m/z: 221.1[M−H]$^-$; and $^1$H NMR (DMSO-d$_6$, 400 MHz) δ (ppm): 11.12 (s, 1H), 11.02 (s, 1H), 7.42 (s, 1H), 7.35 (s, 1H), 3.71 (s, 3H), 3.69 (s, 3H).

Step 2) Synthesis of 2,4-dichloro-6,7-dimethoxyquinazoline 6,7-Dimethoxy-quinazolin-2,4-(1H,3H)-dione (0.60 g, 2.70 mmol) was reacted with phosphorus pentachloride (2.32 g, 10.90 mmol) in phosphorous oxychloride (12 mL) according to the procedure described in step 2 of example 1, and the crude product was purified by column chromatography on silica gel eluted with (petroleum ether/ethyl acetate (v/v)=20/1) to give the title compound (as a pale yellow solid, 0.20 g, 29%).

MS (ESI, pos. ion) m/z: 258.9 [M+H]$^+$; and $^1$H NMR (CDCl$_3$, 400 MHz) δ (ppm): 7.36 (s, 1H), 7.28 (s, 1H), 4.07 (s, 3H), 4.06 (s, 3H).

Step 3) Synthesis of 2-chloro-6,7-dimethoxyquinazolin-4(3H)-one 2,4-Dichloro-6,7-dimethoxyquinazoline (0.20 g, 0.77 mmol) was dissolved in a solution of aqueous sodium hydroxide (1 M, 25 mL) and tetrahydrofuran (3.00 mL), and the mixture was reacted according to the procedure as described in step 3 of example 1, and the crude product was purified by column chromatography on silica gel eluted with (petroleum ether/ethyl acetate (v/v)=4/1) to give the title compound (as a white solid, 0.17 g, 92%).

MS (ESI, neg. ion) m/z: 238.9 [M−H]$^-$; and $^1$H NMR (DMSO-d$_6$, 600 MHz) δ (ppm): 13.10 (s, 1H), 7.41 (s, 1H), 7.12 (s, 1H), 3.90 (s, 3H), 3.87 (s, 3H).

Step 4) Synthesis of 2-(1,4-diazepan-1-yl)-6,7-dimethoxyquinazolin-4(3H)-one 1,4-Diazepane (0.11 g, 1.10 mmol) was reacted with 2-chloro-6,7-dimethoxyquinazolin-4(3H)-one (0.24 g, 1.0 mmol) in absolute ethanol (20 mL) according to the procedure as described in step 4 of example 1, and the crude product was purified by column chromatography on silica gel eluted with (dichloromethane/methanol (v/v)=10/1) to give the title compound (as a white solid, 0.26 g, 85%).

MS (ESI, pos. ion) m/z: 305.3 [M+H]$^+$; and $^1$H NMR (DMSO-d$_6$, 400 MHz) δ (ppm): 7.42 (s, 1H), 7.13 (s, 1H), 3.97~3.95 (m, 2H), 3.91 (s, 3H), 3.89 (s, 3H), 3.76 (t, J=6.0 Hz, 2H), 3.22~3.09 (m, 4H), 2.08~2.01 (m, 2H).

Step 5) Synthesis of 6,7-dimethoxy-2-(4-(5-methyl-2-(2H-1,2,3-triazol-2-yl)benzoyl)-1,4-diazepan-1-yl)quinazolin-4(3H)-one 2-(1,4-Diazepan-1-yl)-6,7-dimethoxyquinazolin-4(3H)-one (0.15 g, 0.50 mmol) was reacted with 5-methyl-2-(2H-1,2,3-triazole-2-yl)benzoyl chloride (0.13 g, 0.60 mmol) and triethylamine (0.28 mL, 2.0 mmol) in anhydrous dichloromethane (20 mL) according to the procedure as described in step 7 of example 1, and the crude product was purified by silica gel chromatography (dichloromethane/methanol (v/v)=50/1) to give the title compound (as a pale yellow solid, 0.13 g, 52%).

Figure 9:
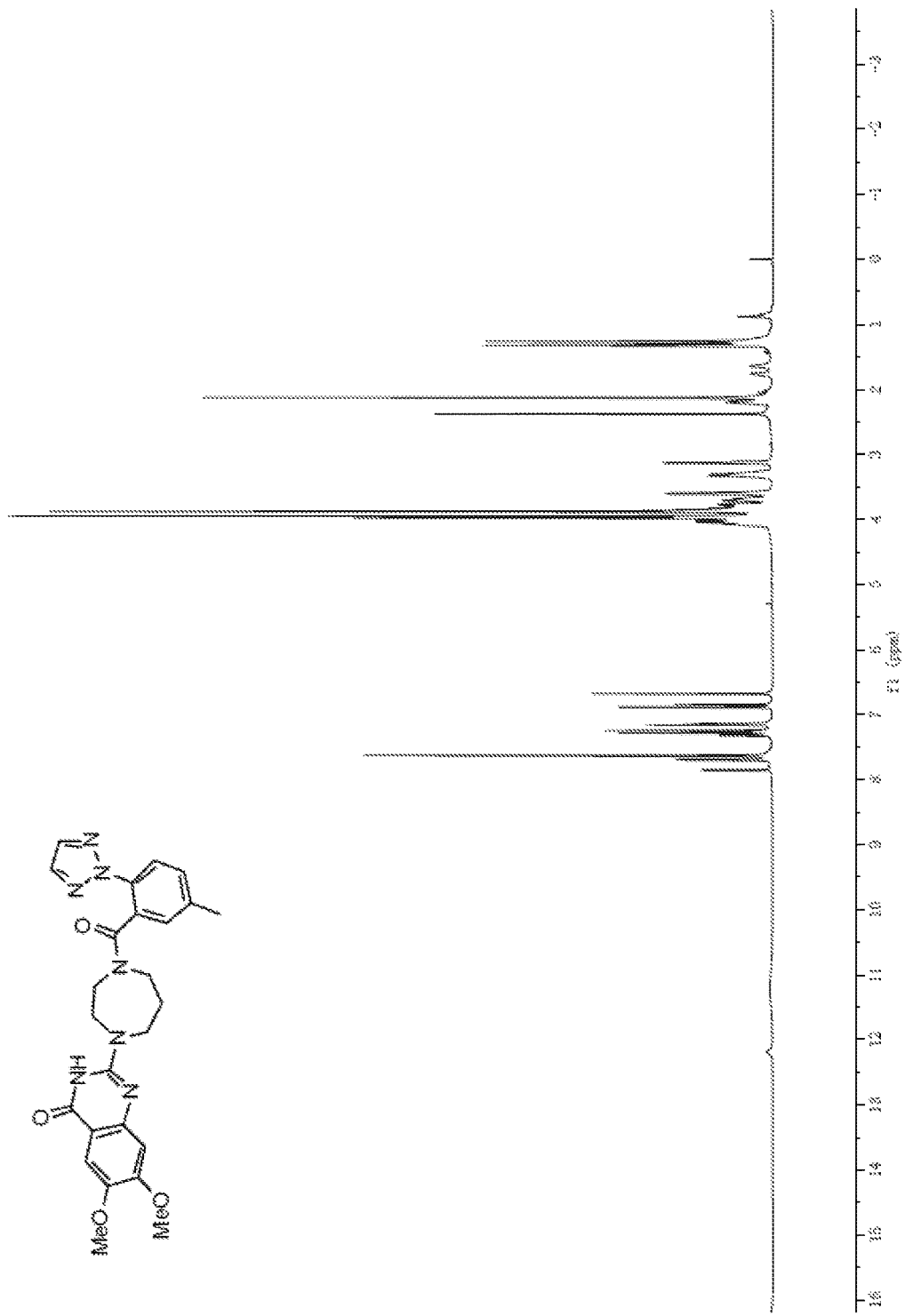
FIG. 9 shows the $^1$H NMR (CDCl$_3$, 600 MHz) spectrum of Example 21 of the invention.
Figure 10:
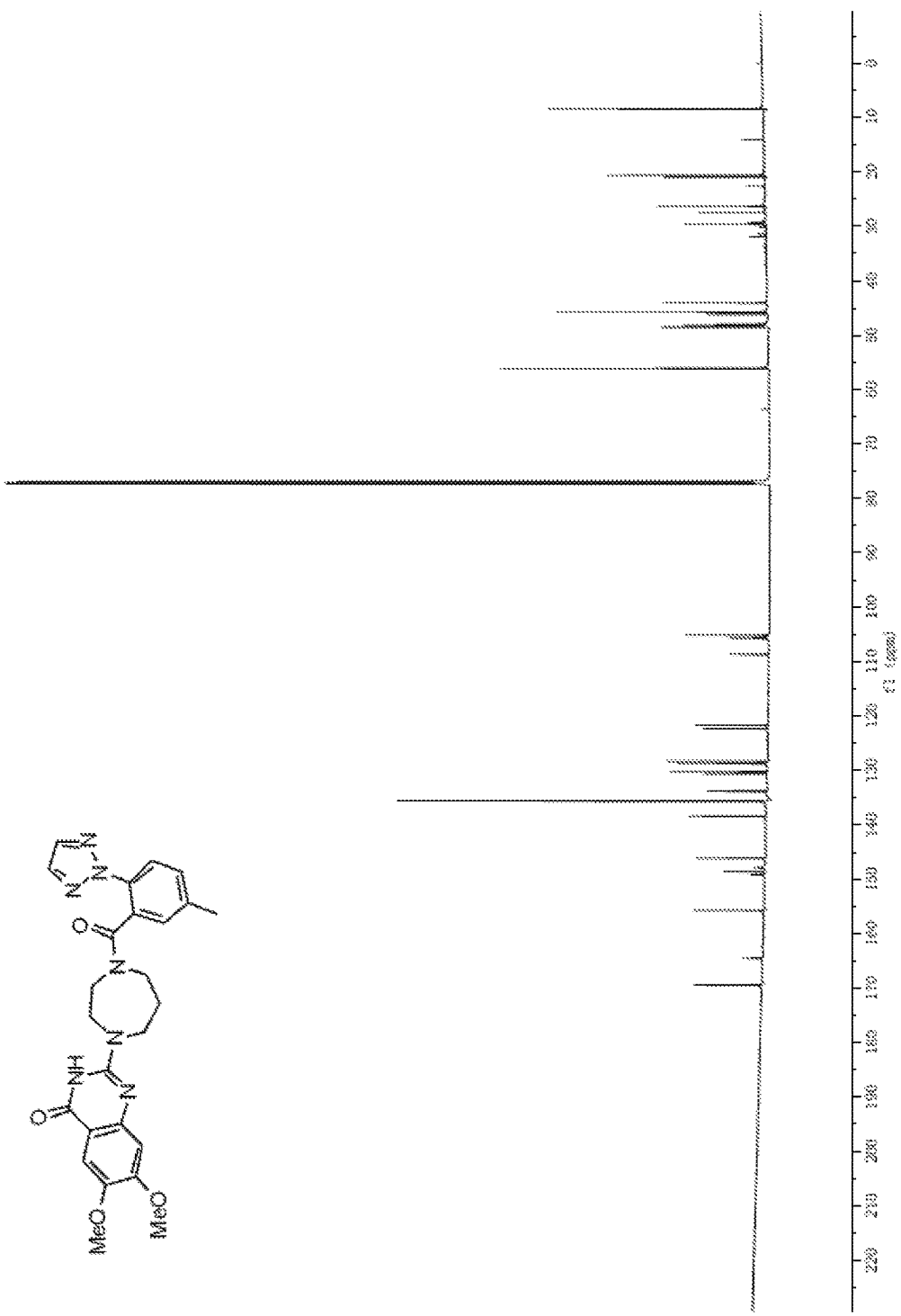
FIG. 10 shows the $^{13}$C NMR (CDCl$_3$, 151 MHz) spectrum of Example 21 of the invention.

$^1$H NMR (CDCl$_3$, 600 MHz) spectrum is shown in FIG. 9;

$^{13C}$ NMR (CDCl$_3$, 151 MHz) spectrum is shown in FIG. 10;

MS (ESI, pos. ion) m/z: 489.9 [M+H]$^+$; and

HPLC: 98.7%.

Example 22: Synthesis of 6,7-dimethoxy-2-(5-methyl-4-(5-methyl-2-(2H-1,2,3-triazol-2-yl)benzoyl)-1,4-diazepan-1-yl)quinazolin-4(3H)-one

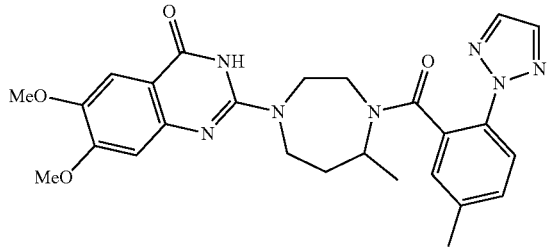 [SMILES: COc1cc2nc(N3CCC(C)N(C(=O)c4cc(C)ccc4-n4nccn4)CC3)[nH]c(=O)c2cc1OC]

Step 1) Synthesis of 6,7-dimethoxy-2-(5-methyl-1,4-diazepan-1-yl)quinazolin-4(3H)-one 5-Methyl-1,4-diazepane (0.11 g, 1.0 mmol) was reacted with 2-chloro-6,7-dimethoxyquinazolin-4(3H)-one (0.22 g, 0.9 mmol) in absolute ethanol (25 mL) according to the procedure as described in step 4 of example 1, and the crude product was purified by column chromatography on silica gel eluted with (dichloromethane/methanol (v/v)=10/1) to give the title compound (as a white solid, 0.24 g, 82%).

MS (ESI, pos. ion) m/z: 319.2 [M+H]$^+$; and $^1$H NMR (DMSO-d$_6$, 400 MHz) δ (ppm): 7.40 (s, 1H), 7.12 (s, 1H), 3.90 (s, 3H), 3.88 (s, 3H), 3.87~3.72 (m, 3H), 3.61~3.57 (m, 1H), 3.31~3.24 (m, 1H), 3.17~3.11 (m, 1H), 3.10~3.01 (m, 1H), 2.01~1.93 (m, 1H), 1.83~1.75 (m, 1H), 1.19 (d, J=6.0 Hz, 3H).

Step 2) Synthesis of 6,7-dimethoxy-2-(5-methyl-4-(5-methyl-2-(2H-1,2,3-triazol-2-yl) benzoyl)-1,4-diazepan-1-yl)quinazolin-4(3H)-one 6,7-Dimethoxy-2-(5-methyl-1,4-diazepan-1-yl)quinazolin-4(3H)-one (0.16 g, 0.50 mmol) was reacted with 5-methyl-2-(2H-1,2,3-triazole-2-yl)benzoyl chloride (0.13 g, 0.60 mmol) and triethylamine (0.28 mL, 2.0 mmol) in anhydrous dichloromethane (20 mL) according to the procedure as described in step 7 of example 1, and the crude product was purified by silica gel chromatography (dichloromethane/methanol (v/v)=80/1) to give the title compound (as a white solid, 0.15 g, 59%).

Figure 11:
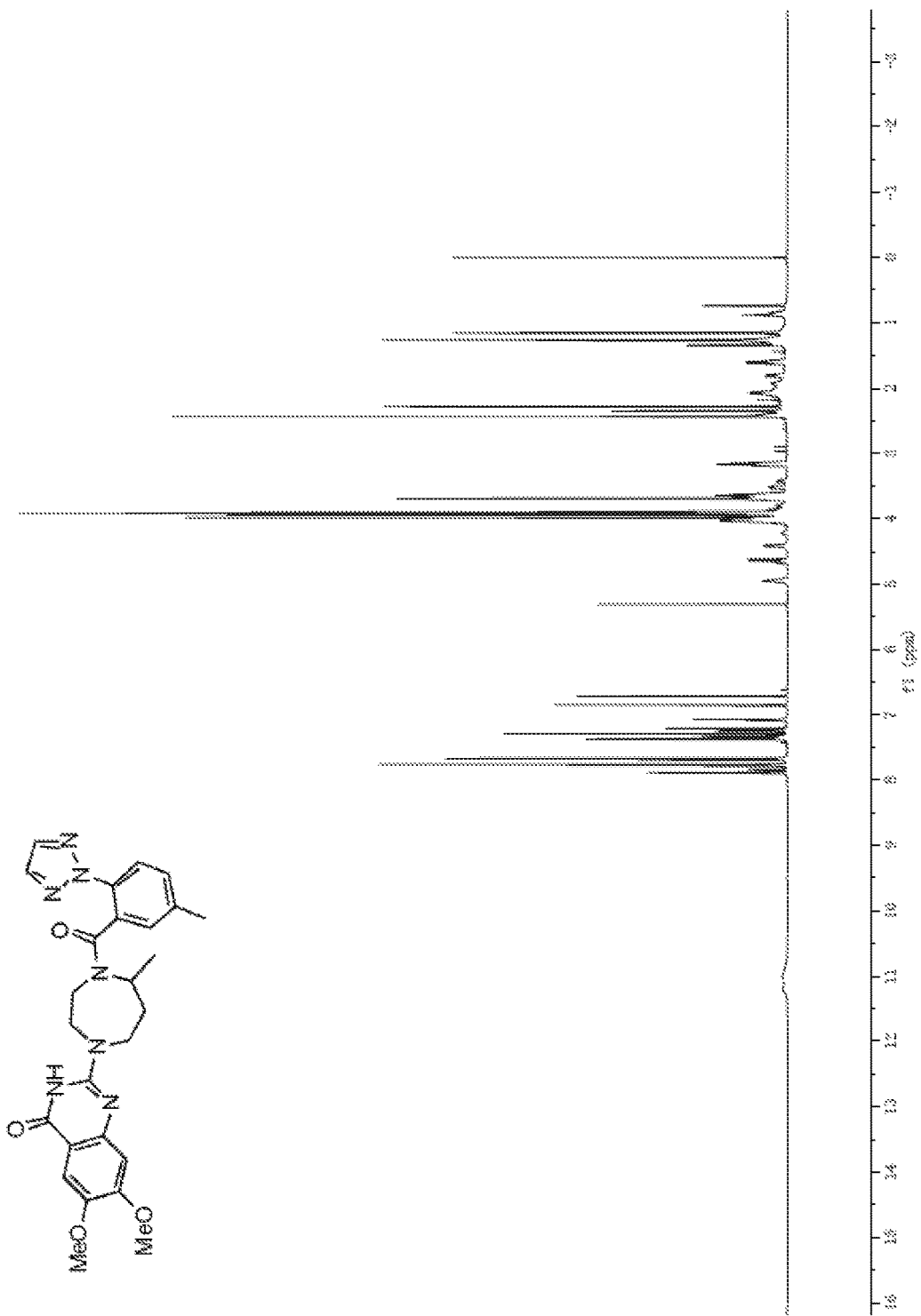
FIG. 11 shows the $^1$H NMR (CDCl$_3$, 600 MHz) spectrum of Example 22 of the invention.
Figure 12:
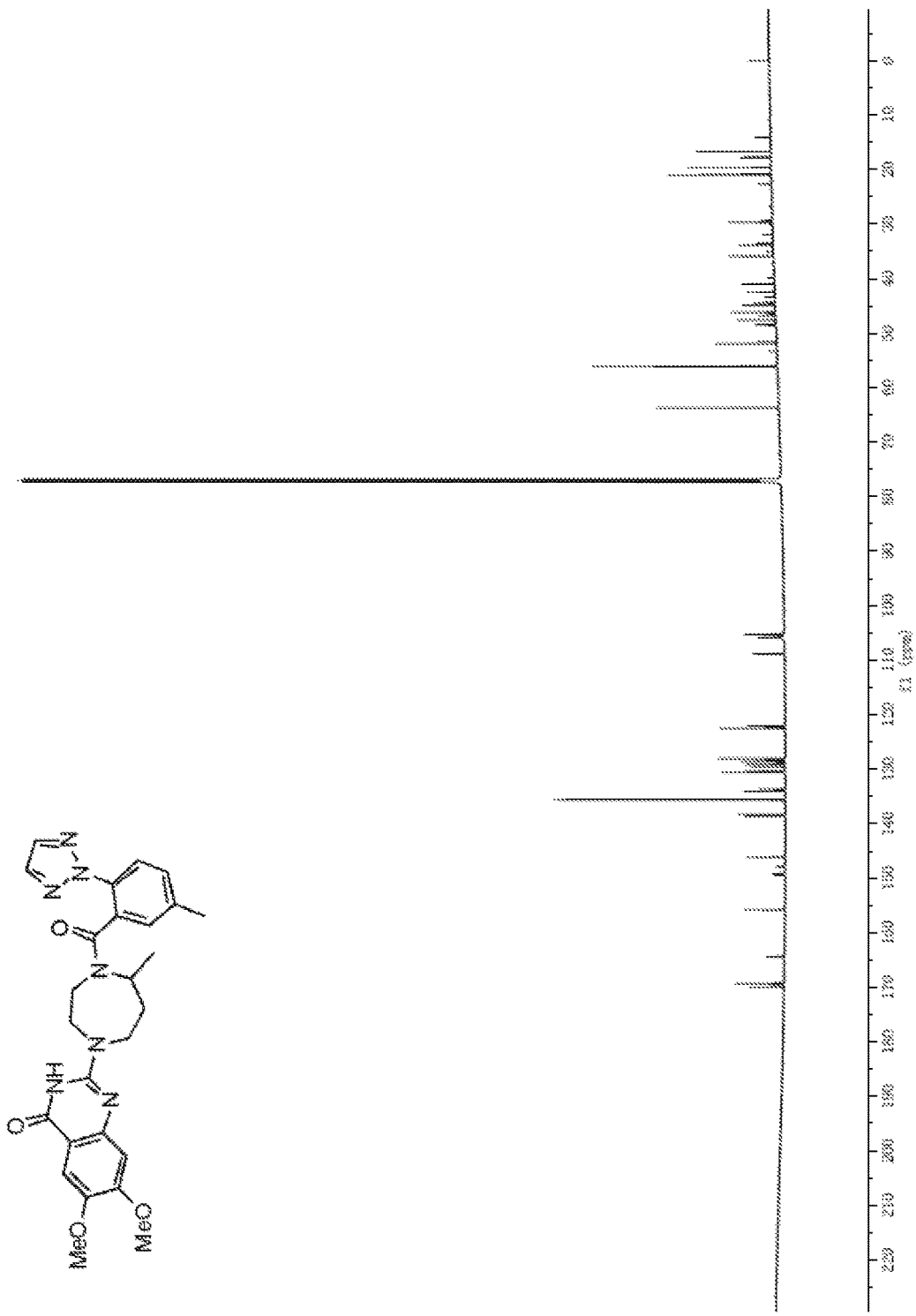
FIG. 12 shows the $^{13}$C NMR (CDCl$_3$, 151 MHz) spectrum of Example 22 of the invention.

$^1$H NMR (CDCl$_3$, 600 MHz) spectrum is shown in FIG. 11;
$^{13}$C NMR (CDCl$_3$, 151 MHz) spectrum is shown in FIG. 12;
MS (ESI, pos. ion) m/z: 504.3 [M+H]$^+$; and
HPLC: 99.3%.

Example 23: Synthesis of 2-(4-(2-(2H-1,2,3-triazol-2-yl)benzoyl)-1,4-diazepan-1-yl)-6,7-dimethoxyquinazolin-4(3H)-one

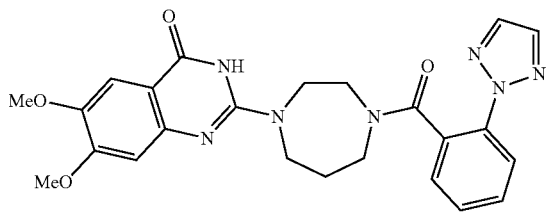 [SMILES: COc1cc2nc(N3CCCN(C(=O)c4ccccc4-n4nccn4)CC3)[nH]c(=O)c2cc1OC]

2-(1,4-Diazepan-1-yl)-6-methoxyquinazolin-4(3H)-one (0.18 g, 0.60 mmol) was reacted with 2-(2H-1,2,3-triazole-2-yl)benzoyl chloride (0.15 g, 0.72 mmol) and triethylamine (0.33 mL, 2.4 mmol) in anhydrous dichloromethane (20 mL) according to the procedure as described in step 7 of example 1, and the crude product was purified by silica gel chromatography (dichloromethane/methanol (v/v)=50/1) to give the title compound (as a white solid, 0.24 g, 83%).

Figure 13:
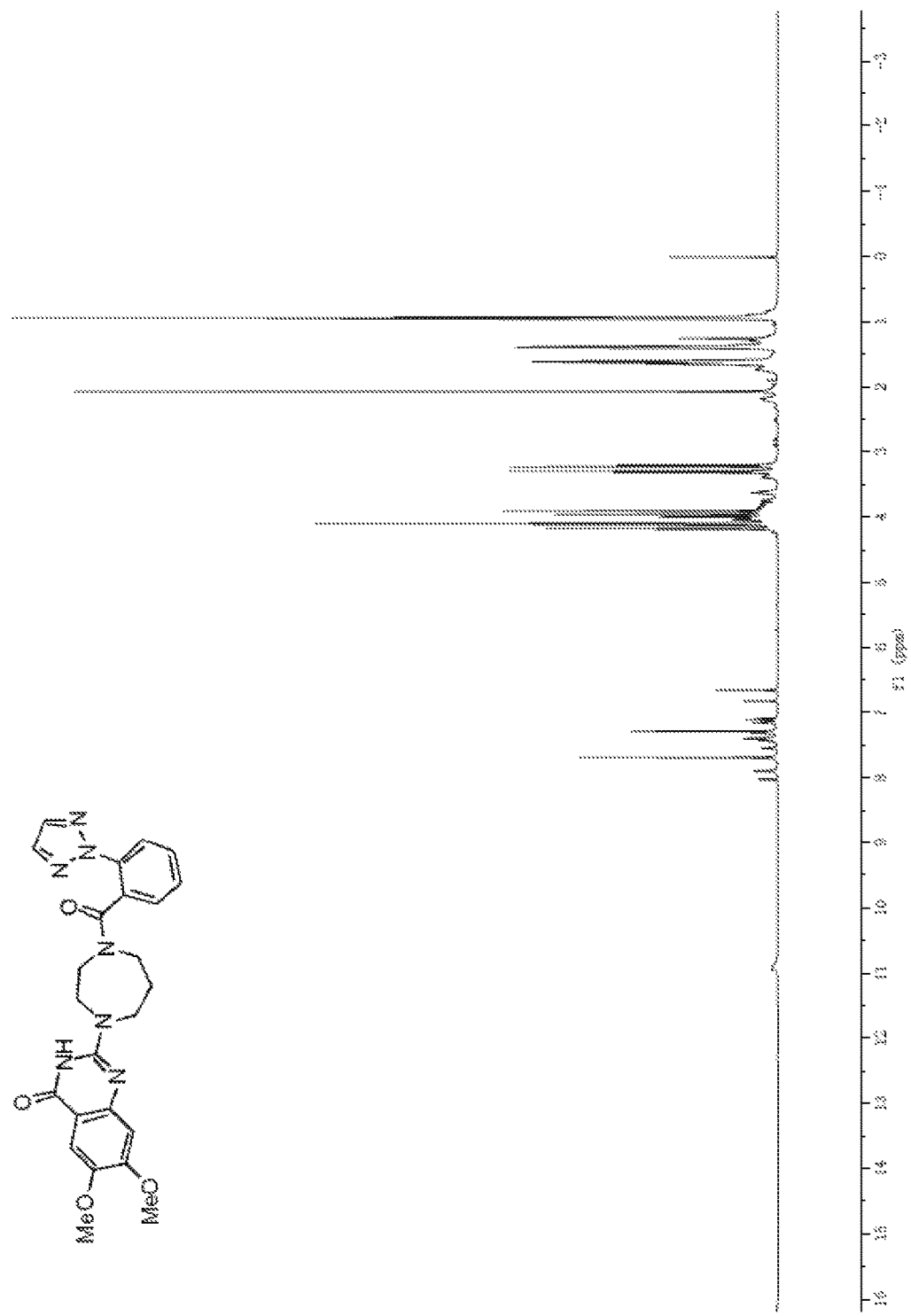
FIG. 13 shows the $^1$H NMR (CDCl$_3$, 600 MHz) spectrum of Example 23 of the invention.
Figure 14:
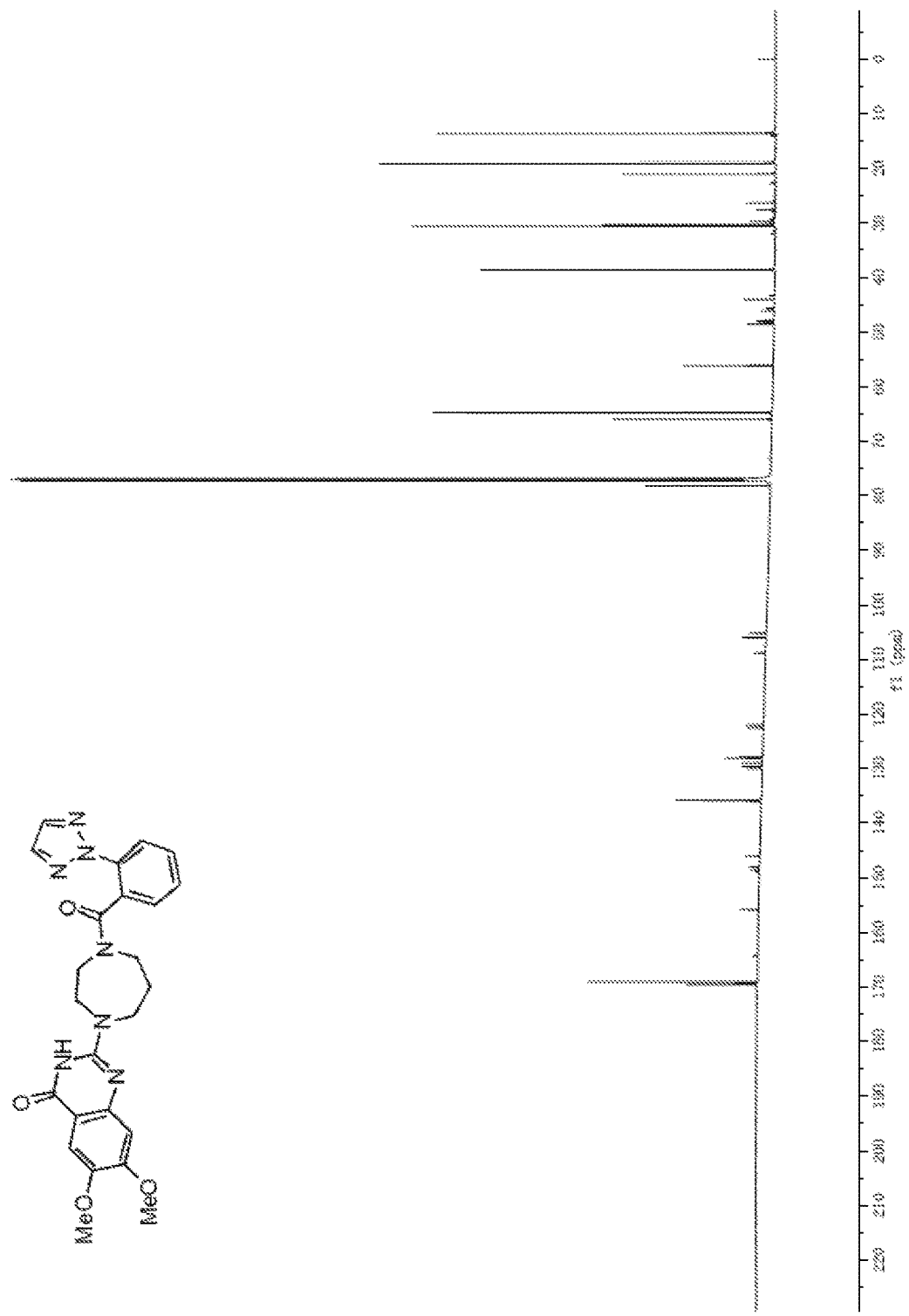
FIG. 14 shows the $^{13}$C NMR (CDCl$_3$, 151 MHz) spectrum of Example 23 of the invention.

$^1$H NMR (CDCl$_3$, 600 MHz) spectrum is shown in FIG. 13;
$^{13}$C NMR (CDCl$_3$, 151 MHz) spectrum is shown in FIG. 14;
MS (ESI, pos. ion) m/z: 475.9 [M+H]$^+$; and
HPLC: 97.3%.

Example 24: Synthesis of 2-(4-(2-(2H-1,2,3-triazol-2-yl)benzoyl)-5-methyl-1,4-diazepan-1-yl)-6,7-dimethoxyquinazolin-4(3H)-one

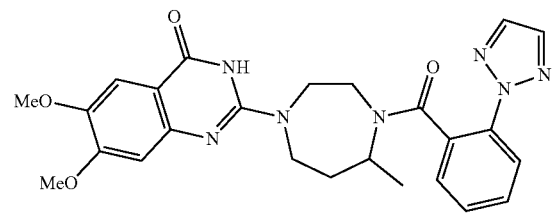 [SMILES: COc1cc2nc(N3CCC(C)N(C(=O)c4ccccc4-n4nccn4)CC3)[nH]c(=O)c2cc1OC]

6,7-Dimethoxy-2-(5-methyl-1,4-diazepan-1-yl)quinazolin-4(3H)-one (0.19 g, 0.60 mmol) was reacted with 2-(2H-1,2,3-triazole-2-yl)benzoyl chloride (0.15 g, 0.72 mmol) and triethylamine (0.33 mL, 2.4 mmol) in anhydrous dichloromethane (25 mL) according to the procedure as described in step 7 of example 1, and the crude product was purified by silica gel chromatography (dichloromethane/methanol (v/v)=50/1) to give the title compound (as a white solid, 0.22 g, 74%).

MS (ESI, pos. ion) m/z: 489.9 [M+H]$^+$; and
HPLC: 97.6%.

Example 25~Example 30

According to the synthetic scheme 1 or the synthesis method described in Example 1, the compounds of Example 25~Example 30 can be prepared by using the appropriate starting materials.

| Example No. | Structure | Characterization data |
|---|---|---|
| Example 25 | ![structure] | MS (ESI, pos. ion) m/z: 452.2 [M + H]$^+$ |
| Example 26 | ![structure] | MS (ESI, pos. ion) m/z: 466.2 [M + H]$^+$ |

-continued

| Example No. | Structure | Characterization data |
| --- | --- | --- |
| Example 27 | 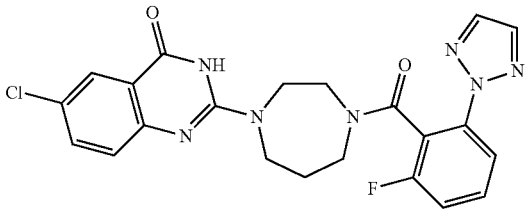 [SMILES: O=C(c1c(F)cccc1-n1nccn1)N1CCCN(c2nc3ccc(Cl)cc3c(=O)[nH]2)CC1] | MS (ESI, pos. ion) m/z: 468.2 [M + H]$^+$ |
| Example 28 | 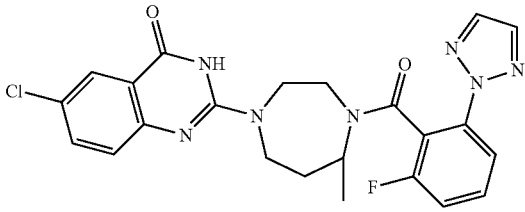 [SMILES: CC1CCN(c2nc3ccc(Cl)cc3c(=O)[nH]2)CCN1C(=O)c1c(F)cccc1-n1nccn1] | MS (ESI, pos. ion) m/z: 482.2 [M + H]$^+$ |
| Example 29 | 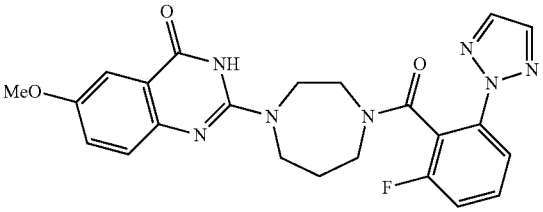 [SMILES: COc1ccc2nc(N3CCCN(C(=O)c4c(F)cccc4-n4nccn4)CC3)[nH]c(=O)c2c1] | MS (ESI, pos. ion) m/z: 464.2 [M + H]$^+$ |
| Example 30 | 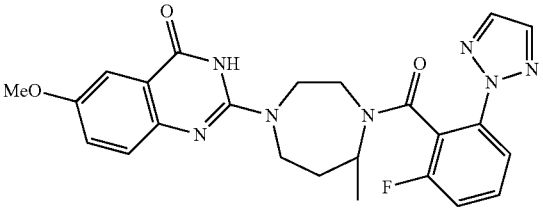 [SMILES: COc1ccc2nc(N3CCC(C)N(C(=O)c4c(F)cccc4-n4nccn4)CC3)[nH]c(=O)c2c1] | MS (ESI, pos. ion) m/z: 478.2 [M + H]$^+$ |

Biological Assay

Example A: Antagonism of Humanized OX$_1$ Receptor Assay

Test Method

The capability of the compounds to the antagonism of humanized OX$_1$ receptor transfected to the Chinese hamster ovary (CHO) cells was evaluated by the method of fluorescence detected free calcium concentration in the cytoplasm. The cells were suspended in a cell culture medium (invitrogen), and then plated to a microplate with an average density of 2×10$^4$ cells/well. The fluorescent probes (Fluo4 NW, Invitrogen) was mixed with probenecid Hank's balanced salt solution (invitrogen), followed by addition of 20 mM hydroxyethyl piperazine acetic sulfuric acid (invitrogen) (pH 7.4). The resulting mixture was eventually added to the microwells containing cells. The cells were incubated at 37° C. for 60 min, and then balanced at 22° C. for 15 min. The microplate was placed in a microplate reader (CellLux, PerkinElmer), and the solution of test compound with different concentrations or Hank's balanced salt solution was added. The microplate containing the solution was incubated for 5 min, followed by the addition of 3 nM of orexin A or a balanced salt solution (as control). The changes of fluorescence intensity proportional to the concentration of calcium ions in the cytoplasm were measured.

Data Analysis

With the substrate control as 0 and 3 nM orexin A as 100%, inhibition rate of each compound was recorded. Referring to the compound SB334867, several different concentrations were measured in each experiment. Dose-response curves were made, and IC$_{50}$ value of each compound was calculated. The results are shown in Table 1.

TABLE 1

The experimental results of the antagonism of the compounds disclosed herein to humanized OX$_1$ receptor

| Example Number | OX$_1$ IC$_{50}$(μM) |
| --- | --- |
| Example 1 | 0.322 |
| Example 2 | 0.543 |
| Example 5 | 0.276 |
| Example 6 | 0.367 |

The test results indicate that the compounds of the present invention, in the experiment above, exhibited good antagonism to OX$_1$ receptor.

Example B: Antagonism of Humanized $OX_2$ Receptor Assay

Test Method

The capability of the compounds to antagonism of humanized $OX_2$ receptor transfected by the HEK-293 cells was evaluated by the method of fluorescence detected free calcium concentration in the cytoplasm. The cells were suspended in cell culture medium (invitrogen), and then added to a microplate with an average density of $3 \times 10^4$ cells/well. The fluorescent probes (Fluo4 NW, Invitrogen) was mixed with probenecid Hank's balanced salt solution (invitrogen), followed by addition of 20 mM hydroxyethyl piperazine acetic sulfuric acid (invitrogen) (pH 7.4). The resulting mixture was eventually added to the microwells containing cells. The cells were incubated at 37° C. for 60 min, and then balanced at 22° C. for 15 min. The microplate was placed in a microplate reader (CellLux, PerkinElmer), and the solution of test compound with different concentrations or Hank's balanced salt solution was added. The microplate containing the solution was incubated for 5 min, followed by the addition of 10 nM of orexin B or a balanced salt solution (as control). The changes of fluorescence intensity proportional to the concentration of calcium ions in the cytoplasm were measured.

Data Analysis

With the substrate control as 0 and 10 nM of orexin B as 100%, inhibition rate of each compound was recorded. Referring to the compound JNJ10397049, several different concentrations were measured in each experiment. Dose-response curves were made, and $IC_{50}$ value of each compound was calculated. The results are shown in Table 2.

TABLE 2

The experimental results of the antagonism of the compounds disclosed herein to humanized $OX_2$ receptor

| Example Number | $OX_2$ $IC_{50}(\mu M)$ |
|---|---|
| Example 1 | 0.300 |
| Example 2 | 0.169 |
| Example 5 | 0.263 |
| Example 6 | 0.221 |

The test results indicate that the compounds of the present invention, in the experiment above, exhibited good antagonism to $OX_2$ receptor.

Example C: Pharmacokinetic Evaluation of Rats, Dogs and Monkeys with Intravenous or Oral Quantification of the Compound of the Present Invention Pharmacokinetics of the compound of the present invention in rats, dogs or monkeys was evaluated in the present invention. The compounds of this invention were administered with a saline solution of 5% DMSO+5% Kolliphor HS 15+2% (2% HCl)+88% Saline or 10% DMSO+10% Kolliphor HS 15+80% physiological. For intravenous administration, the animals were given a dose of 1 mg/kg, drew blood (0.3 mL) at the time point of 0.083, 0.25, 0.5, 1.0, 2.0, 4.0, 6.0, 8.0 and 24 h, and centrifuged in 3,000 or 4,000 rpm for 10 min. For oral (p.o.) administration, the animals were given a dose of 2.5 mg/kg or 5 mg/kg, drew blood (0.3 mL) at the time point of 0.25, 0.5, 1.0, 2.0, 4.0, 6.0, 8.0 and 24 h, and centrifuged in 3,000 or 4,000 rpm for 10 min. Plasma solution was collected and was stored at −20° C. or −70 V until LC/MS/MS analysis.

The test results indicated that the compounds of the present invention had good pharmacokinetic properties in rats, dogs or monkeys. Pharmacokinetic parameters of the compounds of Example 2, Example 6 and Example 7 in rats are shown in the Table 3.

TABLE 3

Pharmacokinetic parameters of the compound of the invention in rats

| | grouping | | | | | |
|---|---|---|---|---|---|---|
| | Intravenous administration group | | | Oral administration group | | |
| | Example | | | | | |
| | Example 2 | Example 6 | Example 7 | Example 2 | Example 6 | Example 7 |
| Dose (mg/kg) | 1 | 1 | 1 | 2.5 | 5 | 5 |
| $AUC_{INF}$ (h * ng/mL) | 866 | 1740 | 3700 | 1780 | 6840 | 15000 |
| $AUC_{last}$ (h * ng/mL) | 865 | 1730 | 3450 | 1770 | 6800 | 14300 |
| Cl (mL/min/kg) | 19.2 | 9.66 | 4.52 | — | — | — |
| $C_{max}$ (ng/mL) | 1400 | 3660 | 4080 | 1940 | 5680 | 13800 |
| $T_{max}$ (h) | 0.083 | 0.083 | 0.083 | 0.333 | 0.333 | 0.25 |
| $V_{ss}$ (L/kg) | 0.66 | 0.292 | 1.33 | — | — | — |
| F (%) | — | — | — | 81.8 | 79 | 83.1 |

Example D: Evaluation of the Potential of the Compound Disclosed Herein Inducing Prolongation of QT Interval Test Method The potential of the compound disclosed herein inducing QT interval prolongation was evaluated by detecting if the compound would block the hERG channel. The specific test method is as follows:

Precisely weighed compound disclosed herein was dissolved in DMSO to formulate a solution at the highest concentration of 10.0 mM, and then the solution was diluted to a initial concentration of 120.0 μM with hERG FP Assay Buffer (Invitrogen); the hERG Tracer Red stock solution (Invitrogen) and the positive control E-4031 stock solution were respectively diluted to initial concentrations of 4.0 nM and 120.0 μM with hERG FP Assay Buffer (Invitrogen). 2.5 μL of the compound disclosed herein at a initial concentration or the positive control E-4031 at a initial concentration (positive control group) or hERG FP Assay Buffer (negative control group), 5 μL of hERG Membrane and 2.5 μL of hERG Tracer Red were added into a 384-well plate, and 5 μL of hERG FP Assay Buffer and 5 μL of hERG Membrane were added as a blank control group, and the test final concentration of the compound disclosed herein, E-4031 and hERG Tracer Red were respectively 30.0 μM, 30.0 μM and 1.0 nM. Four duplicated wells per group were established. After that, the 384-well plate was put in to an oscillator (PHMP-4, Grant-sio), in 25° C., 250 rpm, to incubate for 4 hours, and the fluorescence polarization values were measured by multi-function microplate reader (PHERAStarFS, BMG LABTECH), and the relative inhibition rate and 50% inhibition concentration ($IC_{50}$) of the compound disclosed herein to hERG channel were calculated.

In the case of E-4031 as a positive control, if the relative inhibition rate of 30.0 μM of the compound disclosed herein to hERG was less than 50%, the $IC_{50}$ of the compound disclosed herein to hERG channel was more than 30.0 μM. If the relative inhibition rate of 30.0 μM of the compound disclosed herein to hERG was more than 50%, the dose titration curve of the compound of this invention is necessary, and the specific method is as follows:

The above-mentioned solution of the compound disclosed herein and E-4031 at the initial concentration of 120 μM were respectively diluted with hERG FP Assay Buffer 5-fold in series to provide 8 concentration of 120.0 μM, 24.0 μM, 4.8 μM, 960.0 nM, 192.0 nM, 38.4 nM, 7.7 nM and 1.5 nM. Two duplicated wells per concentration were established. 2.5 μL of the compound disclosed herein or the positive control E-4031 (positive control group) or hERG FP Assay Buffer (negative control group) at the indicated concentrations, 5 μL of hERG FP Membrane and 2.5 μL of hERG Tracer Red were added into a 384-well plate, and 5 μL of hERG FP Assay Buffer and 5 μL of hERG Membrane were added as a blank control group. After that, the 384-well plate was put into an oscillator (PHMP-4, Grant-sio), in 25° C., 250 rpm, to incubate for 4 hours, and the fluorescence polarization values were measured by multi-function microplate reader (PHERAStarFS, BMG LABTECH) and corrected with the minimum and maximum fluorescence polarization values of E-4031, and the $IC_{50}$ of the compound disclosed herein was calculated by GraphPad software.

The experimental results show that the $IC_{50}$ of the compound disclosed herein to hERG channel is more than 30 μM, i.e., the compound of this invention has no or weak inhibitory activity to hERG channel, which prompts less risk to cause QT interval elongation.

Finally, it should be noted that there are other ways to practice the invention. Accordingly, embodiments of the present invention is to be described as examples, but the present invention is not limited to the contents described, further modifications may be made within the scope of the present invention or the equivalents added in the claims.

All publications or patents cited herein are incorporated by reference in this invention.

Reference throughout this specification to "an embodiment", "some embodiments", "one embodiment", "another example", "an example", "a specific examples" or "some examples" means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, an N-oxide, or a pharmaceutically acceptable salt,

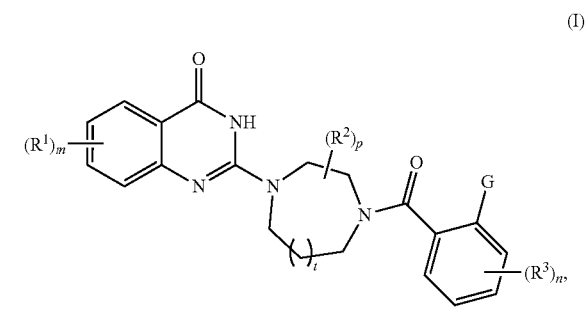

wherein,

G is a 5-membered heterocycloalkyl or heteroaryl group containing at least one nitrogen, wherein G is optionally substituted with one or more $R^8$;

each $R^1$ is independently H, D, F, Cl, Br, I, OH, $NH_2$, $NO_2$, CN, $N_3$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ hydroxyalkyl, $C_{1-6}$ alkylamino, $C_{3-12}$ carbocyclyl, 3- to 12-membered heterocyclyl, $C_{6-10}$ aryl or 5- to 12-membered heteroaryl, wherein each $R^1$ is optionally and independently substituted with one or more $R^8$;

each $R^2$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ hydroxyalkyl or $C_{1-4}$ haloalkyl;

each $R^3$ is independently H, D, F, Cl, Br, I, OH, $NH_2$, $NO_2$, CN, $N_3$, $C_{1-6}$ alkyl, $C_{2-6}$ alkenyl, $C_{2-6}$ alkynyl, $C_{3-12}$ carbocyclyl, 3- to 12-membered heterocyclyl, $C_{6-10}$ aryl or 5- to 12-membered heteroaryl, $-(CR^4R^{4a})_q-OR^7$, $-(CR^4R^{4a})_q-NR^5R^6$, $-(CR^4R^{4a})_qS(=O)_rR^7$, $-(CR^4R^{4a})_qS(=O)_2NR^5R^6$, $-(CR^4R^{4a})_qC(=O)R^7$, $-(CR^4R^{4a})_qOC(=O)R^7$, $-(CR^4R^{4a})_qC(=O)OR^7$, $-(CR^4R^{4a})_q-N(R^5)C(=O)R^7$, $-C(=NR^7)NR^5R^6$, $-N(R^7)C(=O)NR^5R^6$, $-(CR^4R^{4a})_q-N(R^5)S(=O)_rR^7$ or $-(CR^4R^{4a})_qC(=O)NR^5R^6$, wherein each $R^3$ is optionally and independently substituted with one or more $R^8$;

wherein each $R^4$ and $R^{4a}$ is independently H, D, F, Cl, Br, I, CN, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ haloalkoxy, $C_{1-4}$ haloalkylamino, $C_{3-8}$ carbocyclyl, 3- to 8-membered heterocyclyl, $C_{6-10}$ aryl or 5- to 6-membered heteroaryl;

each $R^5$, $R^6$ and $R^7$ is independently H, $C_{1-4}$ alkyl, $C_{2-4}$ alkenyl, $C_{2-4}$ alkenyl, $C_{3-8}$ carbocyclyl, ($C_{3-6}$ cycloalkyl)-($C_{1-4}$ alkylene)-, 3- to 8-membered heterocyclyl, (3- to 6-membered heterocyclyl)-($C_{1-4}$ alkylene)-, phenyl, ($C_{6-10}$ aryl)-($C_{1-4}$ alkylene)-, 5- to 6-membered heteroaryl or (5- to 6-membered heteroaryl)-($C_{1-4}$ alkylene)-, or $R^5$ and $R^6$ together with the nitrogen atom to which they are attached, independently and optionally form 3- to 6-membered heterocyclyl, wherein each $C_{1-4}$ alkyl, $C_{2-4}$ alkenyl, $C_{2-4}$ alkynyl and $C_{3-8}$ carbocyclyl is optionally and independently substituted with one or more substituents independently selected from D, F, Cl, Br, OH, $NH_2$, CN, $N_3$, $C_{1-4}$ alkyl, $C_{1-4}$ haloalkyl, $C_{1-4}$ alkoxy or $C_{1-4}$ alkylamino;

each $R^8$ is independently H, D, F, Cl, Br, I, =O, OH, $NH_2$, $NO_2$, CN, $N_3$, $C_{1-4}$ alkyl, $C_{2-4}$ alkenyl, $C_{2-4}$ alkynyl, $C_{1-4}$ alkoxy, $C_{1-4}$ alkylamino, $C_{1-4}$ haloalkyl, $C_{1-4}$ haloalkoxy, $C_{1-4}$ hydroxyalkyl or $C_{1-4}$ haloalkylamino;

each m and n is independently 0, 1, 2, 3, or 4;

t is 0 or 1;

p is 0, 1, 2, 3, 4, or 5;

each r is independently 0, 1 or 2; and each q is independently 0, 1, 2, 3, or 4.

2. The compound of claim 1, wherein G is:

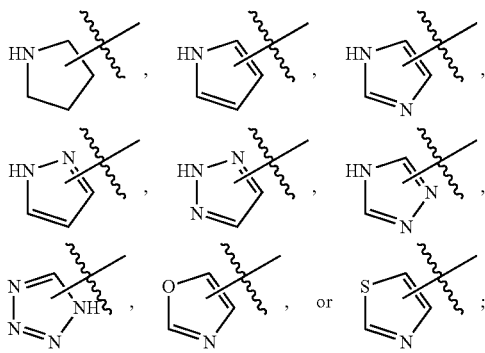

and G is optionally substituted with one or more $R^8$.

3. The compound of claim 1, wherein each $R^1$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{1-4}$ haloalkyl, $C_{1-4}$ alkoxy, $C_{1-4}$ hydroxyalkyl, $C_{1-4}$ alkylamino, $C_{3-8}$ carbocyclyl, 3- to 8-membered heterocyclyl, $C_{6-10}$ aryl or 5- to 6-membered heteroaryl, wherein each $R^1$ is optionally and independently substituted with one or more $R^8$.

4. The compound of claim 1, wherein each $R^1$ is independently H, D, F, Cl, Br, OH, $NH_2$, $NO_2$, CN, methyl, ethyl, n-propyl, isopropyl, n-butyl, isobutyl, vinyl, ethynyl, methoxy, ethoxy, methylamino, ethylamino, hydroxymethyl, hydroxyethyl, trifluoromethyl, cyclopropyl, piperidinyl, piperazinyl, morpholinyl, phenyl, pyrrolyl, imidazolyl, thiazolyl or thienyl.

5. The compound of claim 1, wherein each $R^2$ is independently H, F, Cl, OH, $NH_2$, $NO_2$, CN, methyl, ethyl, n-propyl, isopropyl, vinyl, allyl, propargyl, methoxy, ethoxy, methylamino, ethylamino, hydroxymethyl, hydroxyethyl or trifluoromethyl.

6. The compound of claim 1, wherein each $R^3$ is independently H, D, F, Cl, Br, I, OH, $NH_2$, $NO_2$, CN, $N_3$, $C_{1-4}$ alkyl, $C_{2-4}$ alkenyl, $C_{2-4}$ alkynyl, $C_{3-8}$ carbocyclyl, 3- to 8-membered heterocyclyl, $C_{6-10}$ aryl, 5- to 6-membered heteroaryl, $-(CR^4R^{4a})_q-OR^7$, $-(CR^4R^{4a})_q-NR^5R^6$, $-(CR^4R^{4a})_qS(=O)_rR^7$, $-(CR^4R^{4a})_qS(=O)_2NR^5R^6$, $-(CR^4R^{4a})_qC(=O)R^7$, $-(CR^4R^{4a})_qOC(=O)R^7$, $-(CR^4R^{4a})_qC(=O)OR^7$, $-(CR^4R^{4a})_q-N(R^5)C(=O)R^7$, $-C(=NR^7)NR^5R^6$, $-N(R^7)C(=O)NR^5R^6$, $-(CR^4R^{4a})_q-N(R^5)S(=O)_rR^7$ or $-(CR^4R^{4a})_qC(=O)NR^5R^6$, wherein each $R^3$ is optionally and independently substituted with one or more $R^8$.

7. The compound of claim 1, wherein each $R^3$ is independently H, D, F, Cl, Br, OH, $NH_2$, $NO_2$, CN, methyl, ethyl, n-propyl, isopropyl, n-butyl, isobutyl, vinyl, ethynyl, methoxy, ethoxy, methylamino, ethylamino, hydroxymethyl, hydroxyethyl, trifluoromethyl, cyclopropyl, piperidinyl, piperazinyl, morpholinyl, phenyl, pyrrolyl, imidazolyl, thiazolyl, thienyl, $-C(=O)NH_2$ or $-COOH$.

8. The compound of claim 1, wherein each $R^4$ and $R^{4a}$ is independently H, D, F, Cl, Br, I, CN, methyl, ethyl, isopropyl, vinyl, allyl, ethynyl, propargyl, methoxy, tert-butoxy, methylamino, $-OCF_3$, $-NHCF_3$, cyclopentyl, cyclohexyl, piperidin-1-yl, piperazin-1-yl, pyridin-2-yl, phenyl or naphthyl; and each $R^5$, $R^6$ and $R^7$ is independently H, methyl, ethyl, isopropyl, vinyl, allyl, ethynyl, propargyl, cyclopentyl, cyclohexyl, cyclohexylmethyl, piperidin-1-yl, piperazin-1-yl, imidazol-1-yl, pyridin-4-yl-methyl, phenyl or benzyl, or $R^5$ and $R^6$ together with the nitrogen atom to which they are attached, form pyrrolidinyl, piperazinyl, imidazolidinyl or morpholinyl.

9. The compound of claim 1, wherein each $R^8$ is independently H, D, F, Cl, Br, I, =O, OH, $NH_2$, $NO_2$, CN, $N_3$, methyl, ethyl, ethynyl, propynyl, methoxy, tert-butoxy, methylamino, trifluoromethyl, trifluoromethoxy, hydroxymethyl or trifluoromethylamino.

10. The compound of claim 1 having one of the following structures:

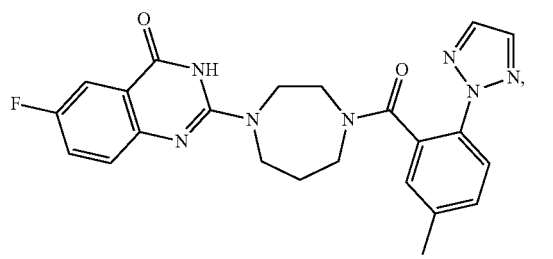

(1)

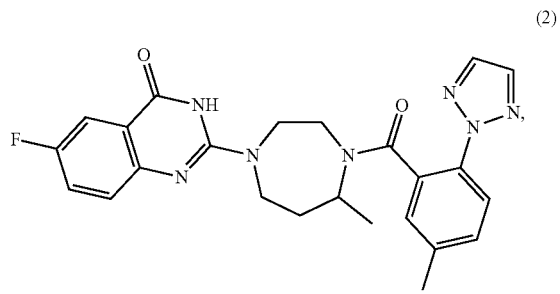

(2)

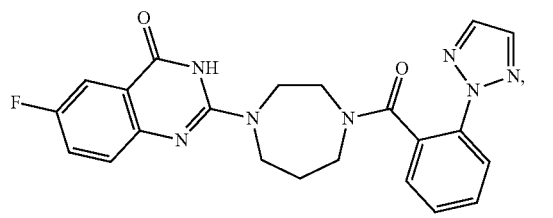

(3)

(4)
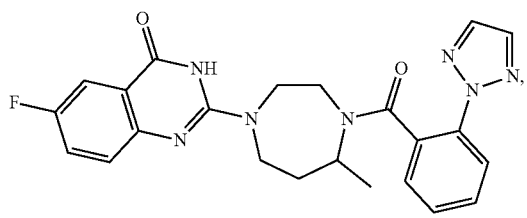
(5)
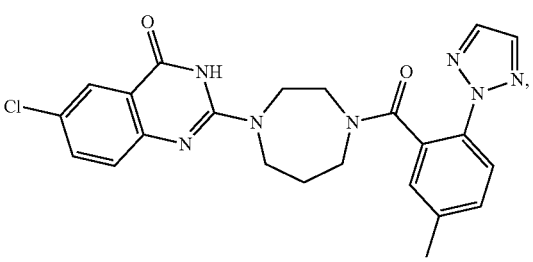
(6)
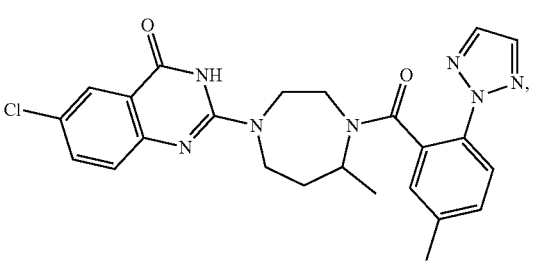
(7)
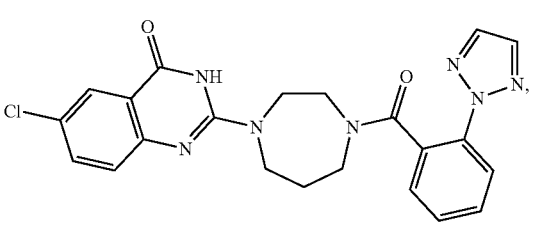
(8)
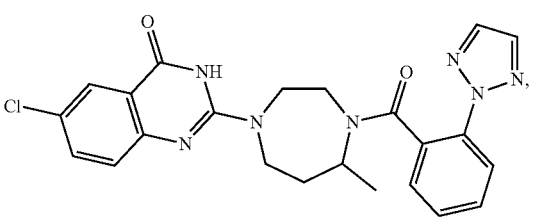
(9)
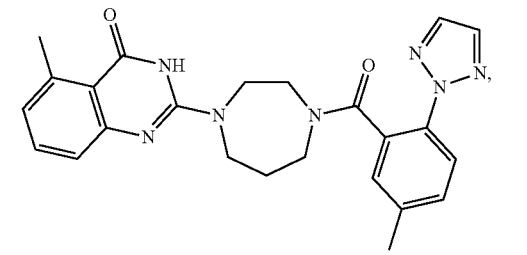
(10)
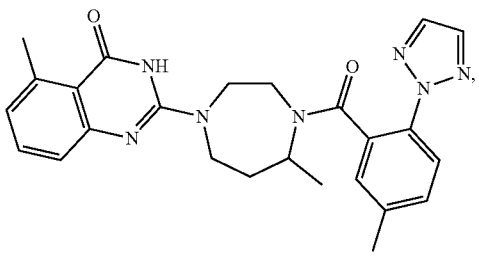
(11)
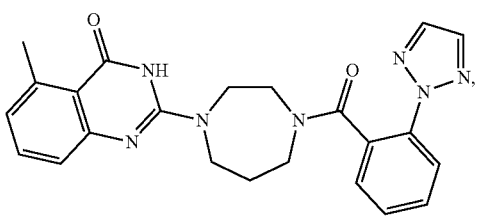
(12)
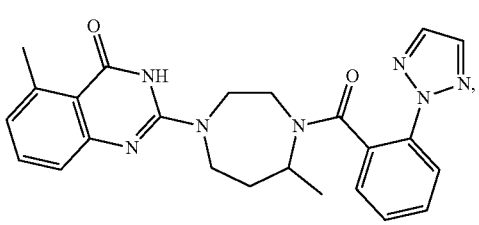
(13)
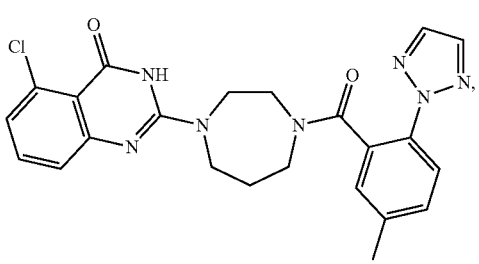
(14)
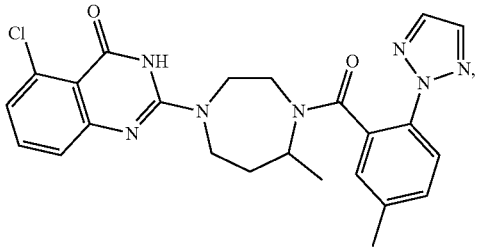
(15)
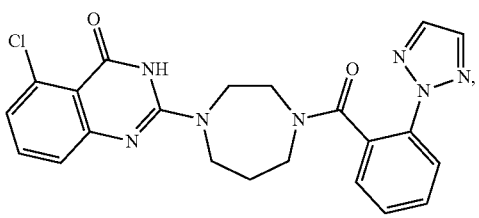

-continued

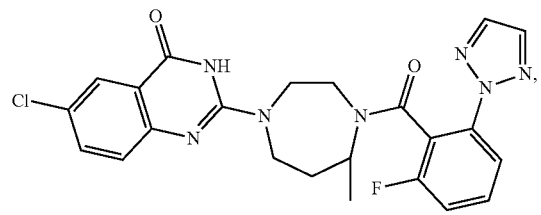
(28)
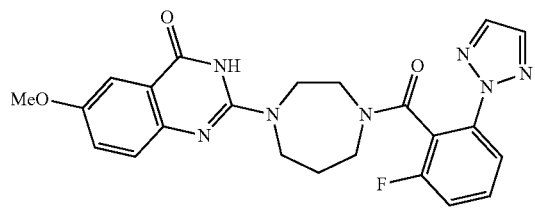
(29)
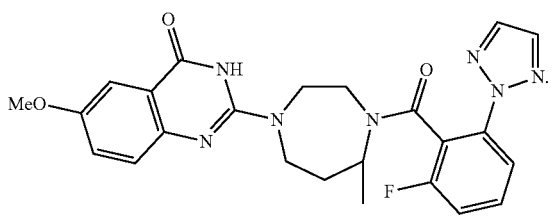
(30)
11. A pharmaceutical composition comprising the compound according to claim 1 and a pharmaceutically acceptable excipient, carrier, adjuvant, solvent or a combination thereof.
* * * * *